United States Patent [19]

Fahy et al.

[11] Patent Number: 5,821,045

[45] Date of Patent: Oct. 13, 1998

[54] METHODS FOR REMOVAL OF CRYOPROTECTANT FROM ORGANS PRIOR TO TRANSPLANTATION

[75] Inventors: Gregory M. Fahy, Gaithersburg; Bijan Khirabadi, Rockville, both of Md.; Yasumitsu Okouchi, Hazelwood, Mo.

[73] Assignee: The American National Red Cross, Washington, D.C.

[21] Appl. No.: 455,027

[22] Filed: May 31, 1995

Related U.S. Application Data

[60] Division of Ser. No. 292,001, Aug. 18, 1994, Pat. No. 5,723,282, which is a continuation-in-part of Ser. No. 72,754, Jun. 7, 1993, abandoned, which is a continuation-in-part of Ser. No. 725,054, Jul. 8, 1991, Pat. No. 5,217,860.

[51] Int. Cl.$^6$ ...................................................... A01N 1/02
[52] U.S. Cl. ............................................. 435/1.2; 435/1.3
[58] Field of Search .................................. 435/1, 1.2, 1.3

[56] References Cited

U.S. PATENT DOCUMENTS

| | | | |
|---|---|---|---|
| 3,639,084 | 2/1972 | Goldhaber | 417/394 |
| 3,677,024 | 7/1972 | Segall | 62/64 |
| 3,753,865 | 8/1973 | Belzer et al. | 195/127 |
| 3,772,153 | 11/1973 | De Roissart | 195/127 |
| 3,843,455 | 10/1974 | Bier | 195/127 |
| 3,892,628 | 7/1975 | Thorne et al. | 195/1.7 |
| 3,914,954 | 10/1975 | Doerig | 62/306 |
| 3,940,943 | 3/1976 | Sikes et al. | 62/64 |
| 3,995,444 | 12/1976 | Clark et al. | 62/306 |
| 4,186,565 | 2/1980 | Toledo-Pereyra | 62/306 |
| 4,471,629 | 9/1984 | Toledo-Pereyra | 62/64 |
| 4,494,385 | 1/1985 | Kuraoka et al. | 62/306 |
| 4,559,298 | 12/1985 | Fahy | 435/1 |
| 4,618,586 | 10/1986 | Walker | 435/1 |
| 4,629,686 | 12/1986 | Gruenberg | 435/1 |
| 4,688,387 | 8/1987 | Conaway | 62/78 |
| 4,704,029 | 11/1987 | Van Heuvelen | 356/39 |
| 4,745,759 | 5/1988 | Bauer et al. | 62/3 |
| 4,798,824 | 1/1989 | Belzer et al. | 514/60 |
| 4,837,390 | 6/1989 | Reneau | 435/1 |
| 4,879,283 | 11/1989 | Belzer et al. | 514/60 |
| 5,051,352 | 9/1991 | Martindale et al. | 435/1 |
| 5,118,512 | 6/1992 | O'Leary et al. | 424/549 |
| 5,141,847 | 8/1992 | Sugimachi et al. | 435/1 |
| 5,145,769 | 9/1992 | McNally et al. | 435/1 |
| 5,160,313 | 11/1992 | Carpenter et al. | 600/36 |
| 5,217,860 | 6/1993 | Fahy et al. | 435/1 |
| 5,472,876 | 12/1995 | Fahy | 435/284.1 |

FOREIGN PATENT DOCUMENTS

| | | |
|---|---|---|
| 0 356 367 | 2/1990 | European Pat. Off. . |
| WO 87/01940 | 4/1987 | WIPO . |
| WO 88/05261 | 7/1988 | WIPO . |
| WO 92/05693 | 4/1992 | WIPO . |
| WO 93/00808 | 1/1993 | WIPO . |

OTHER PUBLICATIONS

Adem et al., "Computer Control of a Modified Langendorff Perfusion Apparatus for Organ Preservation Using Cryoprotective Agents," *J. Biomed. Eng.* 3:134–139 (1981).

Adem et al., "Variations in Vascular Resistance of Isolated Rat Hearts During Normothermic and Hypothermic Experiments," *J. Biomed. Eng.* 3(2):128–133 (1981).

Armitage, W.J., "Survival of Corneal Endothelium Following Exposure to a Vitrification Solution," *Cryobiology* 26:318–327 (1989).

Becker et al., "Influence of the PG–Analogues Iloprost, Nalador and Nileprost on Rejection Time and $TXB_2$ content of Murine Tail Skin Allografts," *Biomed. Biochim. Acta 47* (S117–S120) (1988).

Belzer et al., "24–Hour and 72–Hour Preservation of Canine Kidneys," *The Lancet* pp. 536–539 (Sep. 9, 1967).

Belzer et al., "Etiology of Rising Perfusion Pressure in Isolated Organ Perfusion," *Annals of Surgery* 168(3):382–391 (1968).

Belzer et al., "Isolated Perfusion of Whole Organs," in: Organ Perfusion and Preservation (Norman et al., eds.) Appleton–Century–Crofts, New York, NY, pp. 3–12 (1968).

Belzer et al., "Successful Seventeen–Hour Preservation and Transplantation of Human Cadaver Kidney," *The New England Journal of Medicine* 278(11):608–610 (1968).

Belzer et al., "Preservation and Transplantation of Human Cadaver Kidneys: A Two–Year Experience," *Annals of Surgery* 172(3):394–404 (1970).

Bolger et al., "Renal Actions of Prostacyclin," *Nature* 271:467–469 (1978).

Casey et al., "Alteration of Postischemic Renal Pathology by Prostaglandin Infusion," *J. Surgical Res.* 29:1–10 (1980).

Chaudhry et al., "Microcomputer Control Scheme for Organ Cryopreservation," in: Organ Preservation: Present and Future, The Transplantation Society, Churchill College, Cambridge, UK, (Abstract No. P.8) (Apr. 6–9, 1981).

Clark et al., "Evaluation of Belzer and Collins Kidney–Preservation Methods," *The Lancet* pp. 361–363 (1973).

(List continued on next page.)

*Primary Examiner*—Sandy Saucier
*Attorney, Agent, or Firm*—Oliff & Berridge, PLC

[57] ABSTRACT

The invention relates to the field of organ and tissue perfusion. More particularly, the present invention relates to a method for preparing organs, such as the kidney and liver, for cryopreservation through the introduction of vitrifiable concentrations of cryoprotectant into them. To prepare the organ for cryopreservation, the donor human or animal, is treated in the usual manner and may also be treated with iloprost, or other vasodilators, and/or transforming growth factor β1. Alternatively, or additionally, the organ which is to be cryopreserved can be administered iloprost, or other vasodilators, and/or transforming growth factor β1 directly into its artery. The invention also relates to preparing organs for transplantation by a method for the removal of the cryoprotectant therefrom using low (such as raffinose, sucrose, mannitol, etc.), medium (such as agents with intermediate molecular weights of around 600–2,000) and high (such as hydroxyethyl starch) molecular weight agents osmotic buffering agents. The invention is also directed to new post-transplantation treatments such as the use of transforming growth factor β1, N-acetylcysteine and aurothioglucose.

32 Claims, 30 Drawing Sheets

OTHER PUBLICATIONS

Clark et al., "Factors Influencing Renal Cryopreservation. I. Effects of Three Vehicle Solutions and the Permeation Kinetics of Three Cryoprotectants Assessed with Rabbit Cortical Slices," *Cryobiology* 21:260–273 (1984).

Collins et al., "Comparative Evaluation of a New Low Ionic Strength, Hyperkalaemic Flush Solution," in: Organ Preservation: Basic & Applied Aspects (Pegg et al., eds.) MTP Press, Lancaster, UK, pp. 187–189 (1982).

Collins et al., "Studies in Cryoprotection: I. A Simple Method for the Controlled Introduction and Removal of Cryoprotective Agents During Organ Perfusion," *Cryobiology* 21:1–5 (1984).

Collins et al., "Vascular Resistance vs. Perfusate Osmolarity: The Short Term Microvascular Effect of Hypotonic and Hypertonic Perfusion in the Isolated Kidney," *Int. J. Microcirc.: Clin. Exp.* 8:259–273 (1989).

Fahy, G.M., "Activation of Alpha Adrenergic Vasoconstrictor Response in Kidneys Stored at −30° C. for up to 8 Days," *Cryo–Letters* 1:312–317 (1980).

Fahy, G.M., "Analysis of Solution Effects' Injury: Rabbit Renal Cortex Frozen in the Presence of Dimethyl Sulfoxide," *Cryobiology* 17:371–388 (1980).

Fahy, G.M., "Prevention of Toxicity from High Concentrations of Cryoprotective Agents," in: Organ Preservation, Present and Future, The Transplantation Society, Churchill College, Cambridge, England (Abstract No. 44) (Apr. 6–9, 1981).

Fahy, G.M., "Prospects for Vitrification of Whole Organs," *Cryobiology* 18:617 (Abstract No. 20) (1981).

Fahy, G.M., "Prevention of Toxicity from High Concentrations of Cryoprotective Agents," in: Organ Preservation: Basic & Applied Aspects (Pegg et al., eds.), MTP Press Limited, Lancaster, UK, pp. 367–369 (1982).

Fahy, G.M., "Recent Progress Toward Vitrification of Kidneys," *Cryobiology* 19:668–669 (Abstract No. 62) (1982).

Fahy, G.M., "The Effect of Cryoprotectant Concentration on Freezing Damage in Kidney Slices," in: Organ Preservation: Basic and Applied Aspects (Pegg et al., eds.) MTP Press, Lancaster, UK, pp. 385–388 (1982).

Fahy, G.M., "Viability Concepts in Organ Preservation," in Basic Concepts of Organ Procurement, Perfusion, and Preservation for Transplantation, Academic Press, Inc., pp. 121–158 (1982).

Fahy, G.M., "Cryoprotectant Toxicity Neutralizers Reduce Freezing Damage," *Cryo–Letters* 4:309–314 (1983).

Fahy, G.M., "Cryoprotectant Toxicity: Biochemical or Osmotic?" *Cryo–Letters* 5:79–90 (1984).

Fahy, G.M., "Cryoprotectant Toxicity Reduction: Specific or Nonspecific?" *Cryo–Letters* 5:287–294 (1984).

Fahy, G.M., "The Relevance of Cryoprotectant Toxicity to Cryobiology," *Cryobiology* 23:1–13 (1986).

Fahy, G.M., "Vitrification: A New Approach to Organ Cryopreservation," in: Transplantation: Approaches to Graft Rejection, pp. 305–335 (1986).

Fahy, G.M., "Biological Effects of Vitrification and Devitrification," in: The Biophysics of Organ Cryopreservation (Pegg et al., eds.) Plenum Press, pp. 265–297 (1987).

Fahy, G.M., "Vitrification of Multicellular Systems and Whole Organs," *Cryobiology* 24:580–581 (Abstract No. 96) (1987).

Fahy, G.M., "Vitrification," in: Low Temperature Biotechnology: Emerging Applications and Engineering Contributions, The American Society of Mechanical Engineers publication, Book No. G00459, pp. 113–146 (1988).

Fahy, G.M., "Vitrification as an Approach to Organ Cryopreservation: Past, Present and Future, Cryopreservation and Low Temperature Biology," in: Blood Transfusion (Smit–Sibinga et al., eds.) Kluwer Academic, Boston, MA, pp. 255–268 (1990).

Fahy, G.M., "Future Directions in Tissue and Organ Preservation," *Cryobiology* 29:719 (Abstract No. 47) (1992).

Fahy, G.M., "The Role of Inorganic Ions in Tissue Preservation Solutions," *Cryobiology* 29:773 (Abstract No. 189) (1992).

Fahy, G.M., "Organ Perfusion Equipment for the Introduction and Removal of Cryoprotectants," *BioMed. Instrumentation & Tech.* 28(2):87–100 (1994).

Fahy et al., "An Improved Perfusate for Hypothermic Renal Preservation. I. Initial in vitro Optimization Based on Tissue Electrolyte Transport," *Cryobiology* 16:618 (Abstract No. 109) (1979).

Fahy et al., "Cryoprotection of the Mammalian Brain," *Cryobiology* 18:618 (Abstract No. 24) (1981).

Fahy et al., "Prospects for Organ Preservation by Vitrification," in: Organ Preservation Present and Future, The Transplantation Society, Churchill College, Cambridge, England, (Abstract No. 29) (Apr. 6–9, 1981).

Fahy et al., "Vitrification of Aqueous Solutions of Cryoprotectants and Living Tissue Under Pressure," Abstract (published) and 14 page poster (not published), presented at the VII International Biophysics Cong. and III Pan Amer. Biochem. Cong., Mexico City, Mexico, (Aug. 27, 1981).

Fahy et al., "Prospects for Organ Preservation by Vitrification," in: Organ Preservation: Basic and Applied Aspects (Pegg et al., eds.) MTP Press, Lancaster, UK, pp. 399–404 (1982).

Fahy et al., "Vitrification as an Approach to Cryopreservation," *Cryobiology* 20:699 (Abstract No. 5) (1983), 21:407–426 (1984).

Fahy et al., "Histological Cryoprotection of Rat and Rabbit Brains," *Cryo–Letters* 5:33–46 (1984).

Fahy et al., "A Fully Automated System for Treating Organs with Cryoprotective Agents," *Cryobiology* 22:607–608 (Abstract No. 21) (1985).

Fahy et al., Three Slides shown with oral presentation AR16. The slides were not published. (3 pages) (1985).

Fahy et al., "Practical Aspects of Ice–Free Cryopreservation," in: Future Developments in Blood Banking (Smit–Sibinga et al., eds.) Martinus–Nijhoff, Boston, MA, pp. 111–122 (1986).

Fahy et al., "Vitrification Solutions: Molecular and Biological Aspects," *Cryobiology* 23:560 (Abstract No. 41) (1986).

Fahy et al., "Some Emerging Principles Underlying the Physical Properties, Biological Actions, and Utility of Vitrification Solutions," *Cryobiology* 24:196–213 (1987).

Fahy et al., "Cryoprotectant Toxicity and Cryoprotectant Toxicity Reduction: In Search of Molecular Mechanisms," *Cryobiology* 26:537 (Abstract No. 6) (1989).

Fahy et al., "Physical Problems with Vitrification of Large Systems," *Cryobiology* 26:569–570 (Abstract No. 100) (1989).

Fahy et al., "Equipment, Solutions, Perfusion Techniques, and Medications Permitting Survival of Kidneys Perfused with Vitrifiable Media," *Cryobiology* 28:511–512 (Abstract No. 2) (1991).

Farrant, J., "Mechanism of Cell Damage During Freezing and Thawing and Its Prevention," *Nature* 205:1284–1287 (1965).

Fuller et al., "Studies on Cryoprotectant Equilibration in the Intact Rat Liver Using Nuclear Magnetic Resonance Spectroscopy: A Noninvasive Method to Assess Distribution of Dimethyl Sulfoxide in Tissues," *Cryobiology* 26:112–118 (1989).

Guttman et al., "Variation of Cooling Rate and Concentration of Dimethyl Sulfoxide on Rabbit Kidney Function," *Cryobiology* 23:495–499 (1986).

Halasz et al., "Studies in Cryoprotection II: Propylene Glycol and Glycerol," *Cryobiology* 21:144–147 (1984).

Hill et al., "The Renal Haemodynamic and Excretory Actions of Prostacyclin and 6–OXO–PGF$_{1\alpha}$ in Anaesthetized Dogs," *Prostaglandins* 17(1):87–98 (1979).

Hooper et al., "The Use of a Prostacyclin Analog, Iloprost, as an Adjunct to Pulmonary Preservation with Euro–Collins Solution," *Transplantation* 49(3):495–499 (1990).

Isenberg et al., "Prevention of Ischemic Renal Damage with Prostacyclin," *Mount Sinai J. Med.* 49(5):415–417 (1982).

Jacobsen, I.A., "Distribution and Removal of Glycerol by Vascular Albumin Perfusion in Rabbit Kidneys," *Cryobiology* 15:302–311 (1978).

Jacobsen, I.A., "An Introduction to the Problems of Organ Cryopreservation," in: The Biophysics of Organ Cryopreservation (Pegg et al., eds.) Plenum Press, New York, NY, pp. 15–21 (1987).

Jacobsen et al., "Transplantation of Rabbit Kidneys Perfused with Glycerol Solutions at 10° C.," *Cryobiology* 15:18–26 (1978).

Jacobsen et al., "Effect of Cooling and Warming Rate on Glycerolized Rabbit Kidneys," *Cryobiology* 19:668 (Abstract No. 60) (1982).

Jacobsen et al., "Cryopreservation of Organs: A Review," *Cryobiology* 21:377–384 (1984).

Jacobsen et al., "Introduction and Removal of Cryoprotective Agents with Rabbit Kidneys: Assessment by Transplantation," *Cryobiology* 25:285–299 (1988).

Jutte et al., "Cryopreservation of Mouse, Monkey and Human Islets of Langerhans for Transplantation Purposes," *Netherlands J. Surg.* 39:15–18 (1987).

Khirabadi et al., "Comparison of Euro–Collins Solution and RPS–2 as Potential Carriers for Vitrification Solutions Using the Rabbit Renal Autograft Model," *Cryobiology* 26:593–594 (Abstract No. 251) (1989).

Khirabadi et al., "Organ Cryopreservation: Protective Effects of a Prostacylin Analogue (Iloprost) on Nephrotoxic Injuries of Cryoprotective Agents (CPAs) in Rabbits," presented as a poster at the American Red Cross on the afternoon of May 14, 1990, in a conference titled Blood Services Scientific Conference.

Khirabadi et al., "Organ cryopreservation: protective effects of a prostacylin analogue (Iloprost) on nephrotoxic injuries of cryoprotective agents (CPAs) in rabbits," *Cryobiology* 28:597–598 (1991).

Khirabadi et al., "Life Support Function of Rabbit Kidneys cooled to –30° C.," *Cryobiology* 29:721–722 (Abstract No. 52) (1992).

Khirabadi et al., "Life Support Function of Rabbit Kidneys Exposed to Extreme Hydrostatic Pressure," *Cryobiology* 29:722 (Abstract No. 53) (1992).

Khirabadi et al., "Life Support Function of Rabbit Kidneys Perfused with 8 Molar Cryoprotectant," *Cryobiology* 30:612 (Abstract No. 9) (1993).

Khirabadi et al., "Perfusion of Rabbit Kidneys with 8 Molar Cryoprotectant (V52)," *Cryobiology* 30:611–612 (Abstract No. 8) (1993).

Khirabadi et al., "Cryopreservation of the Mammalian Kidney. I. Transplantation of Rabbit Kidneys Perfused with EC and RPS–2 at 2–4° C.," *Cryobiology* 31:10–25 (1994).

Kootstra et al., "A New Device Towards Intermediate Term Kidney Preservation—An Experimental Study," *Scand. J. Urol. Nephrol. 54* (Suppl.):86–89 (1980).

Langkopf et al., "Improvement in the Preservation of Ischemically Impaired Renal Transplants of Pigs by Iloprost," *Prostaglandins Leukotrienes and Medicine* 21:23–28 (1986).

Levin, R.L., "Optimum Methods for the Introduction or Removal of Permeable Cryoprotectants: Perfused Tissues and Organs," *Cryobiology* 18:617–618 (Abstract No. 22) (1981).

Levin, R.L., "The Osmotic Behavior of Perfused Organs," *Cryobiology* 18(6):37 (1981).

MacFarlane et al., "Homogeneous Nucleation and Glass Formation in Cryoprotective Systems at High Pressures," *Cryo–Letters* 2:353–358 (1981).

Mehl et al., "Nucleation and Crystal Growth in a Vitrification Solution Tested for Organ Cryopreservation by Vitrification," *Cryobiology* 29:725 (Abstract No. 61) (1992).

Mundy et al., "Experimental Assessment of Prostacyclin in the Harvesting of Kidneys for Transplantation," *Transplantation* 30(4):251–255 (1980).

Okouchi et al., "Comparison of cryoprotectant toxicities at and below Cv using rat liver slices," *Cryobiology* 30:627 (1993).

Okouchi et al., "Liver Cryopreservation: UW Solution as a Vehicle for Vitrification Solution," *Cryobiology* 30:613 (Abstract No. 12) (1993).

Pegg, D.E., "Banking of Cells, Tissues, and Organs at Low Temperatures," in: Current Trends in Cryobiology (Smith, A.U., ed.) Plenum Press, NY, NY, pp. 153–180 (1970).

Pegg, D.E., "Perfusion of Rabbit Kidneys with Cryoprotective Agents," *Cryobiology* 9:411–419 (1972).

Pegg, D.E., "The Mechanism of Cryoinjury in Glycerol–Treated Rabbit Kidneys," *Cryobiology* 16:618 (Abstract No. 108) (1979).

Pegg, D.E., "Mechanisms of Cryoinjury in Organs," *Cryobiology* 18:617 (Abstract No. 19) (1981).

Pegg et al., "Renal Preservation by Hypothermic Perfusion, 1. The Importance of Pressure Control," *Cryobiology* 10:56–66 (1973).

Pegg et al., "Hypothermic Perfusion of Rabbit Kidneys with Solutions Containing Gelatin Polypeptides," *Transplantation* 24(1):29–38 (1977).

Pegg et al., "Perfusion of Rabbit Kidneys with Glycerol Solutions at 5° C.," *Cryobiology* 14:168–178 (1977).

Pegg et al., "Analysis of the Introduction and Removal of Glycerol in Rabbit Kidneys Using a Krogh Cylinder Model," *Cryobiology* 23:150–160 (1986).

Pegg et al., "Optimization of a Vehicle Solution for the Introduction and Removal of Glycerol with Rabbit Kidneys," *Cryobiology* 23:56–63 (1986).

Pegg et al., "Perfusion of Rabbit Kidneys with Solutions Containing Propane–1,2–diol," *Cryobiology* 24:420–428 (1987).

Perry, R.M., "Mathematical Analysis of Recirculating Perfusion Systems, with Application to Cryonic Suspension," *Cryonics* 9:24–38 (1988).

Rall et al., "Ice–free Cryopreservation of Mouse Embryos at −196° C. by Vitrification," *Nature* 313:573–575 (1985).

Rebmann et al., "Die Verlängerung der Lagerungskonservierung von Schweinenieren auf 72 Stunden durch Einsatz von Iloprost," (see English Summary on p. 616), *Z. Urol. Nephrol.* 78:611–617 (1985).

Rijkmans et al., "Intermediate ex–vivo and in–vitro Perfusion to Prolong Hypothermic Kidney Preservation up to 6 Days," in: Organ Preservation, Basic and Applied Aspects, (Pegg et al., eds.) MTP Press, Lancaster, UK, pp. 267–272 (1982).

Rijkmans et al., "Six–Day Canine Kidney Preservation, Hypothermic Perfusion Combined with Isolated Blood Perfusion," *Transplantation* 37(2):130–134 (1984).

Ruggera et al., "Rapid and Uniform Electromagnetic Heating of Aqueous Cryoprotectant Solutions from Cryogenic Temperatures," *Cryobiology* 26:568 (Abstract No. 96) (1989).

Sadri, F., "Organ Perfusion Systems: An Evaluation Criteria," T.O.P.S. Medical Corporation, Bellevue, WA (8 pages) (1987).

Schabel et al., "Renal Storage Preservation at −5° C. for 7 Days," *Cryobiology* 25:513 (Abstract No. 16) (1988).

Schrör et al., "Dissociation of Antiplatelet Effects from Myocardial Cytoprotective Activity During Acute Myocardial Ischemia in Cats by a New Carbacyclin Derivative," *J. Cardiovascular Pharmacol.* 4(4):554–561 (1982).

Segal et al., "Function of Rabbit Kidneys in vitro at Normothermia Following Equilibration with 3.0 M $Me_2SO$ and Removal by Hypertonic Washout at 10° C.," *Cryobiology* 19:50–60 (1982).

Segal et al., "Kinetics of Permeation and Intracellular Events Associated with $Me_2SO$ Permeation of Rabbit Kidneys During Perfusion at 10° C.," *Cryobiology* 19:41–49 (1982).

Sherwood et al., "Engineering Aspects of Equipment Design for Subzero Organ Preservation," in: Organ Preservation (Pegg, D.E., ed.) pp. 152–174, Churchill, Livingstone, London, UK (1973).

Skaer et al., "Non–Penetrating Polymeric Cryofixatives for Ultrastructural and Analytical Studies of Biological Tissues," *Cryobiology* 15:589–602 (1978).

van Gilst et al., "Improved Functional Recovery of the Isolated Rat Heart After 24 Hours of Hypothermic Arrest with a Stable Prostacyclin Analogue (ZK 36 374)," *J. Mol. Cell. Cardiol.* 15:789–792 (1983).

Van Der Wijk et al., "Successful 96– and 144– Hour Experimental Kidney Preservation: A Combination of Standard Machine Preservation and Newly Developed Normothermic ex Vivo Perfusion," *Cryobiology* 17:473–477 (1980).

Van Der Wijk et al., "Six–Day Kidney Preservation in a Canine Model," *Transplantation* 35(5):408–411 (1983).

Waters Instruments Medical Group, Renal Preservation System, Water Instruments Inc., Rochester, NY, (7 pages) (1982).

Conscience, J.–F., et al., "An Improved Preservation Technique for Cells of Hemopoietic Origin," *Cryobiology* 22(5):495–498 (1985).

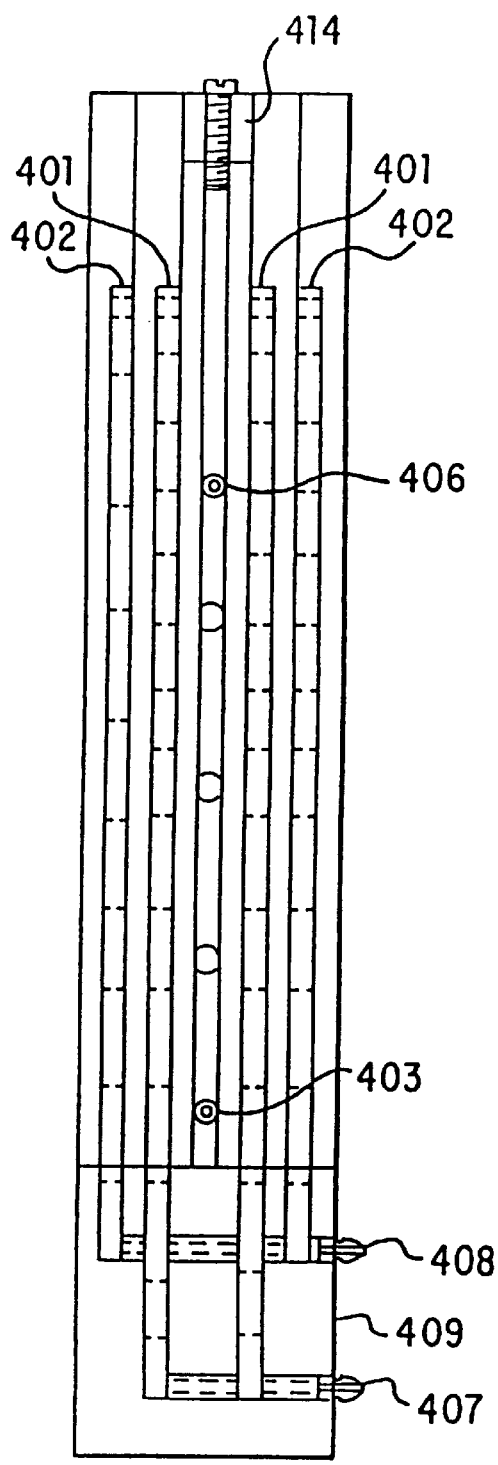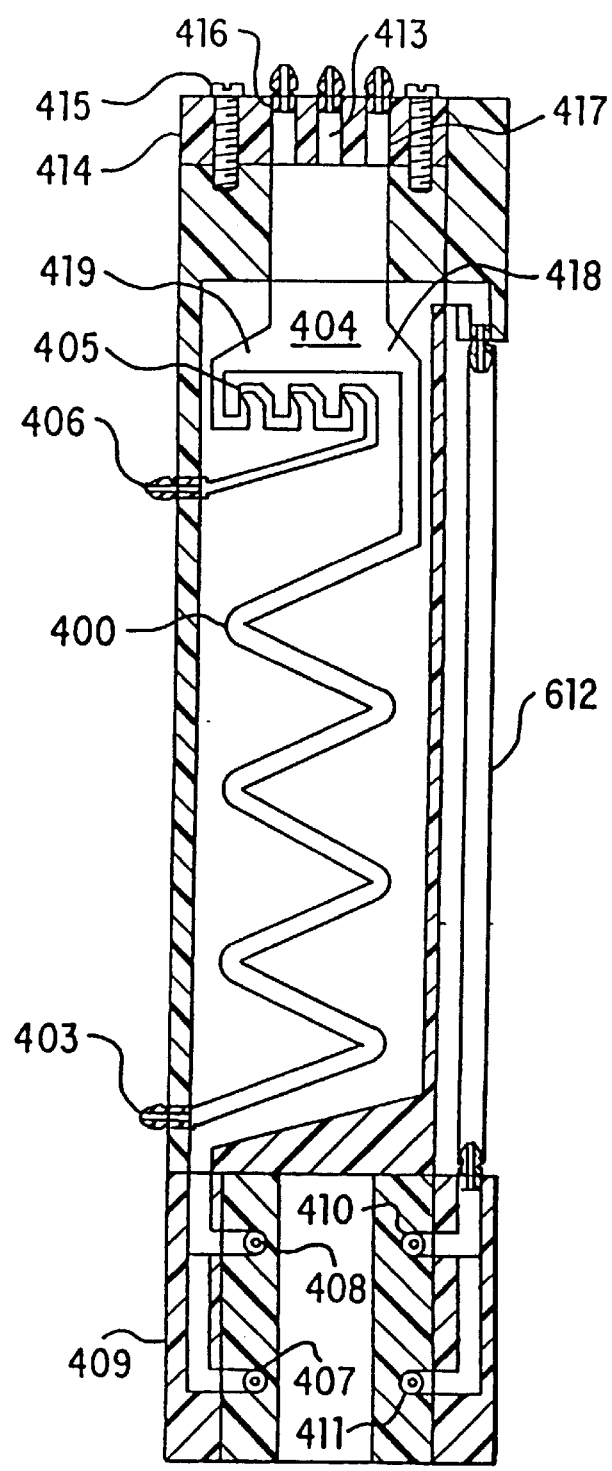
FIG. 4A
FIG. 4B

FIG. 7B

FROM FIGURE 7A

AS CONCENTRATION REACHES A PRESET LEVEL, BEGIN LOWERING ORGAN LOOP TEMPERATURE AT PREDETERMINED RATE.

WHEN TARGET TEMPERATURE IS REACHED, STOP TEMPERATURE DROP.

WHEN FIRST TARGET CONCENTRATION IS REACHED (ANTICIPATING A SMALL ADDITIONAL RISE), TURN OFF GRADIENT PUMP.

KEEP CONCENTRATION STEADY UNTIL ORGAN EQUILIBRATES.

SWITCH TO R2 TO ABRUPTLY RAISE CONCENTRATION TO SECOND TARGET VALUE; AT THE SAME TIME, STOP ALL RECIRCULATION TO R2 (SEND FLUID TO WASTE INSTEAD) TO AVOID CONTAMINATING R2 WITH DILUTE SOLUTION

AS CONCENTRATION RISES IN ORGAN, ADJUST TEMPERATURE CONDITIONING BASED ON ORGAN FLOW SO AS TO ANTICIPATE TEMPERATURE CHANGES, AND ADJUST ORGAN FLOW CONTROL PROCEDURE BASED ON THE DEGREE OF ORGAN EQUILIBRATION SO AS TO ANTICIPATE ANY PRESSURE CHANGES AND THEREBY PRECLUDE THEM.

WHEN REFRACTOMETER LOOP HAS EQUILIBRATED WITH R2, BEGIN RECIRCULATING FROM THIS LOOP TO R2.

AFTER PERFUSING TARGET CONCENTRATION FOR DESIRED TIME, TAKE ONE OF THE FOLLOWING OPTIONS.

FROM FIG.11A

MEANWHILE, IF GRADUAL DRUG ADDITION IS TO BE ACCOMPLISHED USING R1, ACTIVATE GRADIENT FORMER TO APPROPRIATE RATE; RECORD DRUG CONCENTRATION AND/OR MEDIATOR RELEASE FROM ORGAN IN RESPONSE TO DRUG IF DESIRED AND POSSIBLE (E.G. USING DIFFERENTIAL REFRACTOMETER)

OCCASIONALLY RECHECK PRESSURE TRANSDUCER ACCURACY AND UPDATE ITS CALIBRATION ACCORDINGLY

SWITCH TO R2; RECIRCULATION TO R2 CAN CEASE IF A STEP CHANGE IN CALCIUM, DRUG, AUTOCOID, BLOOD, OR SERUM CONCENTRATION FROM ZERO OR BASELINE IS BEING EFFECTED; IF R2'S ROLE IS TO STABILIZE A PREVIOUSLY-ESTABLISHED CONCENTRATION, FLUID RECIRCULATION TO R2 NEED NOT BE INTERRUPTED; IF PROTOCOL INVOLVES TEMPERATURE CHANGES, SUCH AS PERFUSION AT NORMOTHERMIA WITH BLOOD, TEMPERATURE CHANGE IS ALSO IMPOSED AT ABOUT THE SAME TIME [FOR BLOOD PERFUSION, AN AUXILIARY HEAT EXCHANGER IS USED TO WARM THE BLOOD PRIOR TO ITS ENTRY INTO THE CIRCUIT PUMP HEAD, AND THE AUXILIARY FILTER ACCESSED BY S4 AND S5 IS A BLOOD FILTER]

IF APPROPRIATE, RESTORE RECIRCULATION (TO R2) AFTER CONTAMINATING SOLUTION FROM R1 HAS BEEN ELIMINATED FROM THE REST OF THE CIRCUIT; THIS CAN BE DONE FIRST FROM THE REFRACTOMETER LOOP AND SECOND FROM THE ORGAN LOOP TO MINIMIZE BOTH FLUID WASTE AND CONTAMINATION

IF APPROPRIATE, SET TIME OF SWITCH TO R3 AND PROCEED SIMILARY THROUGH R3 AND, IF DESIRED, R4, DEPENDING ON THE DESIGN OF THE EXPERIMENT; FOR SOME EXPERIMENTS, R4 MAY CONTAIN FIXATIVE

AFTER CYCLING THROUGH ALL DESIRED RESERVOIRS THE DESIRED NUMBER OF TIMES, INFORM THE OPERATOR THAT THE PERFUSION IS COMPLETED AND THE ORGAN IS READY TO REMOVE

WHEN PRESSURE FALLS IN RESPONSE TO ORGAN REMOVAL, CLOSE DATA FILES, CAPTURE SCREEN AS AN IMAGE, DUMP SCREEN TO HARD COPY IF DESIRED BY OPERATOR, SET ALL PUMP SPEEDS TO ZERO, PROVIDE ANY FINAL INSTRUCTIONS TO USER, AND TERMINATE PROGRAM

FIG.11B

METHODS FOR REMOVAL OF CRYOPROTECTANT FROM ORGANS PRIOR TO TRANSPLANTATION

CROSS-REFERENCES TO RELATED APPLICATIONS

This application is a division of U.S. patent application Ser. No. 08/292,001, filed Aug. 18, 1994 now U.S. Pat. No. 5,723,282, which is a Continuation in Part (CIP) of U.S. patent application Ser. No. 08/072,754, filed Jun. 7, 1993, abandoned which is a CIP of application Ser. No. 07/725,054, filed on Jul. 8, 1991 (issued on Jun. 8, 1993 as U.S. Pat. No. 5,217,860). This application is also related to U.S. patent application Ser. No. 08/029,432, which was filed on Mar. 10, 1993, now abandoned and is a divisional of Ser. No. 07/725,054, U.S. Pat. No. 5,217,860. This application is also related to U.S. Pat. No. 4,559,298.

RIGHTS OF THE UNITED STATES GOVERNMENT IN THIS INVENTION

This invention was made with United States Government support under National Institutes of Health Grant Nos. GM 1759, BSRG 2507 and RR 05737. The United States Government has certain rights in this invention.

FIELD OF THE INVENTION

This invention relates to the field of organ perfusion. More particularly, it relates to a computer controlled apparatus and method for perfusing isolated animal, including human, organs. Still more particularly, this invention relates to an apparatus and methods for introducing vitrifiable concentrations of cryoprotective agents into isolated organs or tissues in preparation for their cryopreservation and for removing these agents from the organs and tissues after their cryopreservation in preparation for their transplantation into an animal, including into a human.

BACKGROUND OF THE INVENTION

Cryopreservation (that is, preservation at very low temperatures) of organs would allow organ banks to be established for use by transplant surgeons in much the same way that blood banks are used by the medical community today. At the present time, cryopreservation can be approached by freezing an organ or by vitrifying the organ. If an organ is frozen, ice crystals form within the organ which mechanically disrupt its structure and hence damage its ability to function correctly when it is transplanted into a recipient. Vitrification, by contrast, means solidification, as in a glass, without ice crystal formation.

The main difficulty with cryopreservation is that it requires the perfusion of organs with high concentrations of cryoprotective agents (water soluble organic molecules that minimize or prevent freezing injury during cooling to very low temperatures). No fully suitable equipment or method(s) has been developed to date for carrying out this perfusion process. This has prevented the establishment of viable organ banks that could potentially save lives.

Devices and methods for perfusing organs with cryoprotectant have been described in the literature since the early 1970's. See, Pegg, D. E., in *Current Trends in Cryobiology* (A. U. Smith, editor) Plenum Press, New York, N.Y., 1970, pp. 153–180, but particularly pages 175–177; and Pegg, D. E., *Cryobiology* 9:411–419 (1972).

In the apparatus initially described by Pegg, two perfusion circuits operated simultaneously, one with and one without cryoprotectant. Cryoprotectant was introduced and removed by abruptly switching from the cryoprotectant-free circuit to the cryoprotectant-containing circuit, then back again. The pressure was controlled by undescribed techniques, and data was fed into a data logger which provided a paper tape output which was processed by a programmable desk-top Wang calculator. The experimental results were poor. The equipment and technique described were considered inadequate by Pegg and his colleagues, who later modified them considerably.

In 1973, Sherwood et al. (in *Organ Preservation*, D. E. Pegg, ed., Churchill Livingstone, London (1973), pp. 152–174), described four potential perfusion systems, none of which are known to have been built. The first system consisted of a family of reservoirs connected directly to the organ via a multiway valve, changes being made in steps simply by switching from one reservoir to another.

The second system created changes in concentration by metering flow from a diluent reservoir and from a cryoprotectant concentrate reservoir into a mixing chamber and then to the kidney. No separate pump for controlling flow to the kidney was included. Total flow was controlled by the output of the metering pumps used for mixing. A heat exchanger was used before rather than after the filter (thus limiting heat exchanger effectiveness), and there was an absence of most arterial sensing. As will become readily apparent below, the only similarity between this system and the present invention was the use of two concentration sensors, one in the arterial line and one in the venous line of the kidney. Organ flow rate was forced to vary in order to minimize arteriovenous (A-V) concentration differences. The sensing of concentration before and after the kidney in the circuit is analogous to but substantially inferior to the use of a refractometer and a differential refractometer in the present invention. The present inventors' experience has shown that the use of a differential refractometer is necessary for its greater sensitivity. The concept of controlling organ A-V gradient by controlling organ flow is distinctly inferior to the system of the present invention.

The third system described by Sherwood et al. also lacked a kidney perfusion pump, relying on a "backpressure control valve" to recirculate perfusate from the filter in such a way as to maintain the desired perfusion pressure to the kidney. As with the second Sherwood system, the heat exchanger is proximal to the filter and no bubble trap is present. The perfusate reservoir's concentration is controlled by metered addition of cryoprotectant or diluent as in the second Sherwood system, and if flow from the organ is not recirculated, major problems arise in maintaining and controlling perfusate volume and concentration. None of these features is desirable.

The fourth system was noted by Pegg in an appendix to the main paper. In this system, perfusate is drained by gravity directly from the mixing reservoir to the kidney through a heat exchanger, re-entering the reservoir after passing through the kidney. Concentration is sensed also by directly and separately pumping liquid from the reservoir to the refractometer and back.

Modifications and additional details were reported by Pegg et al. (*Cryobiology* 14:168–178 (1977)). The apparatus used one mixing reservoir and one reservoir for adding glycerol concentrate or glycerol-free perfusate to the mixing reservoir to control concentration. The volume of the mixing reservoir was held constant during perfusion, necessitating an exponentially increasing rate of diluent addition during cryoprotectant washout to maintain a linear rate of concentration change. The constant mixing reservoir volume and the presence of only a single delivery reservoir also made it impossible to abruptly change perfusate concentration. All components of the circuit other than the kidney and a pre-kidney heat exchanger were located on a lab bench at ambient temperature, with the reservoir being thermostated at a constant 30°C. The kidney and the heat exchanger were located in a styrofoam box whose internal temperature was not controlled. Despite this lack of control of the air temperature surrounding the kidney, only the arterial temperature but not the venous temperature or even the kidney surface temperature was measured. The use of a styrofoam box also did not allow for perfusion under sterile conditions. The only possible way of measuring organ flow rate was by switching off the effluent recirculation pump and manually recording the time required for a given volume of fluid to accumulate in the effluent reservoir, since there was no perfusion pump which specifically supplied the organ, unlike the present invention. Pressure was controlled, not on the basis of kidney resistance, but on the basis of the combined resistance of the kidney and a manually adjustable bypass valve used to allow rapid circulation of perfusate through the heat exchanger and back to the mixing reservoir. The pressure sensor was located at the arterial cannula, creating a fluid dead space requiring manual cleaning and potentially introducing undesired addition of unmixed dead space fluid into the arterial cannula. Pressure control was achieved by means of a specially-fabricated pressure control unit whose electrical circuit was described in an earlier paper (Pegg et al., Cryobiology 10:56–66 (1973)). Arterial concentration but not venous concentration was measured. No computer control or monitoring was used. Concentration was controlled by feeding the output of the recording refractometer into a "process controller" for comparison to the output of a linear voltage ramp generator and appropriate adjustment of concentrate or diluent flow rate. Glycerol concentrations were measured manually at 5 minute intervals at both the mixing reservoir and the arterial sample port: evidently, the refractometer was not used to send a measurable signal to a recording device. Temperature and flow were recorded manually at 5 minute intervals. Arterial pressure and kidney weight were recorded as pen traces on a strip chart recorder. None of these features is desirable.

Further refinements were reported by Jacobsen et al. (Cryobiology 15:18–26 (1978)). A bubble trap was added, the sample port on the kidney bypass was eliminated (concentration was measured at the distal end of the bypass line instead), and temperature was recorded as a trace on a strip chart recorder rather than manually every 5 minutes. Additionally, these authors reported that bypass concentration lagged reservoir concentration by 5 min (v. 3 min or less for arterial concentration in the present invention) and that terminal cryoprotectant concentration could not be brought to less than 70 mM after adding 5 liters of diluent to the mixing reservoir (v. near-zero terminal concentrations in the present invention using less than 3 liters of diluent and using peak cryoprotectant concentrations approximately twice those of Jacobsen et al., supra).

A variation on the system was also reported the same year by I. A. Jacobsen (Cryobiology 15:302–311 (1978)). Jacobsen measured but did not report air temperatures surrounding the kidney during perfusion. He reduced the mixing reservoir volume to 70 ml, which was a small fraction of the 400 ml total volume of the circuit. No electronic-output refractometer appears to have been used to directly sense glycerol concentration and control addition and washout. Instead, the calculated values of concentrate or diluent flow rate were drawn on paper with India ink and read by a Leeds and Northrup Trendtrak Programmer which then controlled the concentrate/diluent pump. Despite the low circuit volume, the minimum concentration of cryoprotectant which could be achieved was about 100 mM.

Additional alterations of the same system were reported by Armitage et al. (Cryobiology 18:370–377 (1981)). Essentially, the entire perfusion circuit previously used was placed into a refrigerated cabinet. Instead of a voltage ramp controller, a cam-follower was used. Again, however, it was necessary to calculate the required rates of addition of glycerol or diluent using theoretical equations in order to cut the cam properly, an approach which may introduce errors in the actual achievement of the desired concentration-time histories. Finally, a modification was made in which an additional reservoir was added to the circuit. This reservoir was apparently accessed by manual stopcocks (the mode of switching to and from this reservoir was not clearly explained), and use of the new reservoir was at the expense of being able to filter the perfusate or send it through a bubble trap. The new reservoir was not used to change cryoprotectant concentration; rather, it was used to change the ionic composition of the medium after the cryoprotectant had been added. The volume of the mixing reservoir was set at 500 ml, allowing a final cryoprotectant concentration of 40 mM to be achieved.

To the best of the inventors'knowledge, the devices and methods described above represent the current state of the art of cryoprotectant perfusion as practiced by others.

An approach to organ preservation at cryogenic temperatures previously described by one of the Applicants involved vitrifying rather than freezing organs during cooling (see, for example, Fahy et al., Cryobiology 21:407–426 (1984); and U.S. Pat. No. 4,559,298). "Vitrification" means solidification without freezing and is a form of cryopreservation. Vitrification can be brought about in living systems, such as isolated human or other animal organs, by replacing large fractions of the water in these systems with cryoprotective agents (also known as cryoprotectants) whose presence inhibits crystallization of water (i.e., ice formation) when the system or organ is cooled. Vitrification typically requires concentrations greater than 6 molar (M) cryoprotectant. However, using known techniques, it has not been possible to use sufficiently high cryoprotectant concentrations to vitrify an organ without killing it. The limiting concentration for organ survival was typically just over 4M.

One type of damage caused by cryoprotectants is osmotic damage. Cryobiologists learned of the osmotic effects of cryoprotectants in the 1950's and of the necessity of controlling these effects so as to prevent unnecessary damage during the addition and removal of cryoprotectants to isolated cells and tissues. Similar lessons were learned when cryobiologists moved on to studies of whole organ perfusion with cryoprotectants. Attention to the principles of osmosis were essential to induce tolerance to cryoprotectant addition to organs. Despite efforts to control the deleterious osmotic effects of cryoprotectants, limits of tolerance to cryoprotectants are still observed. There appear to be genuine, inherent toxic effects of cryoprotectants that are independent of the transient osmotic effects of these chemical agents.

Studies by the present inventors and others have examined methods of controlling the non-osmotic, inherent toxicity of cryoprotective agents. The results indicate that several techniques can be effective alone and in combination. These include (a) exposure to the highest concentrations at reduced temperatures; (b) the use of specific combinations of cryoprotectants whose effects cancel out each other's toxicities; (c) exposure to cryoprotectants in vehicle solutions that are optimized for those particular cryoprotectants; (d) the use of non-penetrating agents that can substitute for a portion of the penetrating agent otherwise needed, thus sparing the cellular interior from exposure to additional intracellular agent; and (e) minimization of the time spent within the concentration range of rapid time-dependent toxicity. Means by which these principles could be applied to whole organs so as to permit them to be treated with vitrifiable solutions without perishing, however, have not been clear or available.

Some of these techniques are in potential conflict with the need to control osmotic forces. For example, reduced temperatures also reduce the influx and efflux rate of cryoprotectants, thereby prolonging and intensifying their osmotic effects. Similarly, minimizing exposure time to cryoprotectants maximizes their potential osmotic effects. Thus, there must be a balance reached between the control of osmotic damage and the control of toxicity. Adequate means for obtaining this balance have not been described in the literature. In some cases, intensifying the osmotic effects of cryoprotectants by minimizing exposure times to these agents can be beneficial and complementary to the reduced toxicity that results, but safe means for achieving this in whole organs have not been described.

Organ preservation at cryogenic temperatures would permit the reduction of the wastage of valuable human organs and would facilitate better matching of donor and recipient, a factor which continues to be important despite the many recent advances in controlling rejection (see, Takiff et al., *Transplantation* 47:102–105 (1989); Gilks et al., *Transplantation* 43:669–674 (1987)). Furthermore, most techniques now being explored for inducing recipient immunological tolerance of a specific donor organ would be facilitated by the availability of more time for recipient preparation.

One major limitation in organ cryopreservation studies has been the lack of suitable equipment for controlling perfusion parameters such as cryoprotectant concentration-time history, pressure, and temperature. Previously described standard perfusion machines are not designed for this application and are unable to meet the requirements addressed here. Patented techniques heretofore known are described in:

U.S. Pat. No. 3,753,865 to Belzer et al.;
U.S. Pat. No. 3,772,153 to De Roissart et al.;
U.S. Pat. No. 3,843,455 to Bier, M.
U.S. Pat. No. 3,892,628 to Thorne et al.;
U.S. Pat. No. 3,914,954 to Doerig, R. K.;
U.S. Pat. No. 3,995,444 to Clark et al.;
U.S. Pat. No. 4,629,686 to Gruenberg, M. L.; and
U.S. Pat. No. 4,837,390 to Reneau, R. P.

Equipment described for cryopreservation applications in the past has permitted only relatively simple experimental protocols to be carried out, and has often been awkward to use. Only Adem et al. have reported using a computer for organ perfusion with cryoprotectant (see, for example, *J. Biomed. Engineering* 3:134–139 (1981)). However, their specific design has several major flaws that limit its utility.

The present invention overcomes substantially all of the deficiencies of known apparatus and methods.

SUMMARY OF THE INVENTION

In one embodiment, the present invention is directed to a computer-controlled apparatus and methods for perfusing a human or other animal organ, such as a kidney, liver, heart, etc., with a perfusate, and may include preparing the organ for such perfusion. The perfusion of the organ may be done for any one of a number of reasons including, but not limited to, for example: to prepare the organ for cryopreservation; to prepare the organ for transplantation after its cryopreservation; to preserve it by conventional means above 0°C.; to keep it alive temporarily at high temperatures to study its physiology; to test the organ's viability; to attempt resuscitation of the organ; and to fix the organ for structural studies. The apparatus and methods may also be used to superfuse an organ or tissue slice. In another embodiment, this invention is directed to the treatment of the donor aninal and/or the about-to-be donated organ with iloprost and/or other drugs to prepare it for perfusion. In another embodiment, this invention is directed to an apparatus and method which is used to prepare the organ for cryopreservation, such as by vitrification. In another embodiment, this invention is directed to an apparatus and methods for preparing an organ for transplantation into an appropriate host after its cryopreservation.

In one embodiment, this invention is directed to a method of preparing a biological organ for cryopreservation, comprising the steps of:

(a) perfusing the organ with gradually increasing concentrations of cryoprotectant solution to a first predetermined concentration while concurrently reducing the temperature of the organ;

(b) maintaining the concentration of the cryoprotectant for a sufficient time to permit the approximate osmotic equilibration of the organ to occur; and (c) increasing the cryoprotectant concentration of the solution to a higher second predetermined concentration and maintaining the cryoprotectant concentration of the solution at the second concentration for a time sufficient to permit the approximate osmotic equilibration of the organ to occur.

The organ is then removed from the perfusion apparatus and is cryopreserved using an appropriate method or is further prepared for cryopreservation.

After cryopreservation the organ is warmed in an apparatus which is not the apparatus of this invention.

In preparation for the organ's transplantation into a recipient, the organ is then reattached to the perfusion apparatus of this invention.

In another embodiment, this invention is directed to a method of preparing an organ for transplantation after its cryopreservation and subsequent warming, comprising:

(a) warming the organ to a temperature which permits reperfusion of the organ, wherein damage to the organ is minimized;

(b) perfusing the organ with a non-vitrifiable concentration of cryoprotectant for a time sufficient to permit the approximate osmotic equilibration of the organ to occur; and (c) perfusing substantially all of the cryoprotectant out of the organ while concurrently increasing the temperature of the organ to render the organ suitable for transplantation.

In another embodiment, this invention is directed to a method of preparing an organ for transplantation further comprising perfusing the organ with a reduced concentration of cryoprotectant in combination with: a low molecular weight (LMW) "nonpenetrating" osmotic buffering agent (OBA); or a high molecular weight (HMW) "nonpenetrating" OBA; or a combination of LMW and HMW OBAs which are added and removed in an orchestrated fashion which is appropriate for, and may vary from, organ to organ. In the case of the liver, osmotic buffers (OB) do not have to be used at all. In the case of most other organs, the organ is perfused with the appropriate cryoprotectant solution containing a first OBA concentration for a time sufficient to permit approximate osmotic equilibration of the organ to occur. Substantially all of the cryoprotectant is then washed out (to a final cryoprotectant concentration of less than 200 millimolar) while decreasing the concentration of the OBA to a second, nonzero level substantially below the first buffering agent concentration level and while concurrently increasing the temperature of the organ. Finally, the organ is perfused to remove the OBA sufficiently to render the organ suitable for transplantation.

Exemplifications include the rabbit kidney, the rat liver, and the human kidney.

The apparatus of the invention comprises a computer operated perfusion circuit containing a plurality of fluid reservoirs, a means for raising and lowering concentrations and an organ container. A first fluid flow path is defined as a loop from the plurality of reservoirs to necessary sensors and temperature conditioning means and back to the plurality of reservoirs. The reservoirs are selectively connectable to the first fluid flow path. Pump means are interposed in a second fluid flow path for pumping fluid from the first fluid flow path to a second fluid flow path. The organ container is located in this second fluid flow path. Pump means may also be included in the second fluid flow path for pumping fluid from the organ container to one or more of the reservoirs or to waste. One or more sensors are interposed in the fluid flow paths for sensing at least one of the concentration, concentration differential, temperature, pressure, and pH of the fluid flowing in the first and/or second fluid flow paths. Measuring means are interposed in the first and second fluid flow paths for measuring concentration and temperature differences between the upstream and downstream sides, in the fluid flow direction, of the organ container. The sensor(s) and the measuring means are connected to a programmable computer for providing a continuous information stream from the sensor(s) to the computer. Finally, the computer is coupled to the selection means and the pump means to continuously selectively control (a) the flow of fluid from each of the reservoirs individually to the fluid flow paths, (b) the flow of fluid from each of the fluid flow paths individually to each of the reservoirs, and (c) at least one of the concentration, temperature, pressure and pH of the fluid flowing in the first and/or second fluid flow path, in accordance with a predetermined computer program without substantial operator intervention.

Additional features of the apparatus of this invention may include a heat exchanger interposed in the first fluid flow path for conditioning the temperature of fluid flowing in this fluid flow path. A second heat exchanger may be interposed in the second fluid flow path for conditioning the temperature of fluid flowing in the second fluid flow path.

In describing the apparatus and methods of this invention, many of the various aspects of the same have been numbered. This numbering has been done to create a conceptual organization and structure for this application. This numbering should not be interpreted to necessarily mean or imply that the particular steps in this invention must be performed in the sequences in which they are presented.

FEATURES AND ADVANTAGES OF THE INVENTION

This invention has a multitude of features and advantages, among the most important of which are the following.

1. It permits control of the concentration of cryoprotectant or any other fluid or drug in the perfusate of an organ according to a wide variety of predetermined concentration-time histories, more or less independently of the flow rate of perfusate through the organ, with provision for simultaneously varying the concentrations of other drugs or osmotic agents. Step changes in concentration are possible, and it is possible to bring concentrations effectively to zero.

2. It provides for in-line sensing of concentration, pH, perfusate temperature, and other parameters so as to avoid the need for sensors in the perfusate reservoirs and for manual measurements.

3. It permits minimizing differences between the concentration of cryoprotectant monitored and the concentration of cryoprotectant in the perfusate reservoirs by minimizing the time required for perfusate to travel from the reservoirs to the perfusate sensors and back to the reservoirs.

4. It permits minimizing differences between the concentration of cryoprotectant monitored and the concentration of cryoprotectant actually perfused into the organ by minimizing the time required for the perfusate to travel from the main fluid circuit to the perfused organ (or superfused tissue).

5. It permits monitoring of the arteriovenous difference in cryoprotectant concentration across the organ as an index of the degree of, or opportunity for, organ equilibration with cryoprotectant.

6. It permits control of the temperature of the organ essentially independently of the flow of perfusate through the organ, and permits varying this temperature at will.

7. It permits control of the perfusion pressure, either keeping it fixed or changing it as desired, and, if desired, minimizing pulsation.

8. It protects against perfusion of unmixed solution, air bubbles, particulates, or pathogens into the organ, and avoids inaccessible fluid dead spaces.

9. It interfaces with a computer to control the perfusions, to provide real-time monitoring, display, processing, and recording of the data, to calibrate the sensors and pumps, and to direct the cleaning, disinfection, and priming of the perfusion circuit and to instruct and alert the operator, when necessary.

10. It is readily capable of perfusing and cryoprotecting organs of widely varying size and perfusion requirements, e.g., anything from a rat heart to a human liver, and is capable of tissue or cell culture superfusion as well.

BRIEF DESCRIPTION OF THE FIGURES

FIG. 1 (comprising FIGS. 1A and 1B).

FIGS. 4A–C show left, front, and right side views, respectively, of the Heat Exchanger/Bubble Trap/Mixer (HBM) used in this invention.

Ph5 means phase 5;

epH6 and 7 mean the end of phases 6 and 7, respectively;

Ph5:250 means that the concentration of LMW OBA during phase 5 was 250 millimolar;

ePH6:50 and ePH7:0 mean that the concentrations of LMW OBA at the end of phases 6 and 7 were 50 and 0 millimolar, respectively;

Veh. means vehicle.;

EC means Eurocollins solution;

CPA means cryoprotectant agent;

Numbers 1 to 7 within circles designate the 7 phases of the experiment referred to later;

P/10 means pressure divided by 10;

M means the measurement molar concentration;

M means the forget molar concentration; and

F means flow in ml/min.

Figure 6:
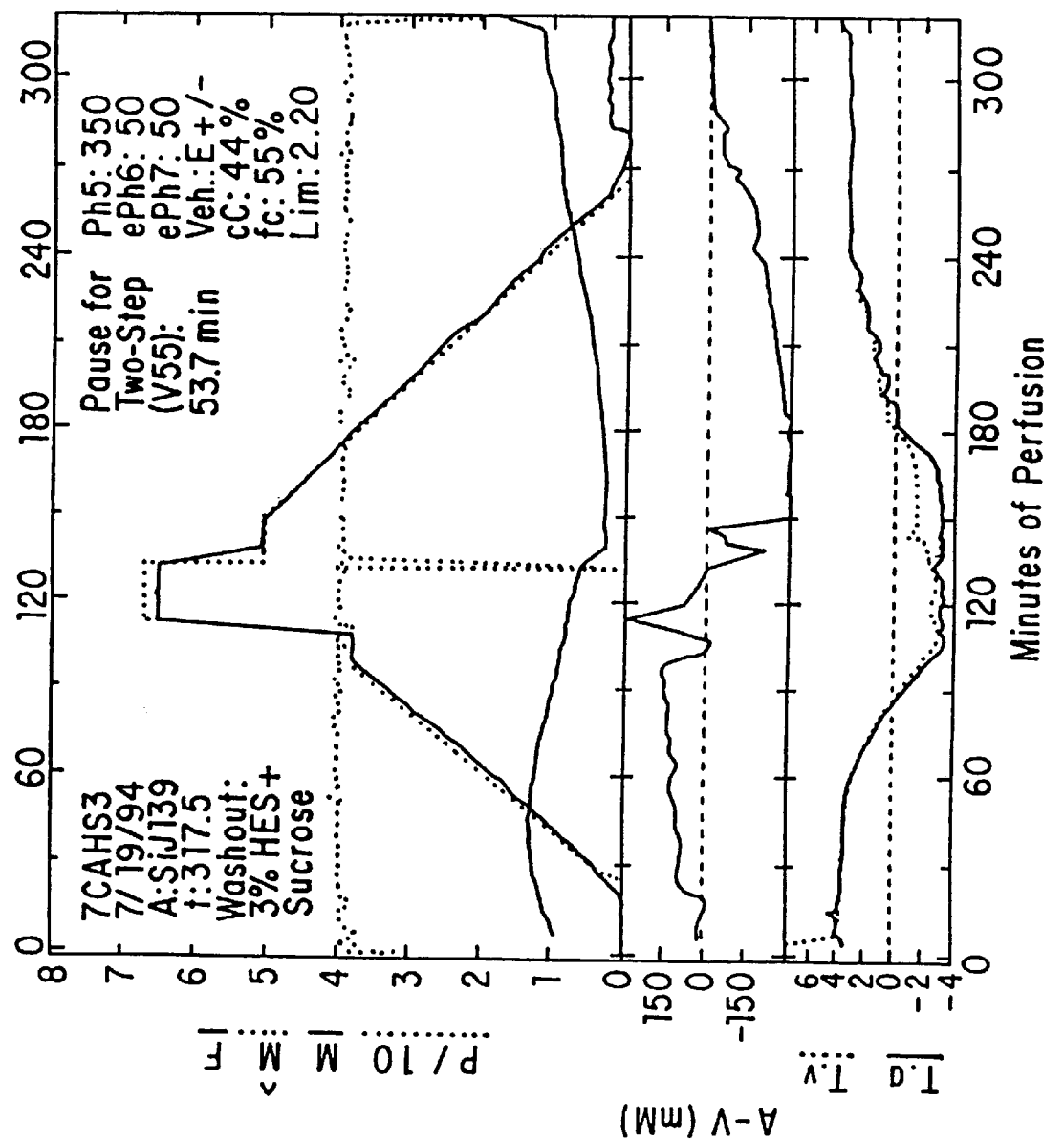
Figure 7A:
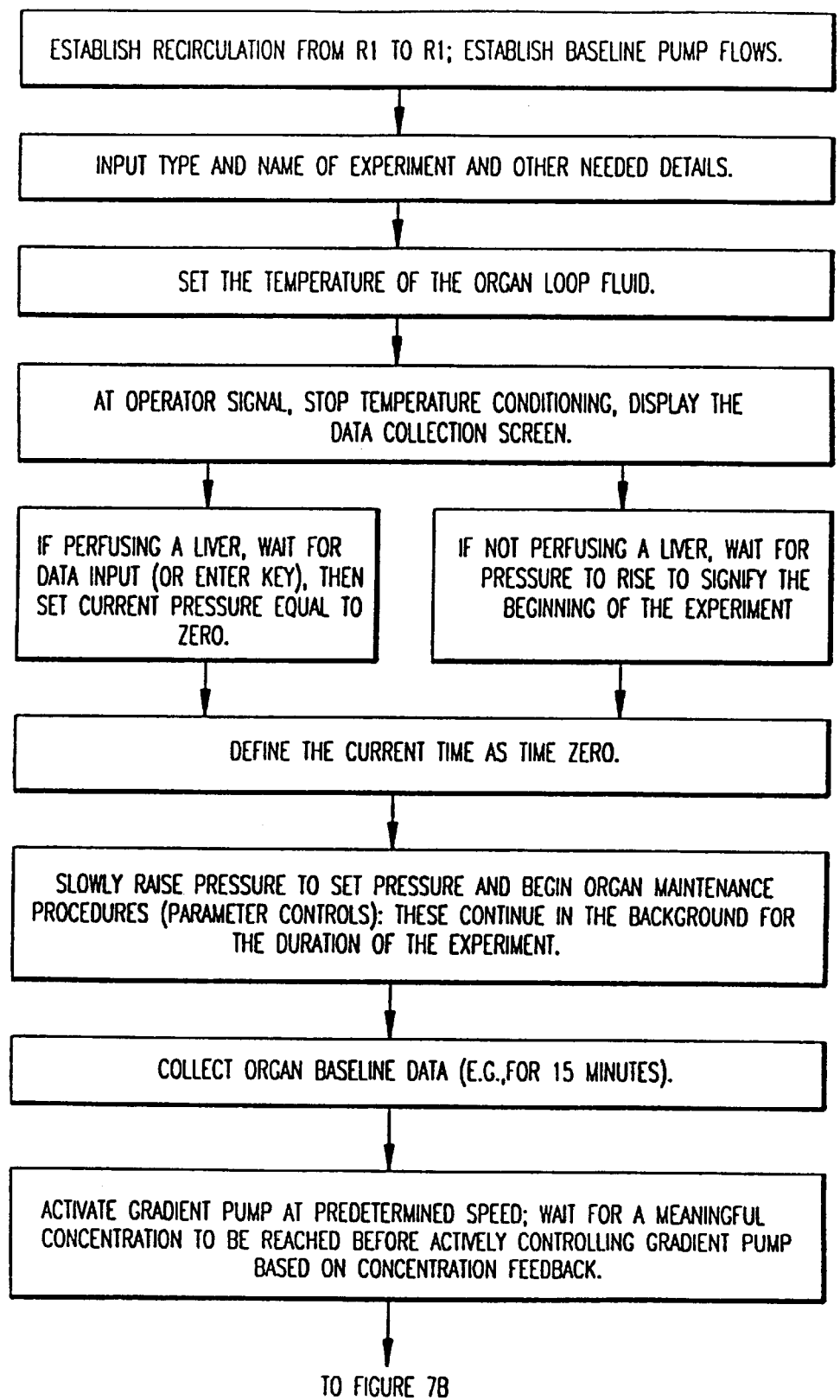
Figure 7C:
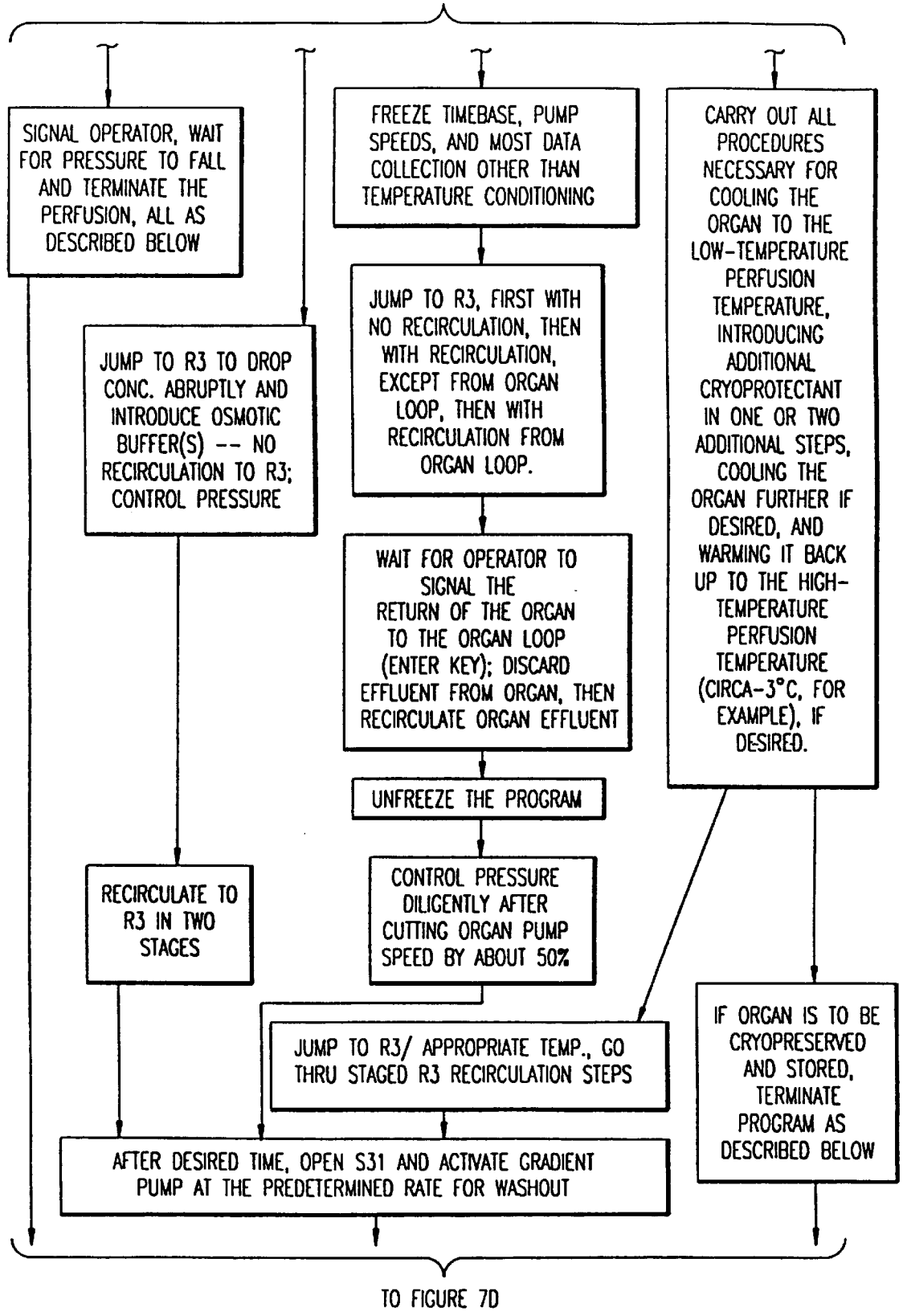
Figure 7D:
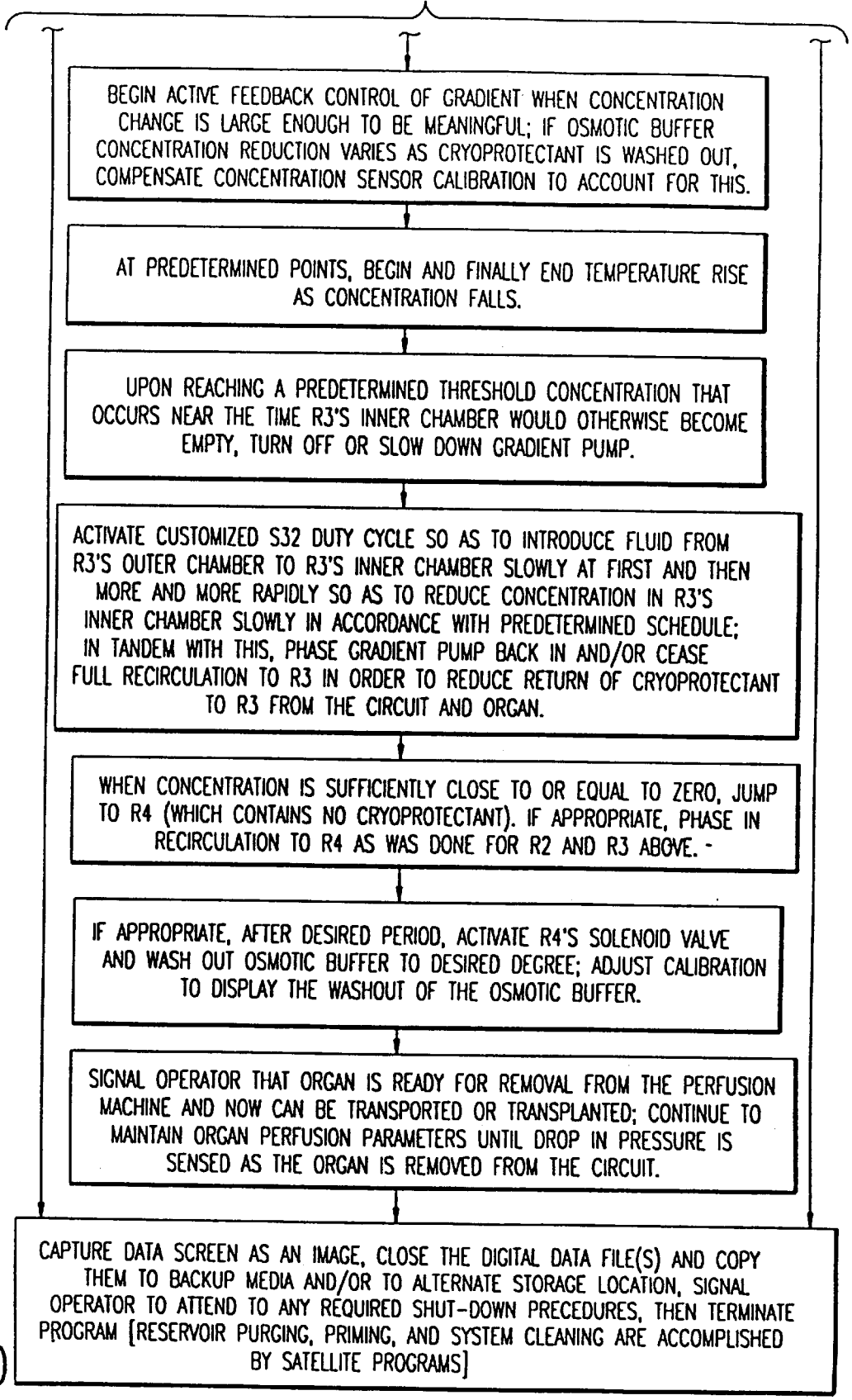

FIG. 6 shows the part of the protocol for the two-step introduction of fully concentrated vitrification solution that was carried out inside the standard perfusion machine.

FIGS. 7A–7D comprise a flow chart of activities for organ cryoprotectant perfusion.

Figure 8:
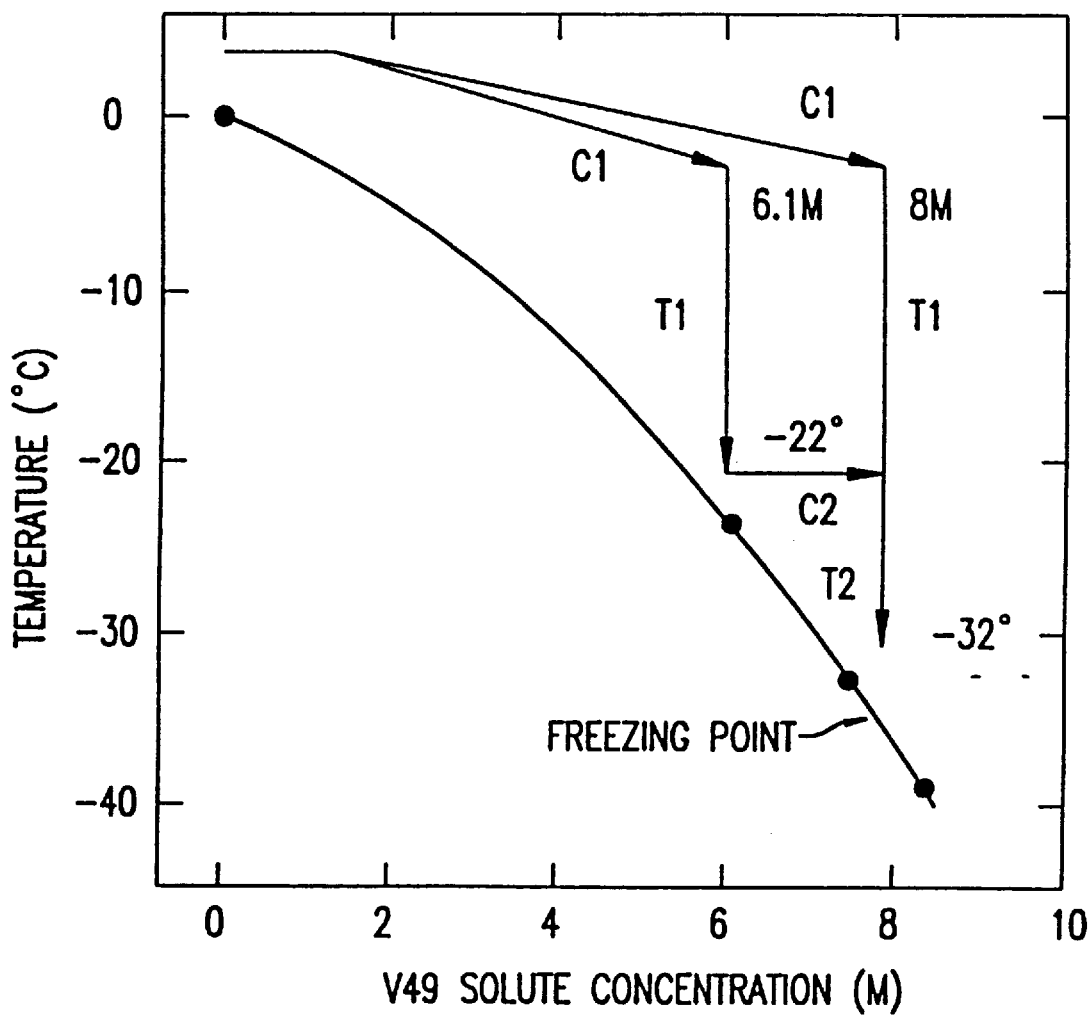

FIG. 8 is a schematic diagram of the details of the two-step cooling technique for introducing high concentrations of cryoprotectants.

Figure 9:
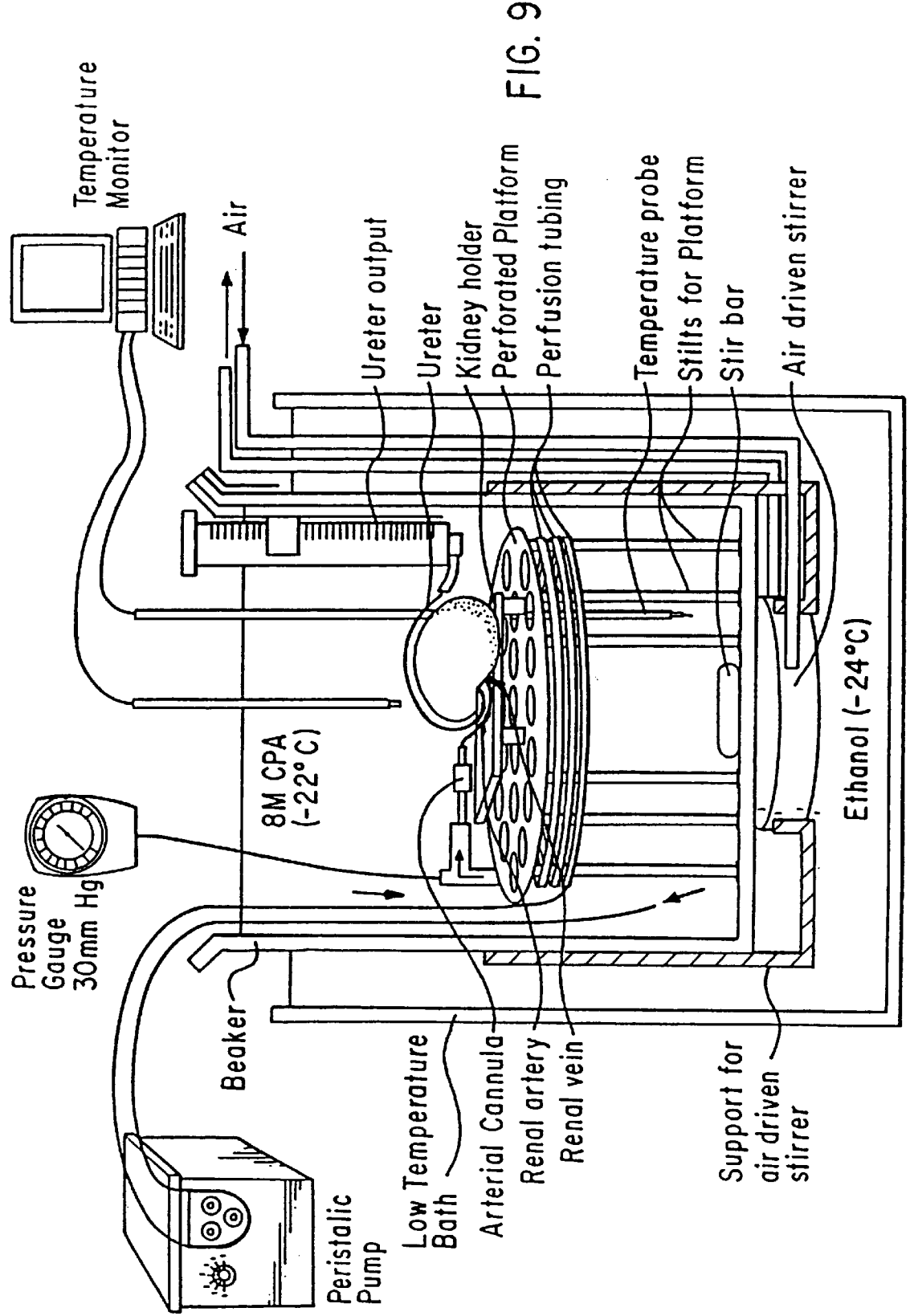

FIG. 9 shows an apparatus to perfuse kidneys with vitrification solutions outside of the standard perfusion machine and at temperatures in the vicinity of −20° to −30° C.

Figure 10:
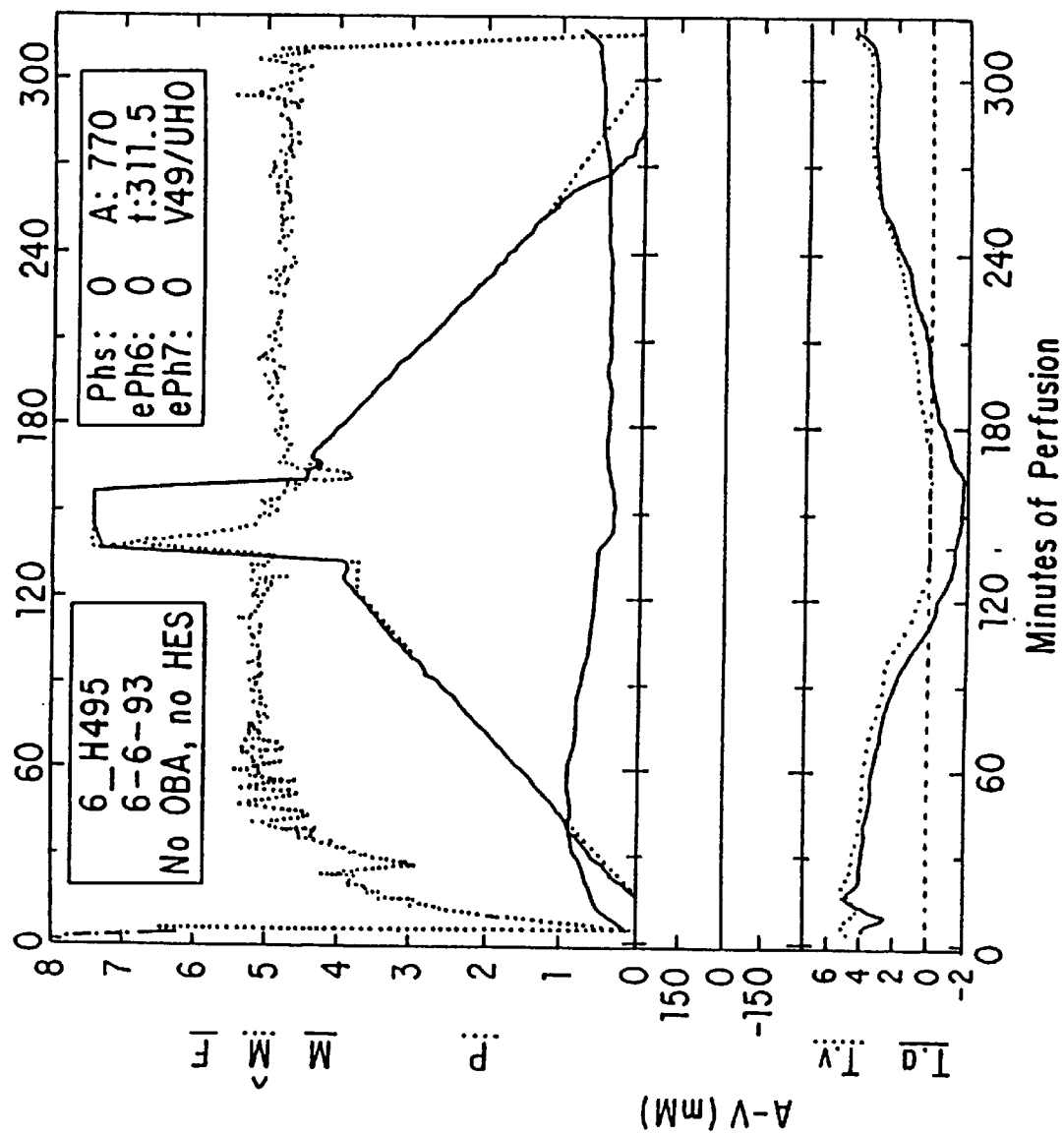

FIG. 10 show a typical rat liver perfusion protocol in which neither HES nor LMW OBAs were used.

Figure 11A:
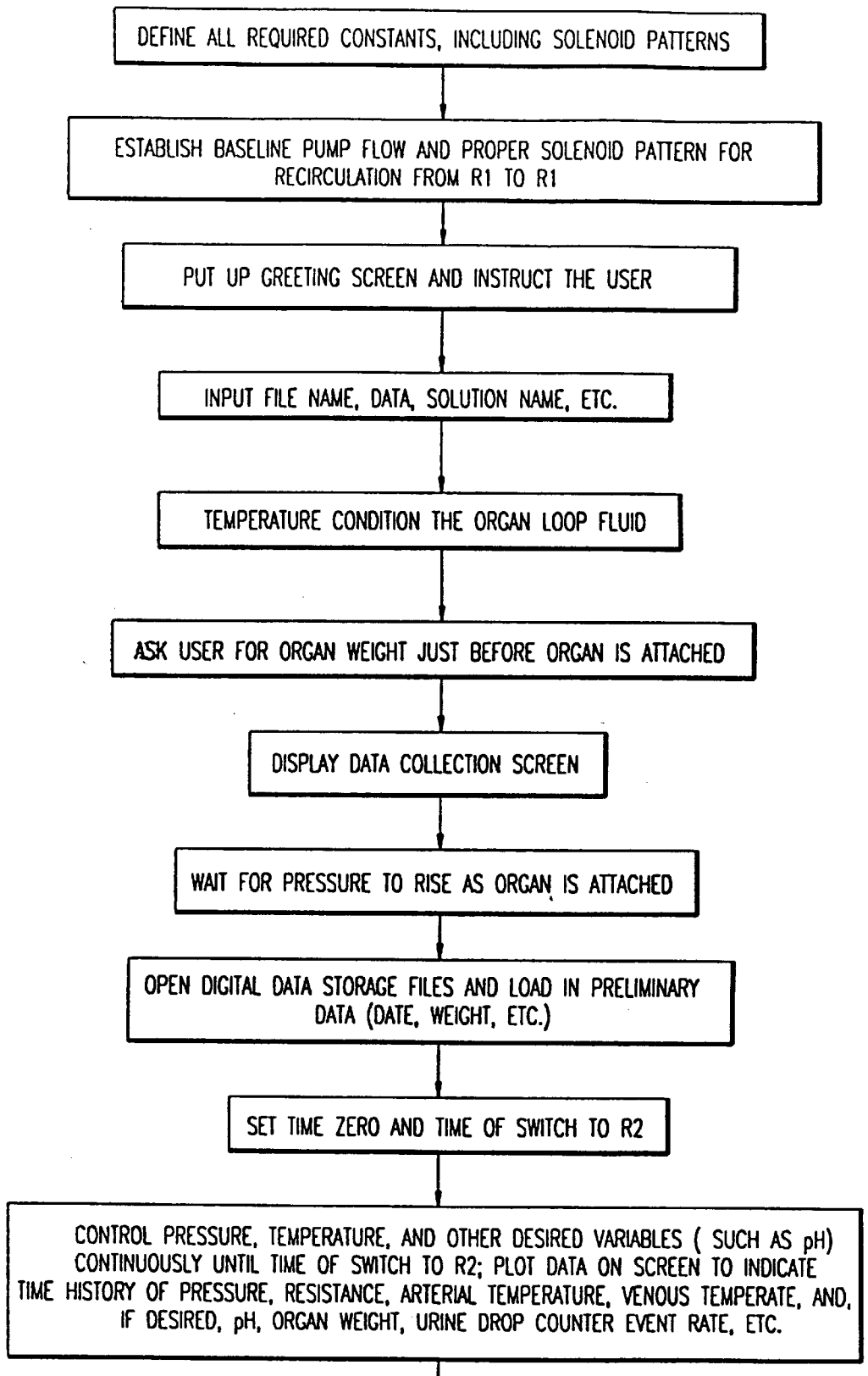

FIG. 11A and 11B comprise a flow chart of the procedure for non-cryoprotectant perfusions.

Figure 12:
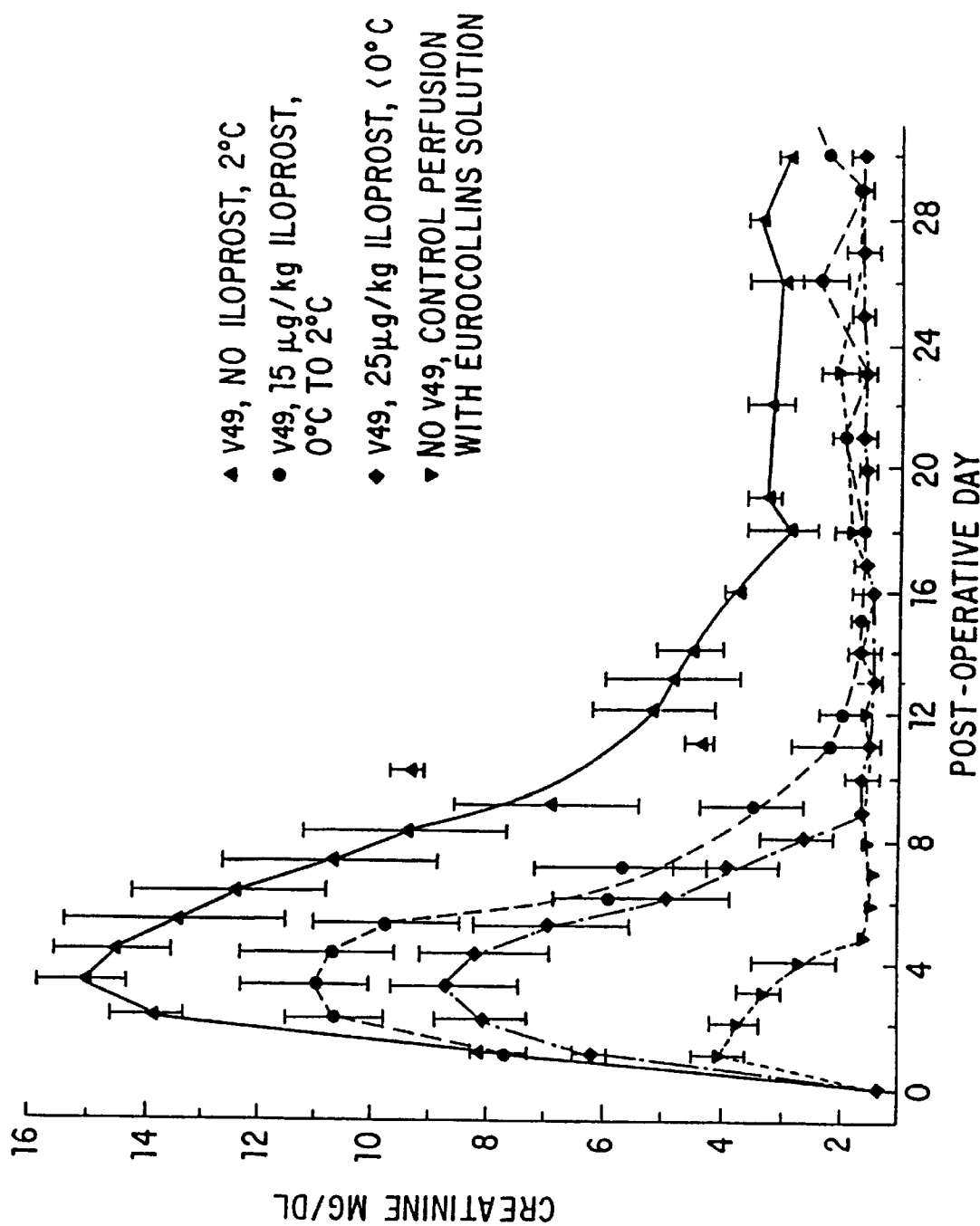

FIG. 12 shows the ability of rabbit kidneys transplanted after perfusion with the vitrifiable solution known as V49 to function as measured by their control of serum creatinine.

Figure 13:
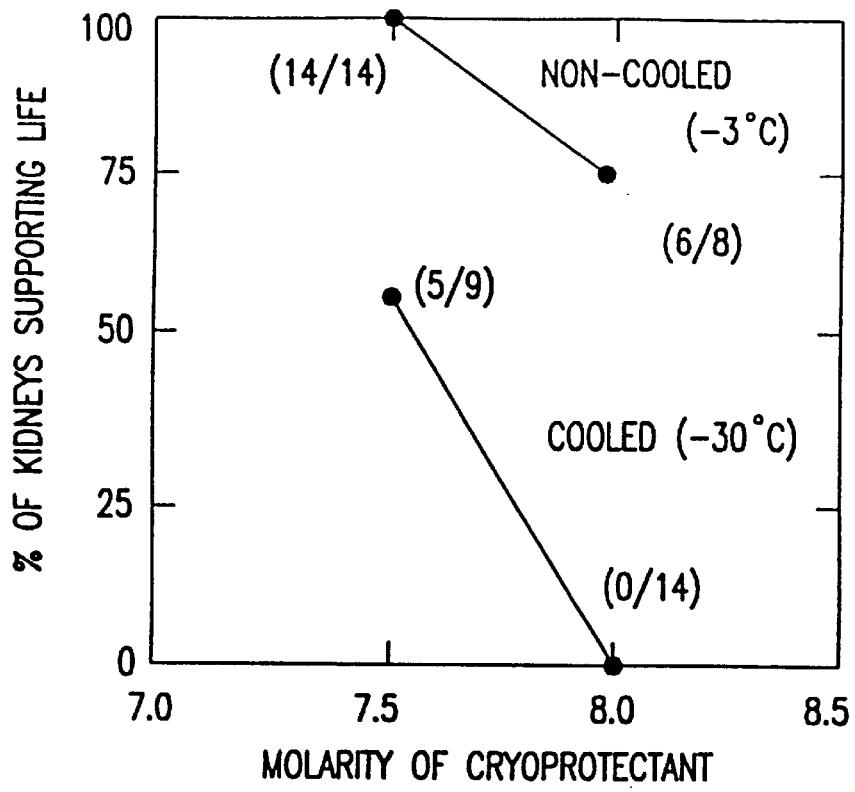

FIG. 13 shows the effect of cooling to −30° C. on rabbit kidneys previously perfused with 7.5M or 8M cyroprotective agents, in comparison to the results for the non-cooled kidneys exposed to −3° C.

Figure 14:
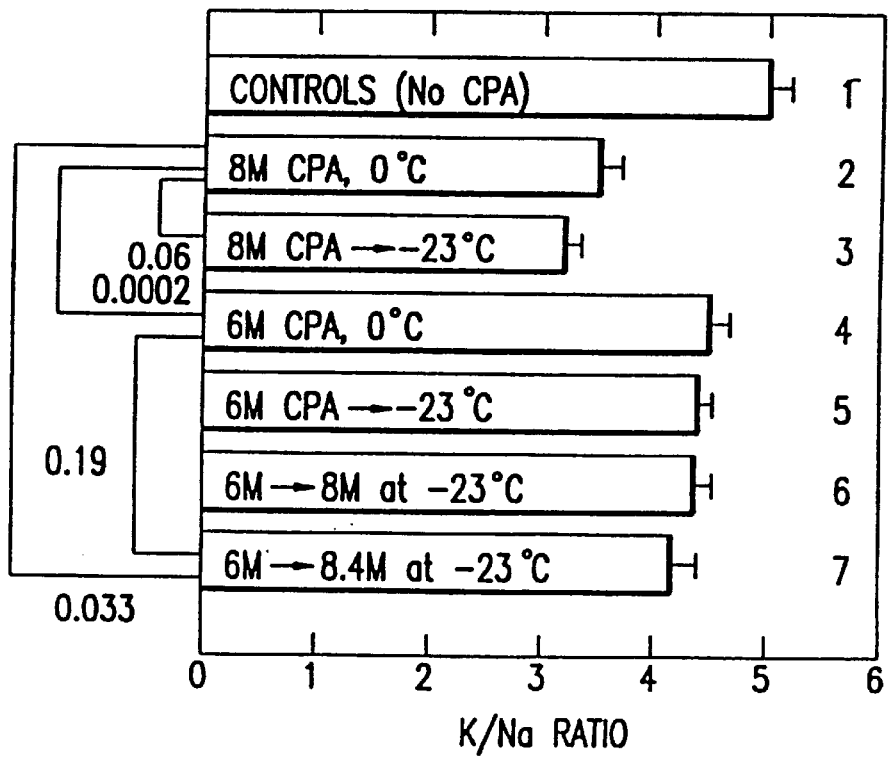

FIG. 14 shows the results of exposing rabbit kidney slices to high concentrations of cryoprotectant after rather than prior to cooling to −23° C., demonstrating that both the cooling injury and the toxicity associated with high concentrations are prevented by cooling initially in a low (6.1M) concentration.

Figure 15B:
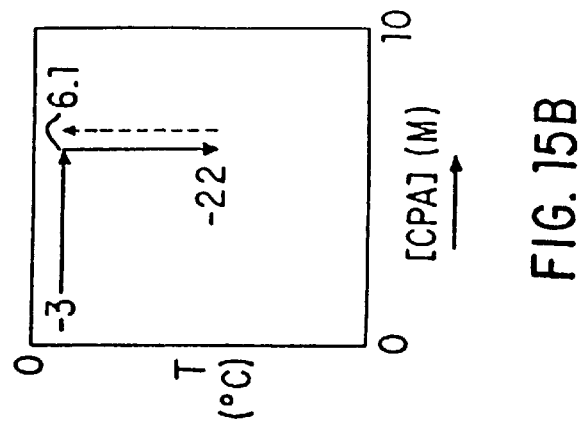
Figure 15A:
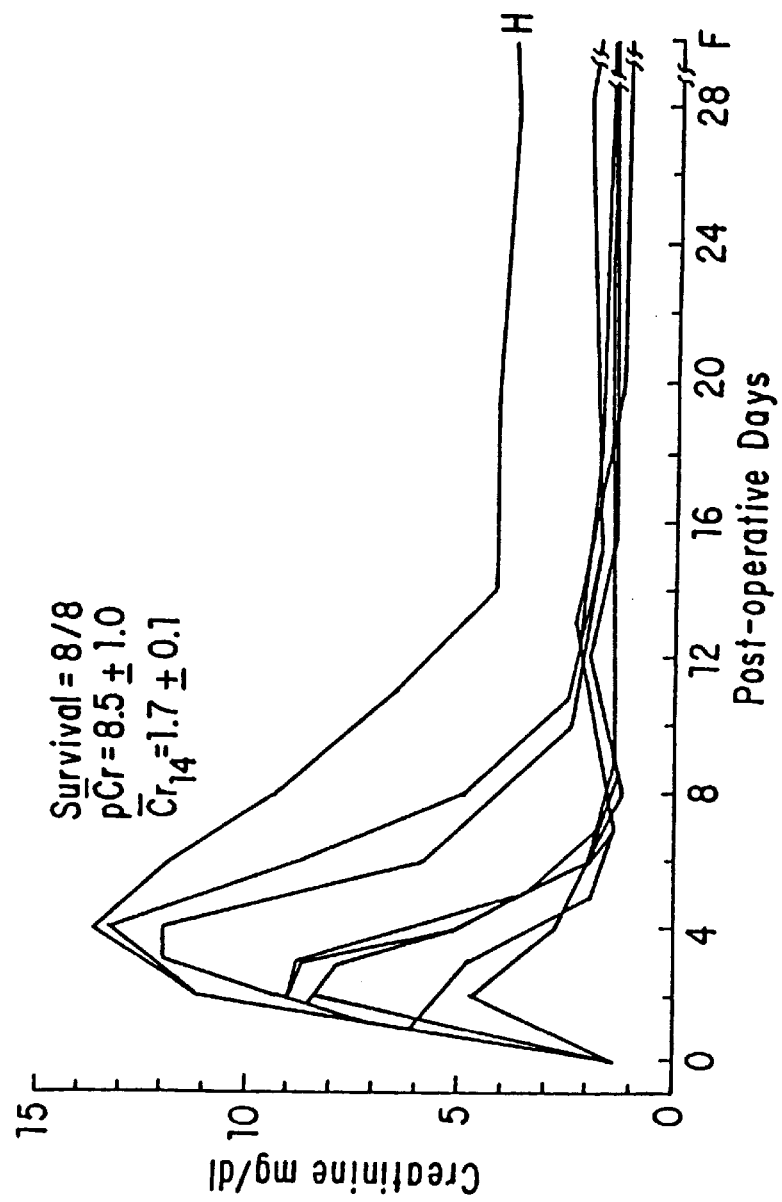

FIG. 15 (comprising FIGS. 15A and 15B) shows that cooling injury is also successfully avoided in the intact kidney at 6.1M croprotectant (100% survival, excellent final creatinine levels), proving the hypothesis that cooling injury is abolished at low concentrations.

Figure 16B:
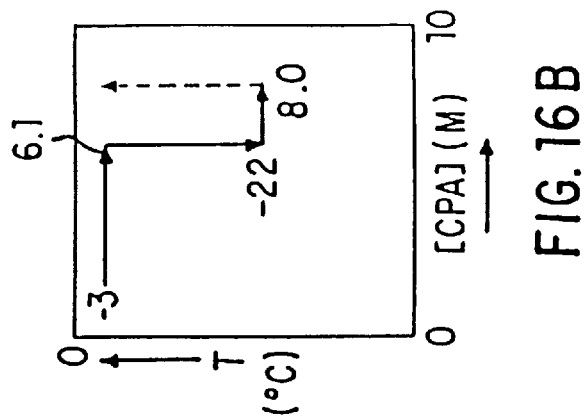
Figure 16A:
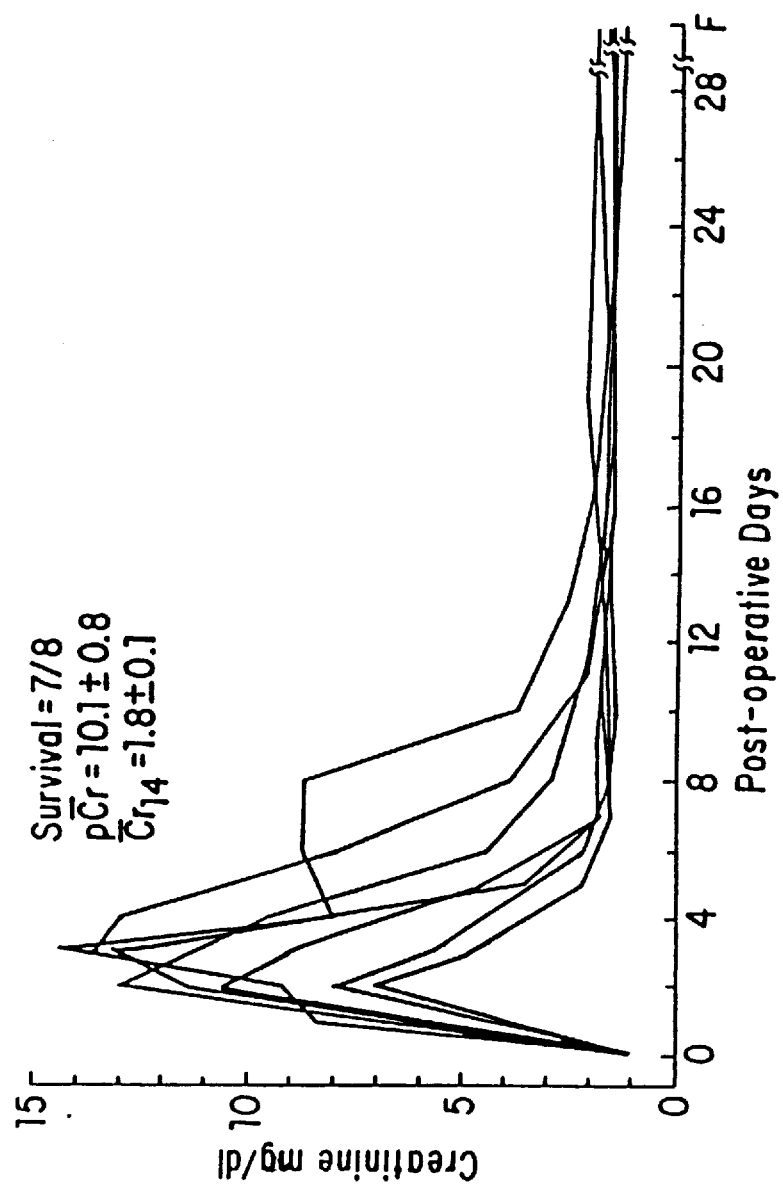

FIG. 16 (comprising FIGS. 16A and 16B) shows the feasibility of the two-step approach for introducing 8M cryoprotectant at −22° C.; the survival rate was 7/8 and the creatinine levels after two weeks were excellent and identical to those for kidneys exposed only to 6.1M cryoprotectant.

Figure 17B:
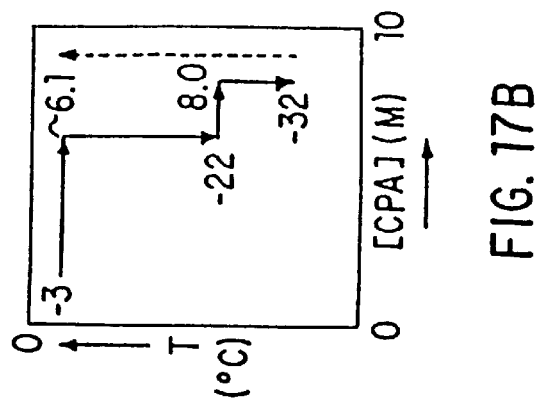
Figure 17A:
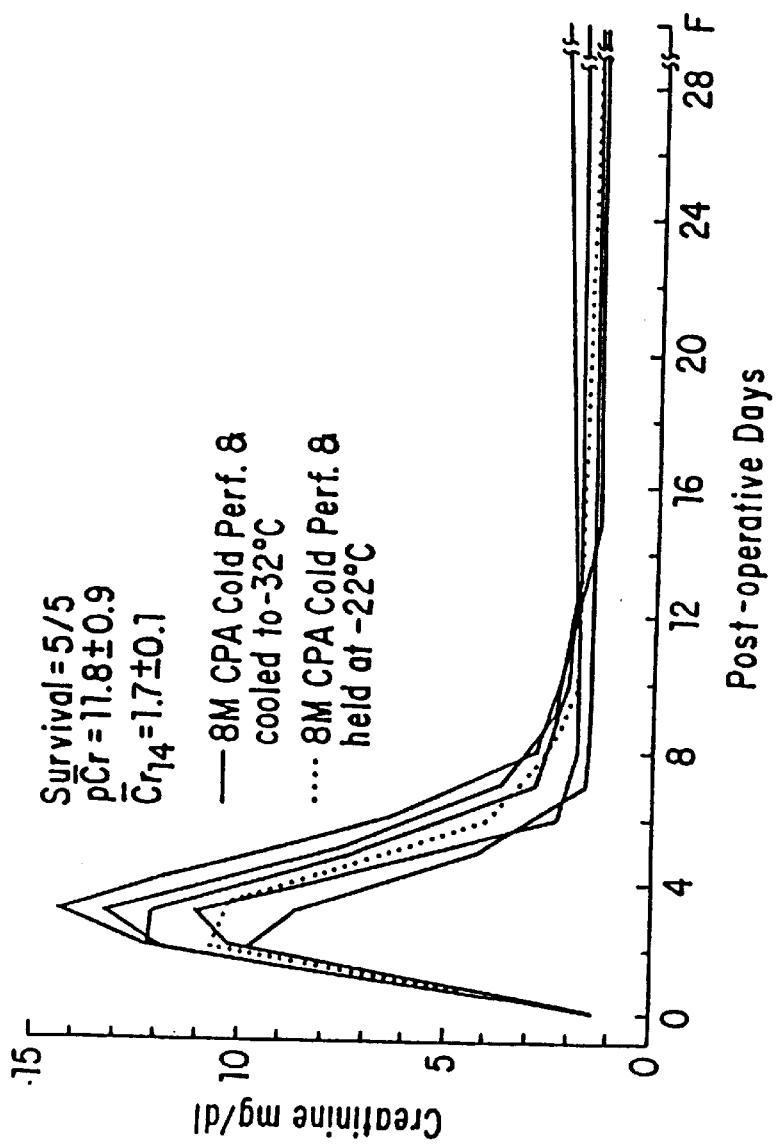

FIG. 17 (comprising FIGS. 17A and 17B) shows the feasibility of using the two-step approach to avoid cooling injury down to −32° C. with 8M cryoprotectant (survival rate =100%, final creatinine levels identical to those for kidneys exposed only to 6.1M cryoprotectant).

Figure 18A:
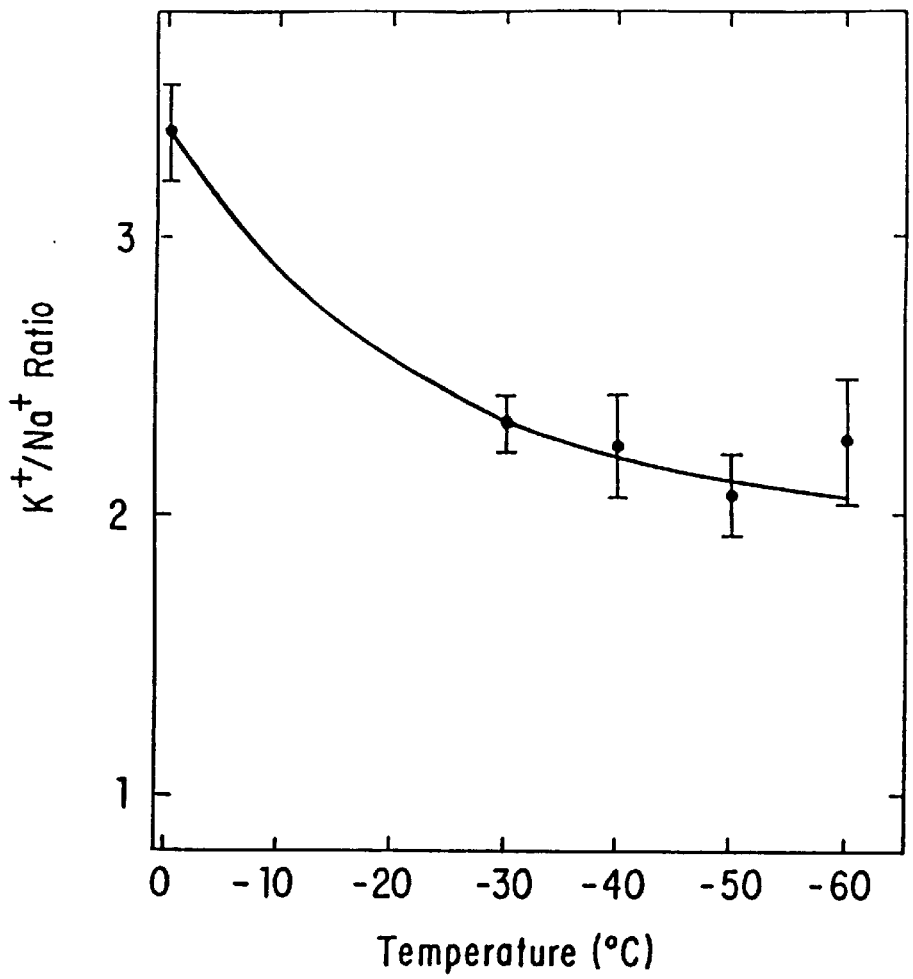
Figure 18B:
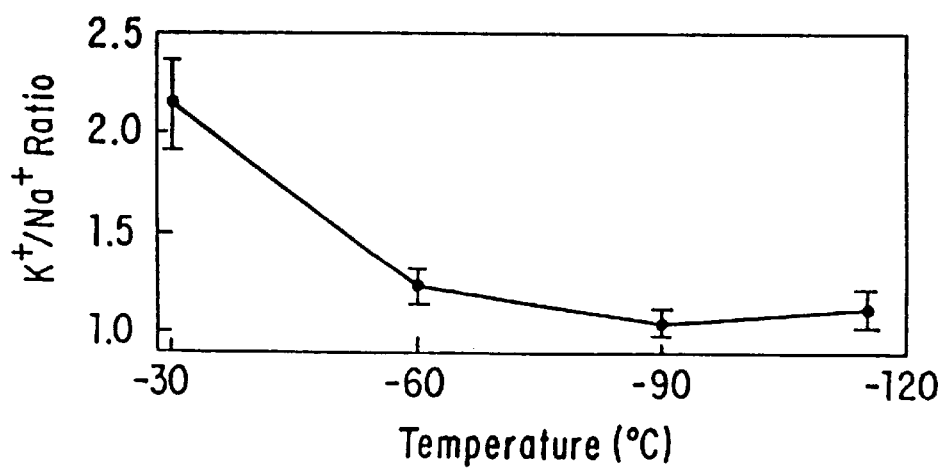

FIG. 18 (comprising FIGS. 18A and 18B) shows that kidney slices treated with V55 and cooled to −46° C. experience maximum cooling injury, no further injury being apparent when slices were cooled all the way to the glass transition temperature.

Figure 19:
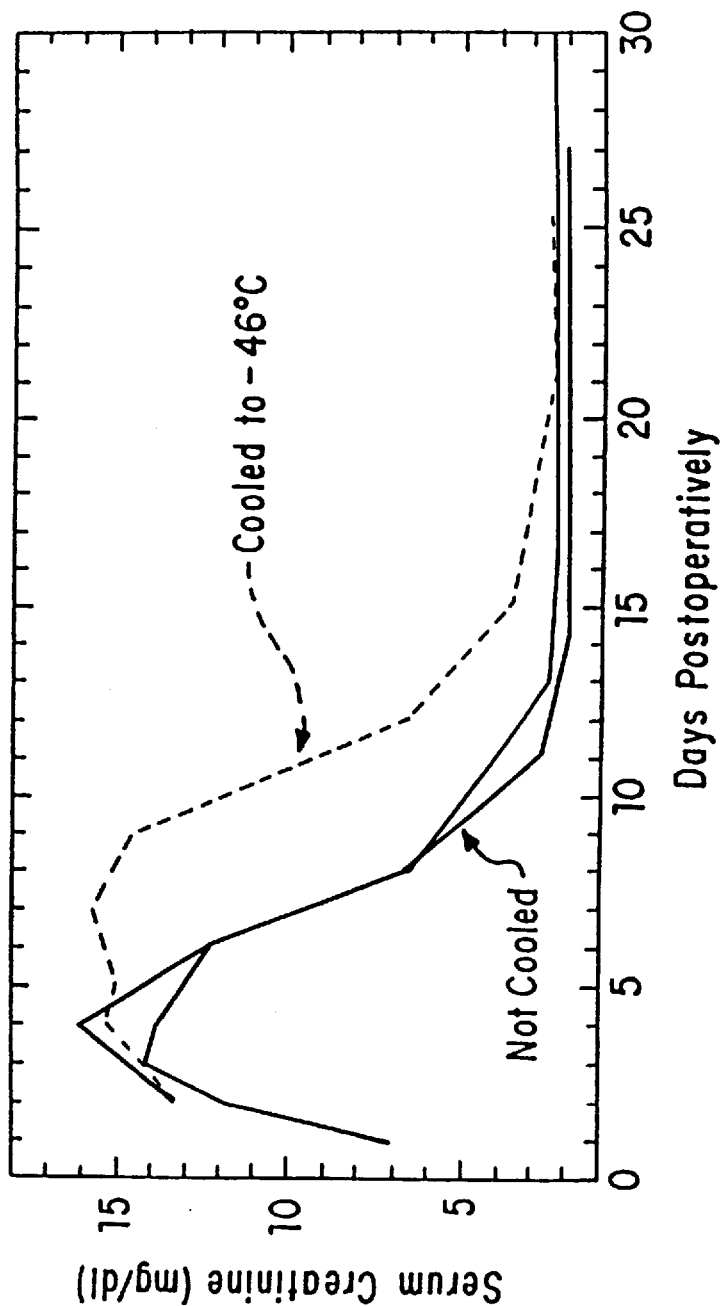

FIG. 19 shows the postoperative serum creatinine levels in an intact kidney that was treated with V55 and cooled to −46° C. with subsequent life support function (survival rate: 1/1 kidneys so treated; final creatinine levels: acceptable.)

Figure 20A:
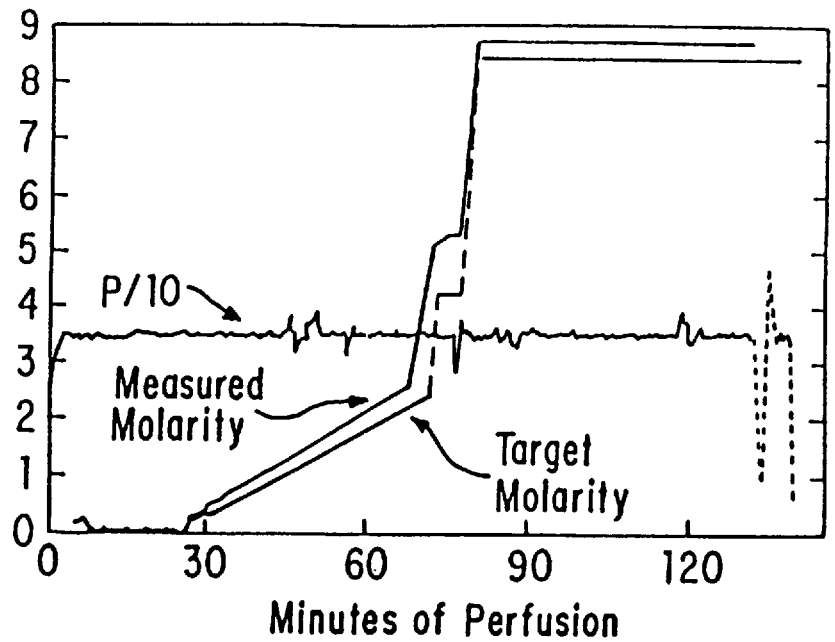
Figure 20B:
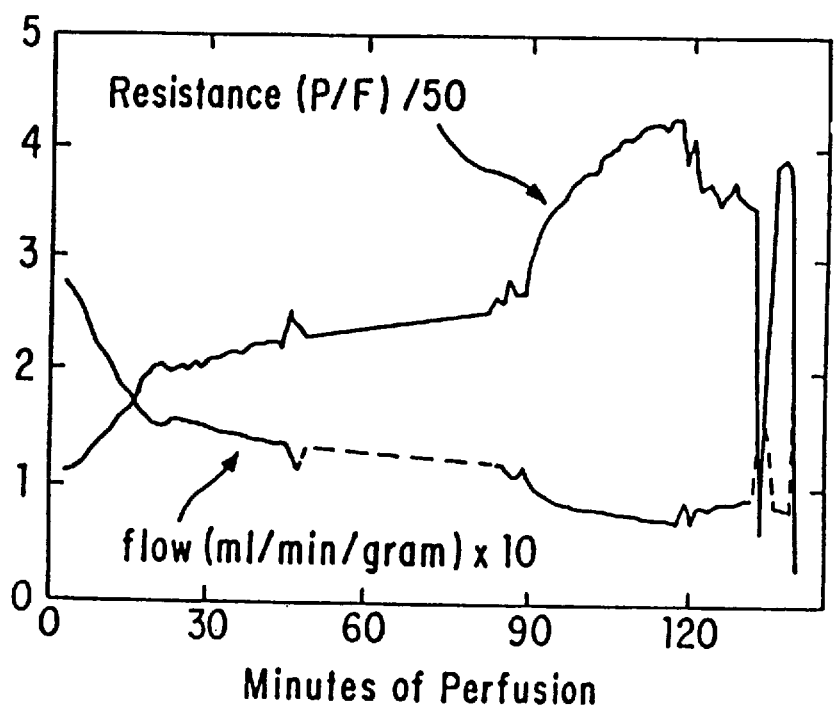

FIG. 20 (comprising FIGS. 20A and 20B) show data from the perfusion of a human kidney with the vitrifiable solution known as V55 by the method of this invention. Specifically, FIG. 20A shows successful control of cryoprotectant concentration. FIG. 20B shows resistance and flow data. The data are all from the same 232 grain human kidney. In FIG. 20A, P means pressure in mm Hg. In FIG. 20B, resistance is expressed as weight times pressure divided by flow rate $$\left( \frac{mmHg}{(ml/min)} \times g \right).$$

Figure 21:
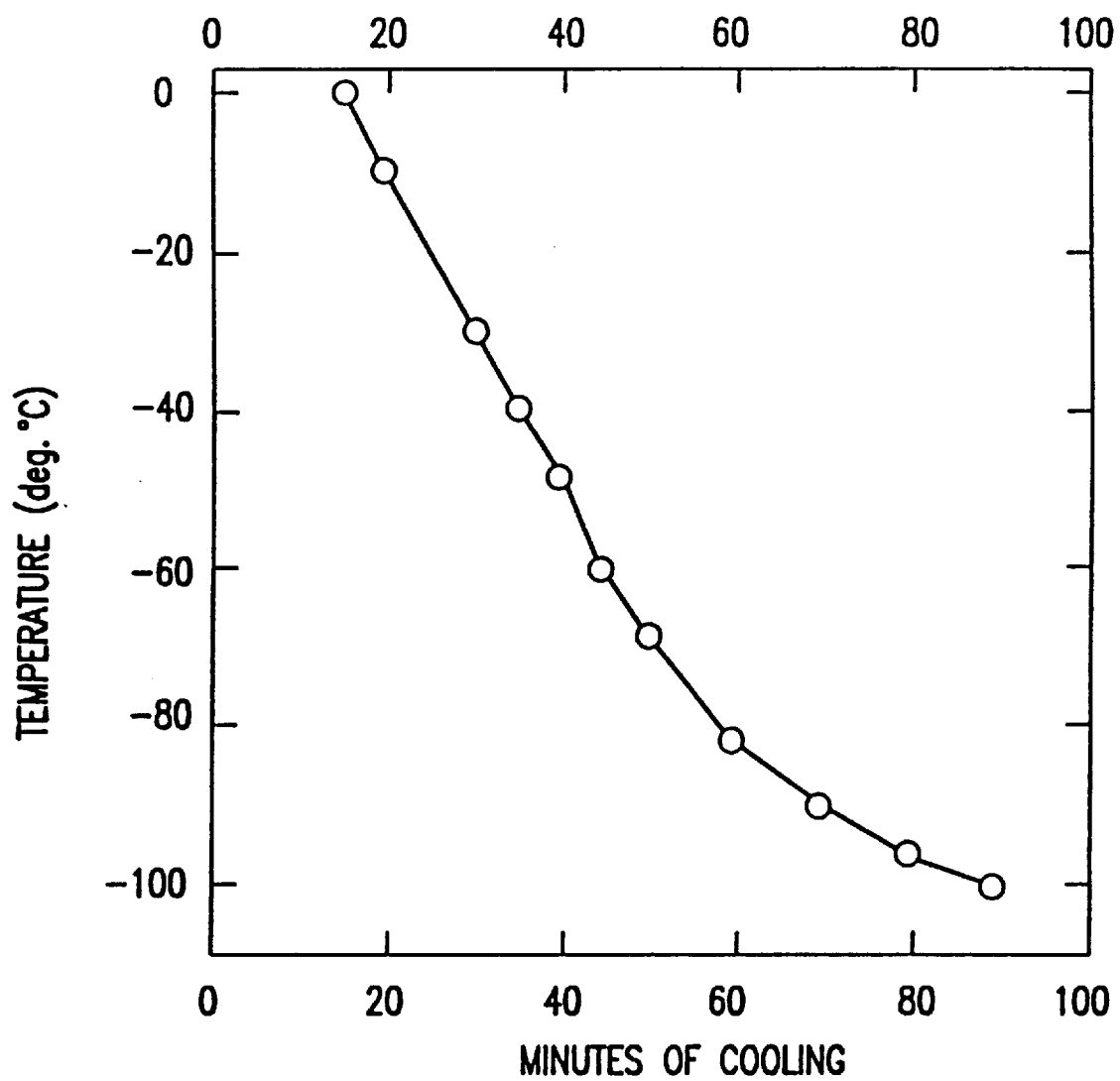

FIG. 21 shows cooling data from the same kidney as FIG. 20. The kidney was cooled after immersion in a 60% w/v mixture of dimethyl sulfoxide and acetamide. These data gave a continuous recording of organ core temperature from 0° C., which was reached in about 15 minutes, to about the glass transition temperature. The data revealed no evidence of ice formation within the kidney.

Figure 22:
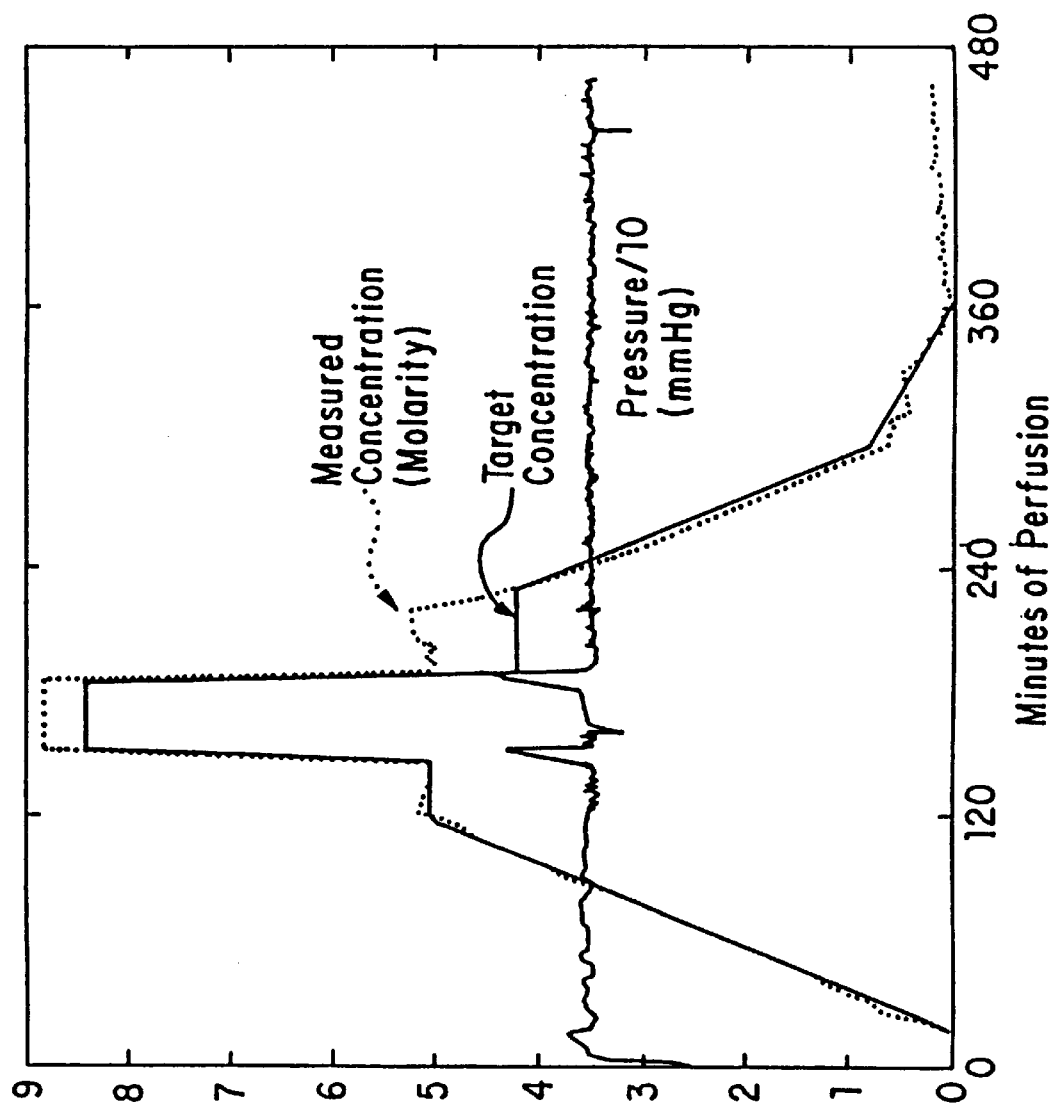

FIG. 22 shows loading (ascending portion) and unloading (descending portion) of a human pediatric kidney with V55 using the method of this invention. The solid line was the target V55 concentration while the dotted line was the actual measured V55 concentration in the circuit. Since the cryoprotectant was unloaded from this kidney a cooling curve was not generated.

Figure 23A:
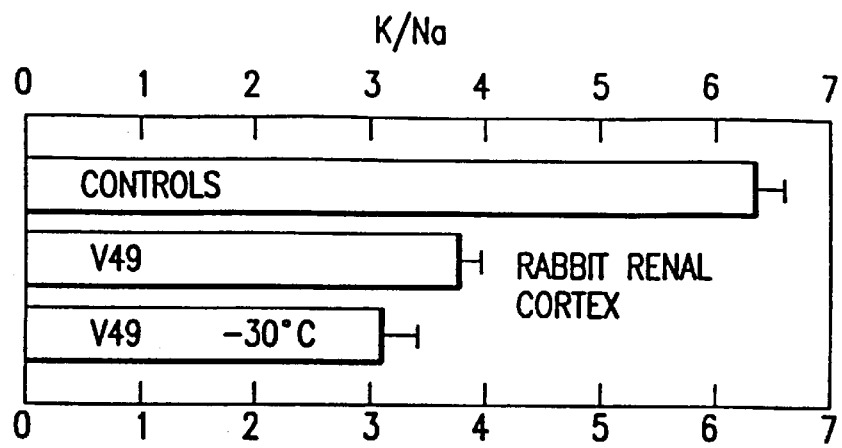
Figure 23B:
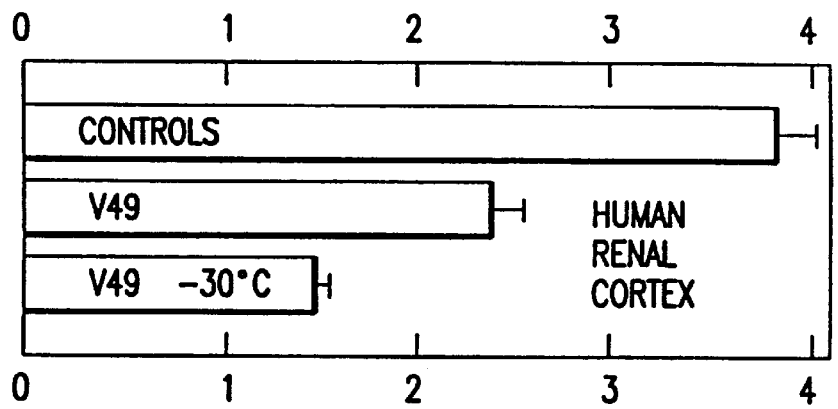
Figure 23C:
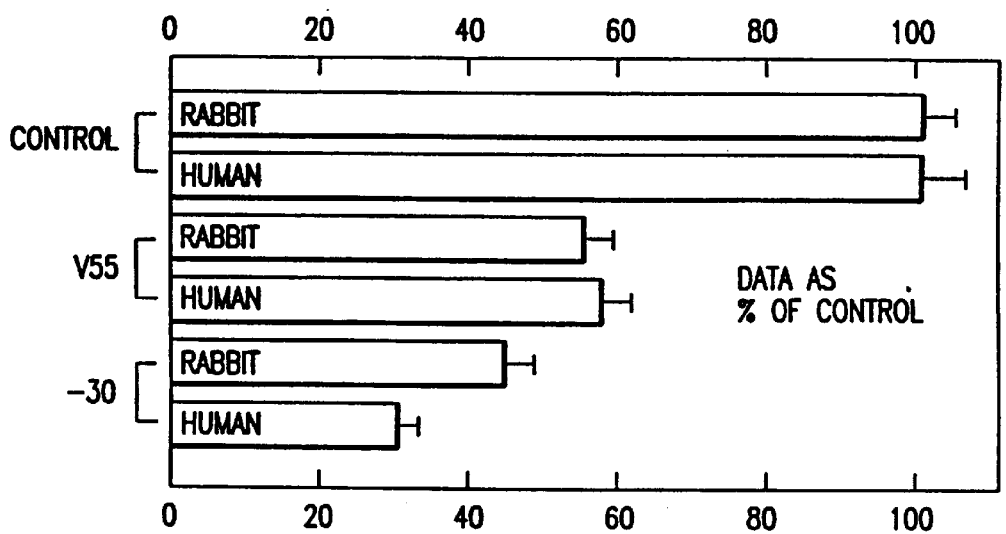

FIG. 23 (comprising FIGS. 23A–23C) shows viability data for rabbit kidney slices (FIG. 23A), human kidney slices (FIG. 23B) and comparative rabbit:human data (FIG. 23C). The human kidney slices showed identical responses to V49 as the rabbit slices but showed slightly lower recovery after cooling to −30° C.

DEFINITIONS

In order to provide a clear and consistent understanding of the specification and claims, including the scope to be given such terms, the following definitions are provided. Any terms which are not specifically defined in this or other sections of this patent application have the ordinary meaning they would have when used by one of skill in the art to which this invention applies at the time of the invention.

As used herein, "cryopreservation" means the maintaining of the viability of excised tissues or organs by storing them at very low temperatures. Cryopreservation is meant to include freezing and vitrification.

As used herein, "vitrification" means solidification of an organ or tissue without freezing it.

As used herein, "cryoprotectant" means a chemical which inhibits ice crystal formation in a tissue or organ when the organ is cooled to subzero temperatures and results in an increase in viability after warming, in comparison to the effect of cooling without the cryoprotectant.

As used herein, all temperatures are in ° C. unless otherwise specified.

As used herein, "non-penetrating" means that the great majority of molecules of the chemical do not penetrate into the cells of the tissue or organ but instead remain in the extracellular fluid of the tissue or organ.

As used herein, "osmotic buffering agent (OBA)" means a LMW or HMW "nonpenetrating" extracellular solute which counteracts the osmotic effects of greater intracellular than extracellular concentrations of cryoprotectant during the cryoprotectant efflux process.

As used herein, LMW OBAs have relative molecular masses ($M_r$) of 1,000 daltons or less. LMW OBAs include, but are not limited to, maltose, potassium and sodium fructose 1,6-diphosphate, potassium and sodium lactobionate, potassium and sodium glycerophosphate, maltopentose, stachyose, mannitol, sucrose, glucose, maltotriose, sodium and potassium gluconate, sodium and potassium glucose 6-phosphate, and raffinose. In a more preferred embodiment the LMW OBA is selected from the group consisting of mannitol, sucrose and raffinose.

As used herein, HMW OBAs have $M_r$ of 1,000 to 500,000 daltons. HMW OBAs include, but are not limited to, hydroxyethyl starch (HES) 450,000 daltons and lower $M_r$ hydrolysis fragments thereof, especially 1,000 to 100,000 dalton fragments), polyvinylpyrrolidone (PVP), potassium raffinose undecaacetate (>1,000 daltons) and Ficoll (1,000–100,000 daltons). In a most preferred embodiment the HMW OBA is HES, 450,000 molecular weight.

As used herein, "approximate osmotic equilibration" means that the difference between the arterial and venous concentrations is less than about 50 to 200 mM. (A difference of 200 mM at an arterial concentration of 4M means that the venous concentration is 95% of the arterial concentration. A 153 mM difference is equivalent to a 1% w/v concentration difference for our preferred cryoprotectant formula described below.)

As used herein, "animal" means a mammal including, but not limited to, human beings.

DETAILED DESCRIPTION OF THE PREFERRED EMBODIMENT AND BEST MODE

I. Description of the Perfusion Apparatus

Figure 1A:
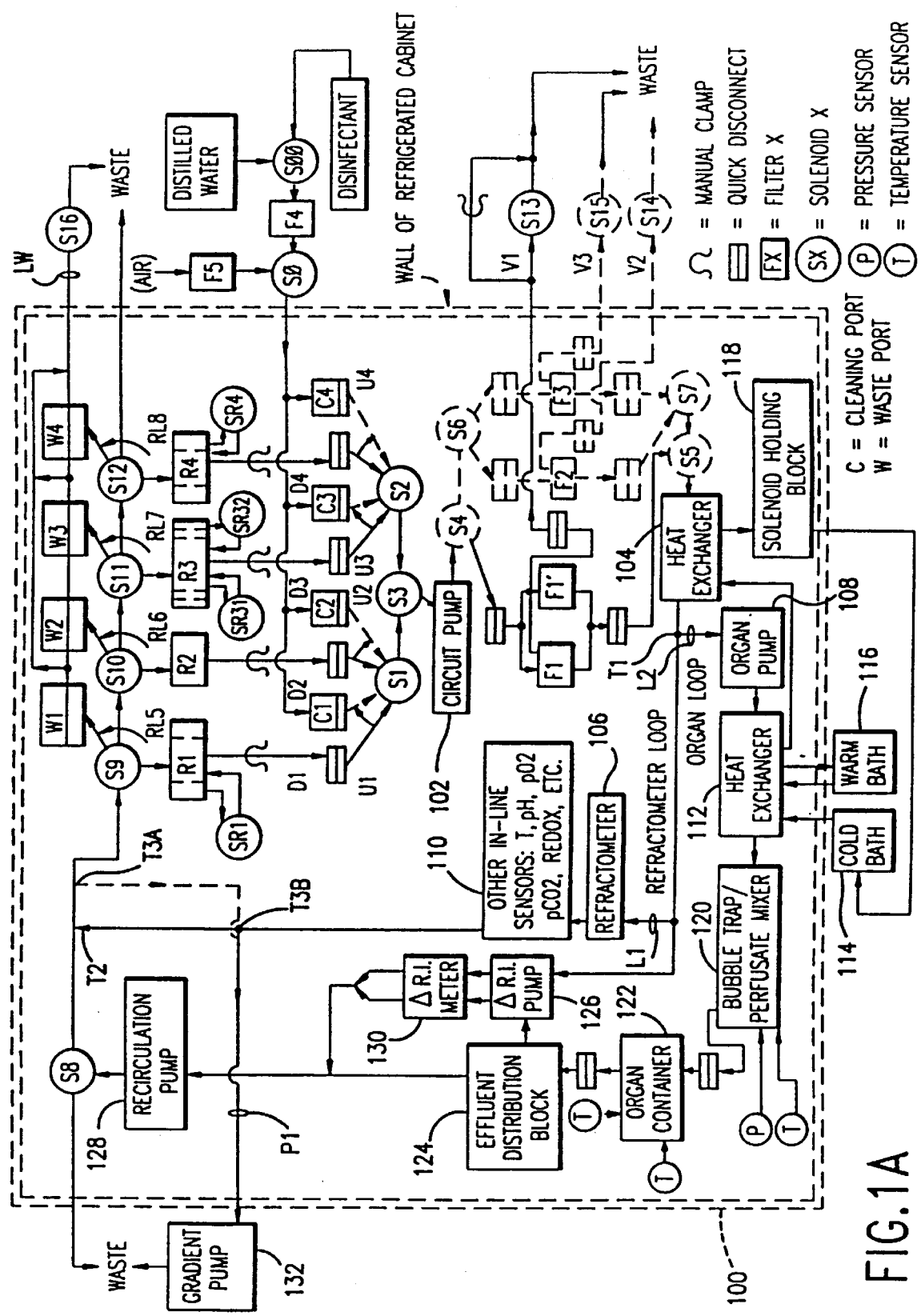
FIG. 1A shows the overall fluidic circuit diagram of this invention.

In a preferred embodiment, the apparatus incorporating the principles and features of this invention is contained in a refrigerated cabinet 100 (shown by double dashed lines in FIG. 1A). The refrigerated cabinet contains two sides, the reservoir/solenoid side and the organ/refractometer side. The cabinet is faced with double paned transparent doors each containing approximately 1 inch of insulating air (which can be reduced in pressure and/or humidity if necessary) between the panes to avoid condensation of moisture on the doors and to minimize heat leak into the cabinet. The organ-side door is split to form a "Dutch door". This allows the upper portion of the organ-side door to be opened and closed to place the organ in the system and to remove the organ without changing the temperature below the upper portion of the door, where the organ container and most other equipment are located. The cabinet may also employ a "Dutch door" on the reservoir side of the cabinet to enable the operator to make any needed adjustments (e.g., fluid addition to the reservoirs, transfer of upper fluid lines, etc.) without disturbing the cabinet's temperature to an unnecessary degree.

The primary features of the invention and its mode of operation are shown in the fluidic logic schematic of FIG. 1A. All fluid available for circulation through the system is drawn into the main circuit by a circuit pump 102 through fluid uptake lines U1, U2, U3, or U4 depending upon the computer-controlled actuation pattern of three-way solenoid valves S1, S2, and S3. Uptake lines U1–U4 connect either to fluid delivery lines D1–D4 leading from reservoirs R1–R4, respectively, or to cleaning ports C1–C4, through standard tubing quick disconnects. By clamping D1–D4 and unplugging them from uptake lines U1–U4, lines U1–U4 can be plugged into cleaning ports C1–C4, as indicated by the curved arrows. While this is presently done manually, it will be appreciated by those skilled in the relevant arts that appropriate valves, tubing and controls could be added to handle most of these tasks automatically.

Figure 1B:
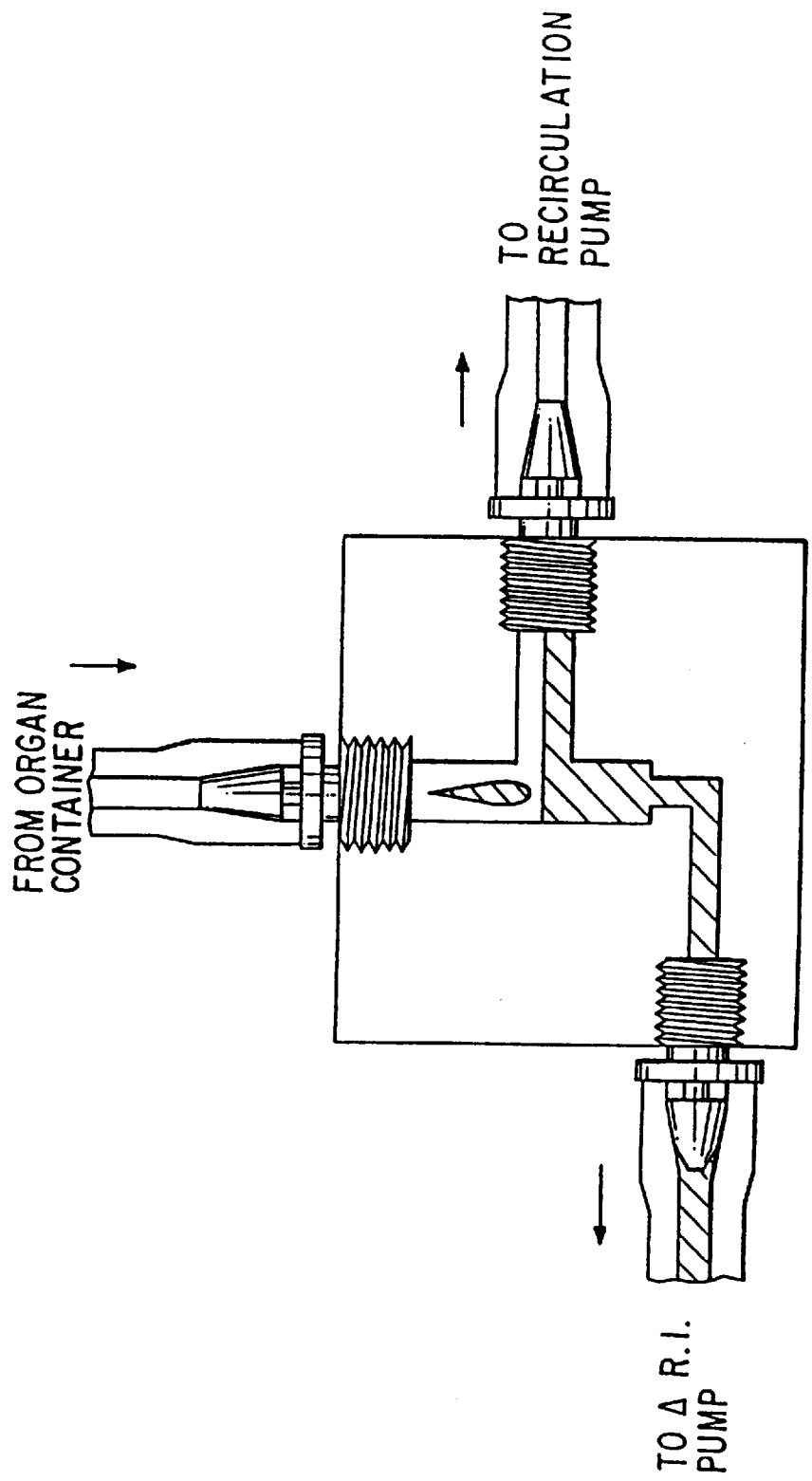
FIG. 1B shows the construction of the Effluent Distribution Block (EDB) and the means by which the effluent flow is divided to allow sampling by the Δ R.I. pump 126 in FIG. 1A.

In the embodiment of the invention as presently constructed, the reservoirs R1–R4 are supported on a thick transparent plastic shelf from which four magnetic stir tables hang which stir the four reservoirs (not shown in FIG. 1). Thorough stirring of R1, R3, and R4 is necessary for proper generation of the desired concentration-time histories. The on/off states and stir rates of the stir tables are independently controlled by instrumentation located outside the refrigerated cabinet.

Ports C1–C4 lead to sources of sterile (distilled) water, air, and disinfectant. Solenoid valves S0 and S00 are interposed in the delivery lines for these sources and are arranged to ensure that traces of disinfectant do not enter the perfusion system by accident. Solenoid S0 controls whether air or fluid will enter the perfusion circuit for cleaning, while solenoid S00 determines whether the fluid selected will be water or disinfectant. The breakup of the main cleaning line into four independent channels outside of the cabinet rather than just before reaching C1–C4 (not so indicated in FIG. 1) ensures that each channel is independent of the others, i.e., not subject to any meaningful cross-contamination resulting from diffusion of unpurged solution backwards from the fluid uptake lines U1–U4 into the cleaning lines leading to cleaning ports C1–C4.

Distilled water and disinfectant are drawn into the system through a sterilizing filter F4, while air is drawn into the system through an air filter F5. The disinfectant of choice at present is a clinically accepted dialysis machine cold sterilant such as Actril™ (Minntech, Minneapolis, Minn.). The cleaning procedure is to wash the perfusate out of the system with water and then to displace the water with sterilant. Prior to the next perfusion, the sterilant is washed out of the system with water and the water is then washed out of the system with air. The system is then primed by displacing the air with appropriate perfusate. The air flush is used to avoid the persistence of any lingering traces of sterilant dissolved in the rinse water, and to avoid any possible dilution of the priming fluid with water (i.e., to reduce the amount of priming fluid needed for displacing water from the system), to allow a visual check of the completeness of priming, and to reduce spillage of water in the cabinet when the reservoirs, filters, and organ cassette are placed into the system after cleaning but before priming. The air purge can, however, be omitted if desired. The air filter is used to prevent contamination from pathogens in the air, if necessary.

Solenoid valves S9–S12 normally direct fluid to reservoirs R1–R4 or to the waste line (LW). Reservoirs R1–R4 can also be detached from the system by removing recirculation lines RL5–RL8 from reservoirs R1–R4 and plugging them into waste ports W1–W4, respectively (as indicated by curved arrows), allowing reservoirs R1–R4 to be removed from the system for cleaning, sterilizing, and refilling. When reservoirs R1–R4 are removed, valves S9–S12 direct fluid to waste ports W1–W4. The four waste lines corresponding to waste ports W1–W4 converge to a single common waste line LW. A two-way solenoid valve S16 is located on the common waste line. When the waste ports are not in use, the common waste drainage line is blocked by closing valve S16 to prevent any possible backflow of waste or pathogens into the sterile cabinet.

The use of this system of uptake lines U1–U4, which are plugged alternately into reservoir delivery lines D1–D4 or cleaning ports C1–C4, in combination with recirculation lines RL5–RL8, which are plugged alternately into the reservoir internal return lines (not shown in the figure) or into waste ports W1–W4, allows complete sterilization of the perfusion circuit. The blunt ends of the uptake lines U1–U4, delivery lines D1–D4, cleaning ports C1–C4 and waste ports W1–W4 may be sterilized by swabbing with disinfectant when the tubing is being transferred from one alternative position to the other. The tubing transfer is accomplished while applying digital pressure to the tubing so as to occlude it while making the transfer to prevent fluid leaks and further reduce the risk of contamination.

The fluid withdrawn from reservoirs R1–R4 or from ports C1–C4 is delivered through one of several filters F1, F2, and F3, depending upon the state of actuation of solenoid valves S4 through S7. These actuation patterns will be described in more detail below. Experience has shown, however, that a single filter F1 or two filters F1, F1' in parallel will be adequate for most studies (rendering valves S4–S7 optional, as indicated by broken lines) since virtual step changes in concentration can be imposed even when only one or two filters in parallel are present in the circuit.

It is desirable to minimize the distance between the circuit pump 102 head and the solenoids S1–S7 to minimize circuit dead space and dead time and to minimize the effects of perfusate viscosity. Short distances and adequate tubing inner diameters are particularly critical for S1–S3 to assure adequate fluid withdrawal from R1–R4.

Standard Millipore filters appear (Bedford, MA) compatible with our cryoprotectants. The filters are capable of sterilizing the perfusate and are autoclavable. All filter holders can be removed from the system for cleaning and sterilization by means of the quick disconnects shown in FIG. 1A. Vent lines V1–V3 lead to solenoid valves S13–S15, located outside of the refrigerated portion of the cabinet 100. These vent lines are opened and closed under computer control during priming and cleaning of the system to permit air to escape and thereby prevent the filters from becoming blocked by air or damaged. A manual bypass (shown only for the S13 bypass) is provided for V1–V3 for emergency purging of air from the circuit. Obviously, air purges of the system beyond filters F1–F3 are not possible if filters F1–F3 are present in the circuit; hence filters F1–F3 must be removed before beginning the washout of sterilant if an air purge is to be included in that procedure.

In the presently preferred embodiment, a 90 mm diameter filter of 0.22 micron pore size is located in each filter holder. This size filter is able to pass enough vitrification solution at −6° C. to permit the successful perfusion of a rabbit kidney, with an overlying 1.2 micron filter and a coarse prefilter to prevent clogging. The standard configuration for the operative version employs two identical filters in parallel. This is necessary to accommodate the flows required for human organs and provides a safety factor for any air which may be inadvertently introduced into the arterial fluid, as well as minimizing pressure build-up proximal to the filter. This continuous filter sterilization and resterilization of the perfusate during the perfusion can serve as a back up for pre-sterilized solutions in case of contamination for any reason during the perfusion. (The incidence of renal infections has been 0% after literally several hundred perfusions.)

Once the fluid from the selected reservoir has passed through the appropriate filter, it goes through some preliminary temperature conditioning in a heat exchanger 104 and then travels to a position as close to the organ as possible, at which point it encounters a "T" type tubing connector T1. The bulk of the flow passively takes the path L1 ("refractometer loop") that leads to a flow-through process control refractometer 106 that measures the index of refraction of the liquid and hence the cryoprotectant concentration. The remainder of the flow is directed through an organ loop L2 by means of an organ pump 108. The organ pump speed is controlled by the computer so as to maintain the desired organ perfusion pressure despite wide variations in the organ's vascular resistance. By changing the organ pump head and the diameter of the tubing going through it, a wide range of flows can be generated sufficient to perfuse organs of a wide range of sizes: organs as small as rat hearts to organs as large as human kidneys have been successfully perfused.

The flow rate delivered by the circuit pump 102, which supplies both the refractometer loop L1 and the organ loop L2, must be high enough to both exceed the flow rate through the organ at all times and to ensure that sufficient flow is available for the refractometer 106 and other in-line sensors, generally designated 110, for measuring temperature, pH, and other desired parameters of the perfusate, to permit accurate measurements. The flow must also be high enough to minimize the "dead time" between changes in reservoir concentration and changes in the sensed concentration and other sensed parameters in the refractometer loop as well as to minimize the "dead time" between the reservoir and the organ. The circuit pump flow is limited by the need to prevent fluid from being delivered to the filters at a rate in excess of what these filters or the tubing leading to them can pass without failing, as well as by constraints of heat output and wear and tear on the circuit pump tubing. The speed of the circuit pump is usually not varied during an experiment and does not therefore usually require computer control, though computer control is available as an option.

After passing through the organ pump 108, the perfusate passes through a second heat exchanger 112 that finalizes perfusate temperature conditioning. This is done by adjusting the flow of both cold and warm liquid from cold and warm baths 114, 116, respectively, using computer-controlled pumps (not shown) between heat exchanger 112 and baths 114 and 116.

The computer is able to vary flow through both the cold path and the warm path so as to adjust perfusate temperature in the arterial line and therefore also in the effluent of the organ. The arterial and effluent temperatures provide an indication of the actual organ temperature. By controlling the flow rate of cold and warm bath fluid, organ temperature can be adjusted independently of organ flow, provided flow is not close to zero. Experience has shown that arterial and venous temperatures at least as cold as −6° C. and at least as high as 25° C. can be achieved with this invention. Generalized cabinet cooling is not an alternative to the heat exchange system shown for subzero perfusions because cooling of the cabinets to subzero temperatures will cause freezing of the more dilute solutions in the tubing lines. Specific jacketing and cooling of the organ container is of particular theoretical value, however, and may optionally be included.

The temperature-conditioned perfusate is then debubbled and mixed in a bubble trap/mixer 120 just before entering an organ container 122. Arterial and venous temperature probes, generally designated "T" in FIG. 1A, penetrate the wall of organ container 122 through simple holes. Pressure and, optionally, temperature is sensed in the bubble trap. Although shown separately in the drawing for ease of understanding, the bubble trap and mixer 120 are in fact an integral part of the heat exchanger 112, so heat exchange continues to be controlled while debubbling and mixing are accomplished. Experience has shown that mixing was important due to the tendency for layering of dilute solutions on more concentrated, denser solutions. Details as to the specific construction of the heat exchanger/bubble trap/mixer (HBM) are described below.

Under normal circumstances, the cooling fluid effluent from this second heat exchanger 112 is used to cool the perfusate passing through the preliminary heat exchanger 104. This cooling fluid then travels to a solenoid holding block 118 physically containing solenoids S1–S12, so as to draw off waste heat from these solenoids before returning to the cold bath.

The holding block 118 currently consists of a large aluminum block (but may be either metal or plastic) perforated with cylindrical holes of sufficient diameter to closely match the outside diameters of the held solenoids. The solenoids are inserted such that the base, containing the fluid inlets and outlets, faces the operator and the head, from which the electrical leads penetrate into or through the holding block. The solenoid holding block is equipped with an internal fluid path for drawing off waste heat from the solenoids. Feet are provided to position the holding block, prevent it from moving, and protect the fluid inlet and outlet ports when the holding block is removed from the cabinet. The block is positioned behind and above the reservoirs in the refrigerated cabinet so that the solenoid inlets and outlets and their connections to the reservoirs are always readily visible.

The solenoids are preferably 3–7 watt (or less) piston type 3-way solenoids of minimal internal fluid volume having orifices on the order of 0.156 inches or more and Cv values $\geq 0.16$ (e.g., Model 648T033 solenoids from Neptune Research, Maplewood, N.J.) while resisting pressures of up to 500 mm Hg or so. The inventors presently prefer Neptune Research (supra), 3-watt solenoids fitted with RC dropping circuits to reduce heat generation after activation. Solenoids having $\frac{1}{16}$ inch orifices and Cv values of 0.01 to 0.03, e.g., Valcor's Model 20-2-3 (Valcor Scientific, Springfield, N.J.) are not fully satisfactory due to the high viscosity of the solutions used for cryopreservation (causing difficulty aspirating viscous fluid through S1–S3), the high flows desired for controlling dead times and for perfusing larger organs, the possibility of clogging, and the buildup of pressure between the circuit pump and S8–S12. The detailed actuation pattern of the solenoids is described below. The solenoids inside the refrigerated cabinet that are not held in the solenoid block, SR1, SR31 and SR32, are described in more detail below.

An effluent distribution block (EDB) 124 (FIG. 1A) is connected to the output side of the organ container 122. The EDB is designed so that a small amount of effluent is always present at the bottom of the block. This residual fluid is withdrawn by the two-channel "delta R.l. pump" 126 and sent to the differential refractometer ("delta R.I. meter") 130 where its refractive index (a measure of concentration) is compared to that of the perfusate from refractometer loop L1 (pumped at the same rate as the venous effluent sample) and a difference signal generated and sent to the computer. Since the fluid in the refractometer loop L1 will approximate the concentration of the fluid entering the artery of the organ, the delta R.l. output provides an estimate of the arterio-venous concentration gradient across the organ. When this gradient is large (in either the positive or negative direction), the organ is far from equilibrium. When the gradient is zero, the organ is at least largely in osmotic equilibrium with the perfusate. The nonlinear baseline resulting from this unorthodox use of the differential refractometer is accounted for in the software for running the perfusion program.

All effluent from the organ (together with the arterial fluid sampled by the delta R.I. pump) is ultimately collected by the recirculation pump 128 and sent to solenoid S8, which controls whether the effluent is recirculated to the reservoirs or discarded. Effluent to be returned to a reservoir is combined with the fluid flowing through the refractometer loop L1 at a T connection T2. As noted above, return to the correct reservoir is then controlled by the actuation of solenoids S9 through S12.

The recirculation pump 128, like the circuit pump 102, need not require flow adjustment. It is normally set to a rate sufficient to exceed the maximum flow through the organ pump 108. Since the output of the recirculation pump exceeds that of the organ pump, air is continually introduced into the tubing leading to solenoid S8 and usually to the reservoirs R1–R4. Provisions to prevent excessive bubbling of the reservoirs as a result of this are described below.

Although the delta R.I. pump speed can be changed, it is usually kept constant throughout an experiment. In the presently operative version, it has not been under computer control, but computer control would be a desirable option in some cases. The delta R.I. pump employs very small diameter polyethylene tubing to reduce delays in fluid transit time. This small tubing is particularly important because the flow rate through the delta R.I. circuit is limited by the lowest flow rate through the organ, which may be small, and by the limited size of the fluid paths in commercially available differential refractometers.

The return of the differential refractometer output to the organ effluent line is proximal to the effluent recirculation pump. This placement rather than placement distal to the pump ensures a steady flow through the differential refractometer, whereas distal placement may prevent or alter differential refractometer flow by virtue of a higher exit pressure.

An important element of the fluidic circuit is the gradient pump 132 connected to the circuit by a line P1 (FIG. 1A). The function of the gradient pump is to allow for gradual changes in concentration within the appropriate reservoirs within the cabinet. The method by which this is accomplished will be described below. The placement of the line P1 to the gradient pump at T3A, just after the point of joining of the refractometer loop L1 and the organ loop L2, presents one option for ensuring the removal of some of the air introduced by the organ effluent recirculation pump 128 and therefore helps reduce bubbling of the reservoir fluid.

A better option, however, and the one presently used, is to draw no air into line P1. This is accomplished by connecting P1 at point T3B and results in fully controlled concentration-time histories. The bubbling problem is then overcome by continuously regulating the speed of the recirculation pump 128 to be just slightly in excess of the combined flows of the organ pump 108 and the delta R.I. pump 126 so as to introduce little air. Attaching the recirculation output of S8 directly to P1 without regulating the speed of pump 128 results in degraded concentration control and is not recommended.

The present operative version of the embodiment of the invention uses silastic tubing of $\frac{1}{8}$ inch diameter throughout the system, which is sufficient to accommodate the needed flows and is preferred. Silastic is compatible with Actril™

(Minntech, Minneapolis, Minn.) cold sterilant, is translucent (important for visualizing flow to detect problems and for observing any signs of microbial growth), is impervious to common cryoprotective agents such as dimethyl sulfoxide, and is soft enough to be easily manipulated. However, silastic tubing should not be used in circuits coming into contact with silicone cooling fluids, which swell and weaken silastic tubing. In addition, C-Flex® tubing (Cole Palmer Instrument Co., Chicago, Ill.) should be used in the pump heads due to its greater strength (silastic tubing undergoes spallation) and greater flexibility when cold.

Figure 2A:
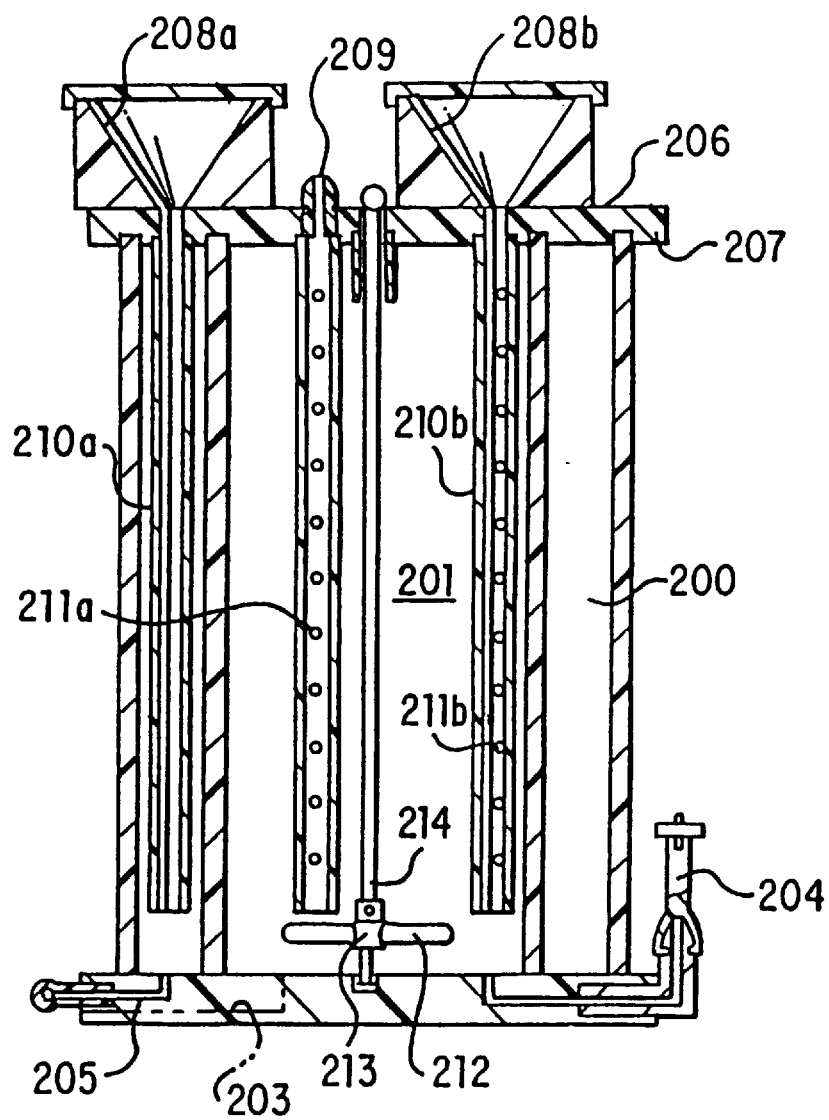
FIGS. 2A–C show side, top and bottom views, respectively of a two-chamber gradient former employed as reservoir R1 in this invention.

Reservoir R1 is constructed as a gradient former (FIG. 2). Essentially the gradient former consists of two concentric cylinders, an outer cylinder 200 and an inner cylinder 201. A fluid path 205 allows fluid to flow from the outer cylinder 200 to the inner cylinder 201 under the influence of gravity in response to a reduction of volume in the inner cylinder. The concentric orientation of the fluid compartments is very space efficient. The fluid delivery line 204 corresponds to the line D1 of FIG. 1A. The unit shown is a modification of a commercially available gradient former. The necessary modifications for use with this invention are as follows.

1) The stopcock normally used to control flow from the outer cylinder to the inner cylinder in the commercial device is replaced by a pinch-type-two-way (on/off) solenoid valve 202 (currently, a Bio-Chem Valve Corp. model 100P2WNC, East Hanover, N.J.) (FIG. 2C). A pinch-type valve is preferable for this application to a piston-type valve because of the small pressure difference available to drive fluid flow and the consequent need for a large working diameter fluid path 202$b$. It is also preferable for easy removal from its tubing 202$b$ when the reservoir is to be removed from the cabinet for cleaning, leaving the solenoid behind. The base of the gradient former has been modified, at 203, to make room for the solenoid and to support it on a platform. Platform 203 is equipped with a vertical metal post 203$b$. Solenoid 202 is lashed to this post with a rubber band so as to keep the solenoid oriented correctly. The solenoid is located a sufficient distance from the reservoir to avoid excessive heating of the reservoir fluids.

2) The diameter of the fluid path 205 from the outer cylinder 200 to the inner cylinder 201 has been enlarged to permit flow at an adequate rate of the viscous solutions required for organ cryopreservation. An inner diameter of 1/8 to 3/16 inch is adequate.

Figure 2B:
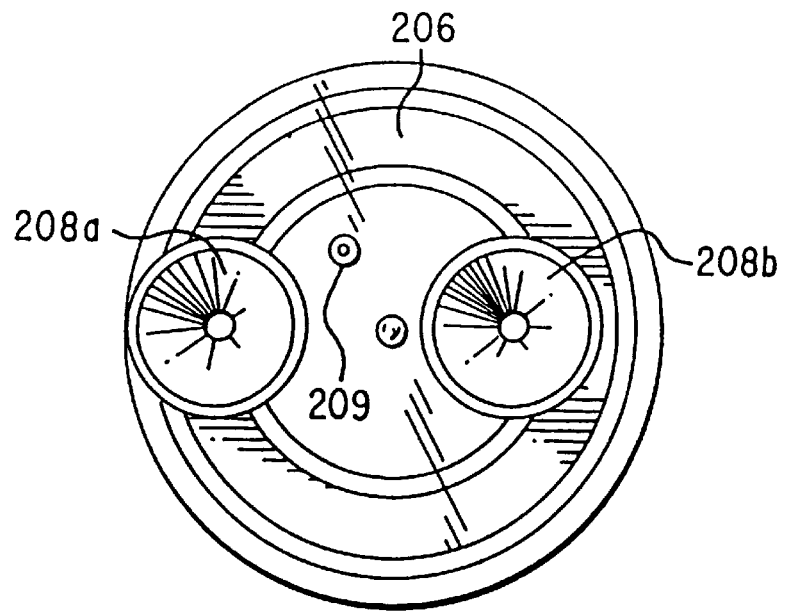
Figure 2C:
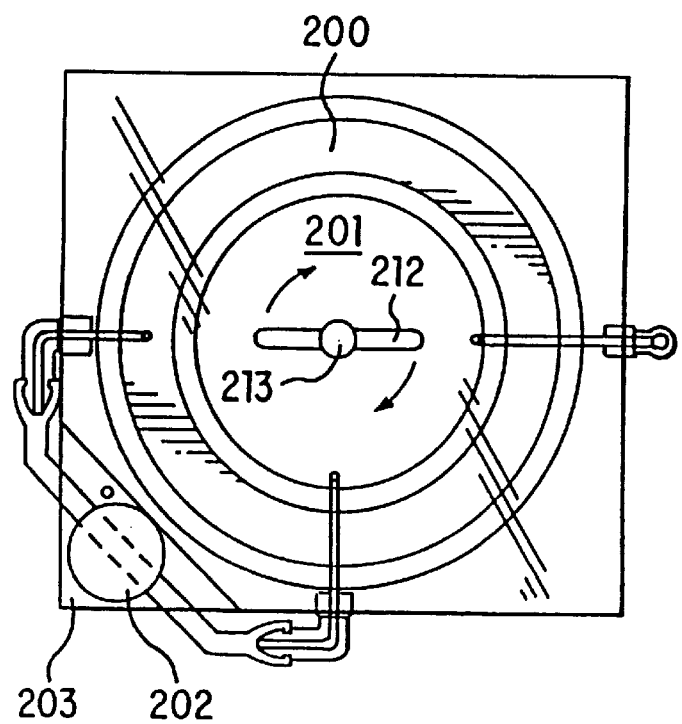

3) A lid 206 has been provided (FIG. 2B). The lid has an outer overhang 207 that prevents the lid from moving from side to side after it is placed on the cylinder as well as concentric grooves into which the wells of 200 and 201 fit. The lid has built-in outer and inner filling funnels 208$a$ and 208$b$ with removable lids, and a recirculation port 209.

4) Funnels 208$a$ and 208$b$ extend into respective internal fill tubes 210$a$ and 210$b$. The internal fill tubes are preferably rigid hollow rods located next to the wall of the inner and outer cylinders and are perforated at 1–2 cm intervals with holes 211$a$ and 211$b$, respectively, which are approximately 3 mm in diameter. The function of the fill tubes is to reduce the creation of bubbles as recirculating fluid impacts the surface of the liquid in the reservoir. The purpose of the perforations is to enable air to escape from the tube through the perforations so as not to force air to the bottom of the reservoir to form bubbles. These functions are particularly important in perfusates containing protein, which tend to stabilize bubbles.

5) A fill mark has been provided to enable the reservoir to be filled reproducibly to the same, predetermined volume. The operator can establish his/her own fill mark depending upon the details of the application. The gradient formers may have approximate graduations (horizontal lines on both the inner and outer cylinders, aligned so as to permit avoidance of parallax error in reading the liquid level in either cylinder) spaced approximately 0.5 cm apart for a 2 liter gradient former. These graduations are also important for establishing slight, deliberate mismatches in liquid level between inner and outer cylinders, which are necessary to prevent premature mixing of solutions of widely differing densities, such as cryoprotectant-free perfusate and vitrification solution. They also permit a rough quantitative check by the operator on the progress of the gradient as represented on the computer screen.

6) The plastic composition of commercially available gradient formers may create problems for certain types of cryoprotectant, which could conceivably attack the plastic. It is therefore preferred to use reservoirs made of transparent material (e.g., glass, plexiglass or the like) that is compatible with the cryoprotectant chemicals or use reservoirs whose surfaces have been siliconized or otherwise treated to prevent the attack. In the inventors' experience, acrylic has been found to be an acceptable material.

7) The reservoir R1 contains a stir bar 212. The stir bar is housed in a jacket 213 attached to a freely spinning vertical pin 214 extending to the stir bar from the lid of the reservoir to prevent the jacket, and hence the stir bar, from moving laterally. This change is necessary to make sure chattering, and therefore poor mixing, does not occur while the perfusion machine is unattended. Support from above rather than below prevents unnecessary perfusate frictional heating and wear and tear to the floor of the reservoir.

Figure 3A:
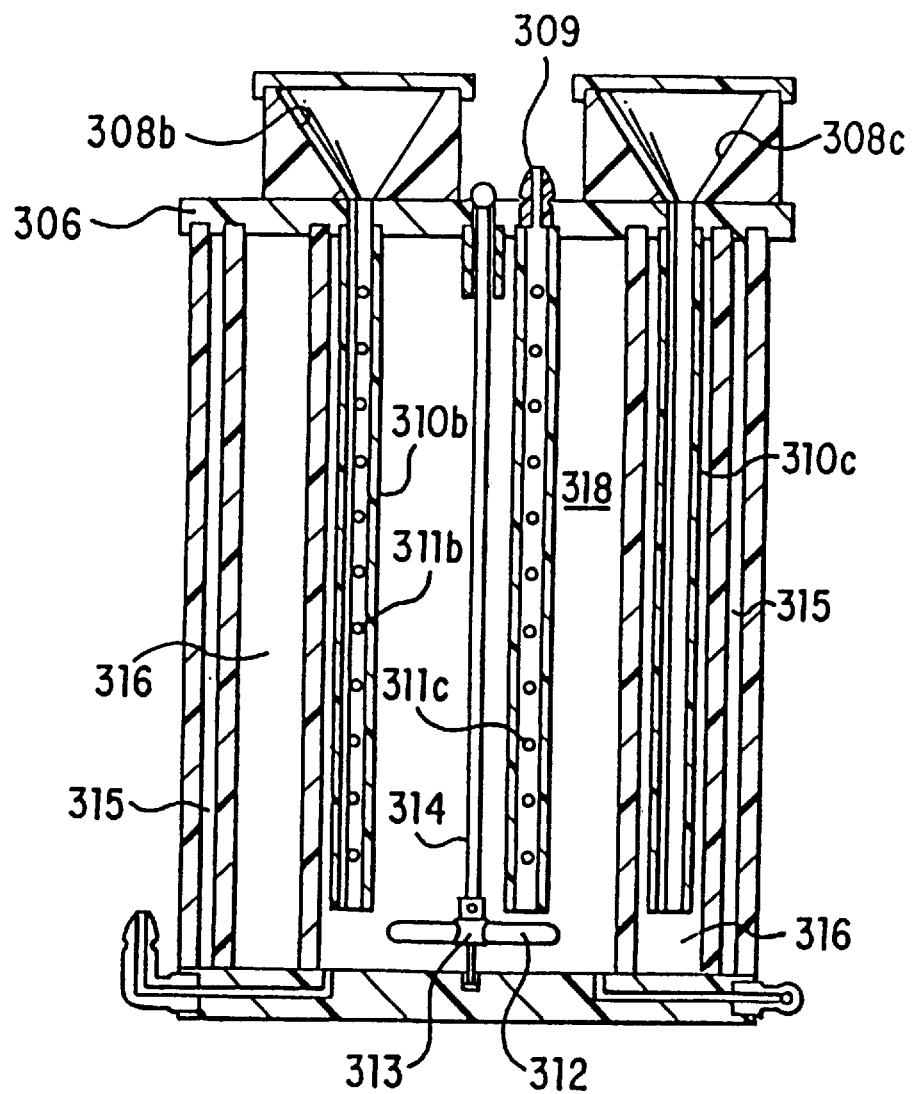
FIGS. 3A–C show side, top and bottom views, respectively, of a three-chamber gradient former used as reservoir R3 in this invention.
Figure 3B:
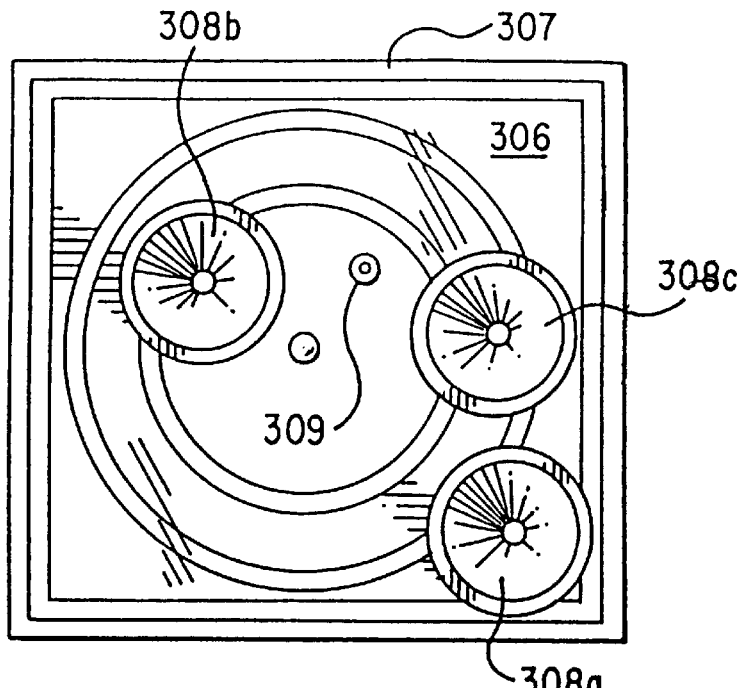
Figure 3C:
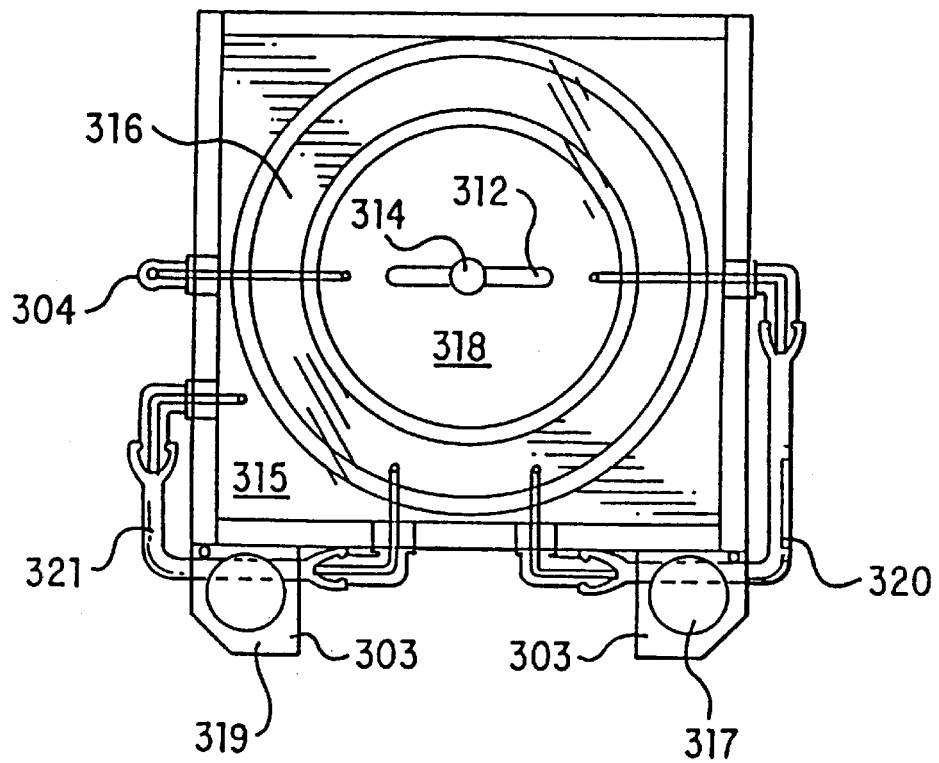

Reservoir R3 is also constructed as a gradient former. The details of reservoir R3 are shown in FIG. 3. Reservoir R3 contains an outer compartment 315 ($R3_3$), an inner compartment 318 ($R3_1$), and a third intermediate compartment 316 ($R3_2$). Intermediate compartment 316 is connected to inner compartment 318 through a fluid conduit 320 controlled by a solenoid 317 ($SR3_1$). Compartment 316 also connects to outer compartment 315 by a fluid conduit 321 controlled by a solenoid 319 ($SR3_2$). The use of an outer compartment is necessary when concentration is being reduced to zero or nearly zero, for reasons noted below in the discussion of the function of the gradient pump and the action of the gradient formers. The use of an outer compartment is greatly preferred compared to a middle compartment having a larger volume of fluid (and no outer compartment) because simply increasing the volume of fluid in the middle compartment would cause the concentration profile resulting from a constant gradient pump 132 flow rate to become non-linear. Control of concentration-time history would then become more complicated. More importantly, an excessive amount of fluid in the middle compartment would be required to approach a zero concentration in the circuit compared to the amount of fluid required in the outer compartment after virtual emptying of the inner and middle compartments.

Automated use of reservoir R3 poses some problems which are successfully addressed in part by software and in part by the specific construction of R3. Specifically, actuation of solenoid $SR3_2$ allows fluid in the outer compartment ($R3_3$) to flow first into the middle compartment ($R3_2$) and from this compartment to the inner cylinder ($R3_1$). This is because the pressure head present between $R3_3$ and $R3_2$ is large when $R3_1$ and $R3_2$ are nearly empty, which occurs when $SR3_2$ is activated. At this point, $R3_3$ is still full. This large pressure head causes fluid to flow too rapidly into $R3_1$ if $R3_3$ is connected directly to $R3_1$ rather than using $R3_2$ as a buffer between $R3_3$ and $R3_1$. By adjusting the level of $R3_3$, the flow can also be partially controlled. But even with these two precautions, further control of flow is required by using an appropriate duty cycle for $SR3_2$. The flow to $R3_1$ should be slow at first and more and more rapid as the concentration is brought closer and closer to zero, whereas passive flow under the influence of gravity will always be fastest at first and slowest at the end unless the flow is metered by the sort of tailored duty cycle currently being imposed on $SR3_2$.

The other modifications to R3 resemble those of R1.

Reservoir R4 is a gradient former constructed in the same manner as R1.

The purpose of the gradient pump 132 is to remove some of the recirculating fluid from the circuit. This removal of fluid causes the flow rate of fluid back to the reservoir of origin to be less than the flow rate of fluid from this reservoir to the circuit. This causes the level in the inner cylinder of the reservoir (R1, R3, or R4) to go down. This lowering of inner cylinder fluid level in turn causes the fluid in the outer or middle compartments to flow into the inner cylinder to keep the two levels similar. Thus the two dissimilar concentrations in the two cylinders are mixed in the inner cylinder, generating the concentration gradient which is then sent to the rest of the circuit. This is the manner in which the gradient pump effects the desired gradual changes in concentration which reach the organ and the refractometers. Any necessary adjustments to the gradient pump speed are made by the computer.

The principle involved is that of an ordinary linear gradient former in which the portion of the circuit external to the gradient former can be regarded, to a first approximation, as extra volume in the inner cylinder. Withdrawal and discard of fluid from the inner cylinder at a constant rate will result in a linear molar concentration change with time despite the presence of the rest of the circuit and the recirculation of fluid back to the reservoir. However, unlike an ordinary gradient former, the concentration of fluid leaving the gradient former at the moment the volume in the gradient former becomes zero will not be equal to the concentration of fluid in the outer (or middle) cylinder of the gradient former. Therefore, in order to approach a concentration of zero during cryoprotectant washout using an ordinary two-compartment gradient former, it is necessary to add additional fluid to the outer cylinder while continuing to discard fluid from the inner cylinder normally. This is why R3 has been modified to have a third compartment. The extra fluid required to continue cryoprotectant washout is added from this third compartment by the computer more accurately than a human operator could accomplish this task manually. During introduction of cryoprotectant, on the other hand, the desired final concentration can always be reached by using a concentration in the outer compartment which significantly exceeds the final concentration desired in the circuit at the end of the gradient. Since the current method involves an upward step change in concentration (see below), it is convenient to fill R1's outer compartment with the same fluid used in R2.

The HBM heat exchange system is shown in detail in FIGS. 4A–E.

Perfusate enters the HBM through an entry port 403, travels through a central channel 400, and leaves the HBM via an outlet port 406. On either side of the central perfusate path are separate chambers for regulating temperature. The two innermost temperature control chambers 401 (one on each side of the perfusate path) are used for the circulation of coolant, while the outer chambers 402 are a pathway for the flow of room temperature fluid for offsetting the coolant. (For specialized applications involving, for example, normothermic perfusion, these pathways can be reversed.)

The direction of cold fluid flow is optional. Adequate temperature control has been found when all fluids (perfusate, coolant, and warming fluid) flow in the same direction (uphill) despite the lack of countercurrent heat exchange. This mode allows the avoidance of air or carbon dioxide accumulation in the outer chambers.

Perfusate enters the bottom of the HBM unit through inlet 403 and travels upward in a zig zag pattern. It emerges into a small upper reservoir which has an air space above: this is the bubble trap area 404. Perfusate then travels beneath the bubble trap and goes through a perfusate mixing area 405 before finally traveling onward to the arterial outlet.

The inlets for cold 407 and warm 408 fluid are each split into two channels within the base of the unit. The outlets 410, 411 for warm and cold fluid, respectively, each receive fluid collected from two channels such that each channel of the same kind (i.e., each cold channel or each warm channel) is the same length and nominally experiences the same pressure difference from start to finish, so that flow rate through each like channel should be approximately equal.

All of the cold and warm fluid pathways include a length of flexible tubing 412 at the rear of the unit. These tubing segments serve two purposes. First, by introducing an air gap between the four channels, heat exchange between them is minimized. This is particularly desirable when all of the cold and warm fluid is flowing in the direction opposite to that of perfusate flow (i.e., in ortho grade direction) and has not already undergone heat exchange with the perfusate. Second, each tube can be clamped. In this way, if by chance one cold channel or one warm channel should take all of the cold or warm fluid delivered while the other channel "airlocks", this situation can be corrected by clamping the channel receiving all of the flow and purging the air out of the inactive channel, bringing each channel into full function and equal flow.

Because in the orthograde mode the temperature conditioning fluid enters the heat exchanging portion of the unit at the top and exits at the bottom, it is necessary upon installation to run the cold and hot pumps in retrograde direction in order to purge all air out of the cold and warm channels. This is best accomplished if the cold and warm tubing leading to and from the bath is no more than about ⅛ inch in internal diameter, since at this diameter fluid flow will displace air from the tubing rather than allowing it to flow uphill in a direction opposite to the direction of fluid flow or otherwise to remain unpurged in various parts of the tubing. Thus, when the pump direction is reversed again from retrograde to orthograde, no air will be present in the tubing and none will be trapped in the heat exchange chambers of the unit.

In addition to serving a heat exchange function, the zig zag pattern is also designed to force mixing of previously perfused dense perfusate or, when perfusate density is rising rather than falling, to purge the less dense perfusate from the perfusate path.

As the perfusate emerges from the zig zag heat exchange area, it enters the bubble trap 404 at trap entry area 418. Perfusate exits the bubble trap through exit region 419. The zig zag pattern, in fact, is also designed to allow any air bubbles to exit the heat exchange area and to emerge into the bubble trap area. The bubble trap area is designed to have the following features.

1. Its volume is sufficiently large to reduce the pulsatile action of the perfusion pump to a minimum by distributing the shock of each stroke over a relatively large air volume.

This simplifies pressure control and measurement and may be less damaging to the organ.

2. Its volume is sufficiently low to minimize the liquid volume present in the trap and thereby to minimize the dead time and dead volume between the organ pump and the organ itself. A minimal volume is also desirable to minimize layering of more dilute perfusate over more dense perfusate.

3. A pressure sensing port 413 is provided. Port 413 has no fluid connection to the perfusate, thus eliminating a "blind alley" in which fluid cannot be mixed properly or in which disinfectant might fail to penetrate or might be trapped. Both an electronic pressure transducer (to provide a signal to the computer) and a sphygmomanometer gauge (for calibration and visual checking) are used.

4. The lid 414 of the trap is removable for cleaning.

5. A vent port 416 is provided which is used to adjust fluid level in the trap so as to make it the minimum required to serve the bubble trap function and to maximize pressure wave damping. The tubing from this vent leads to the outside of the cabinet, permitting adjustments to be made without opening the cabinet door.

6. A third port 417 is provided through the bubble trap lid to permit the injection of drugs, vascular labeling materials, fixative, etc.

7. The walls of the bubble trap are angled near the trap entry and exit points 418, 419, respectively, to produce a certain amount of mixing of the perfusate both as it enters and as it leaves the trap, and to break up and minimize the volume of layers of dilute perfusate overlying more dense perfusate.

8. The option exists of introducing probes, such as a temperature probe via one of the ports in the trap lid to make measurements in the perfusate without permanent embedding of the sensor: the port consists of flexible tubing attached to a plastic threaded fitting. A probe can be freely admitted or withdrawn and the tubing clamped with hemostats or an equivalent clamp to effect a pressure-tight seal. This simplifies removal and reinstallation of the HBM when it must be cleaned and allows flexibility in probe selection and the opportunity of using the probe for other measurements elsewhere.

Figure 4C:
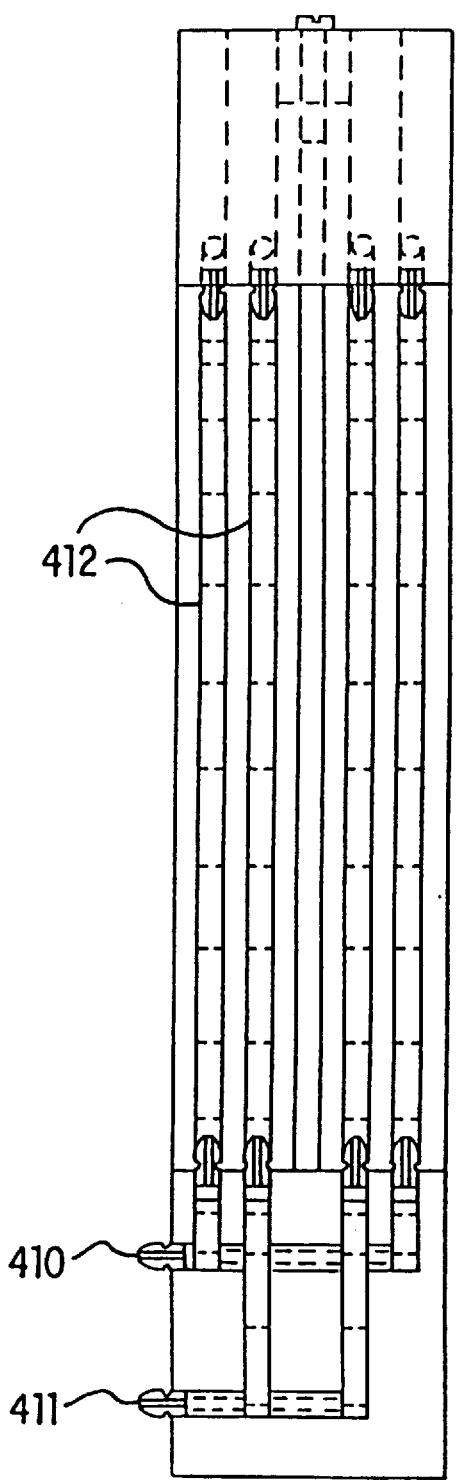
Figure 4D:
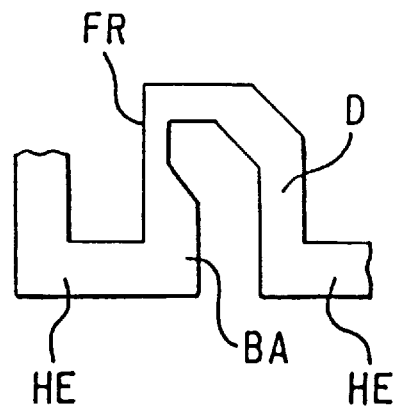
FIG. 4D shows the basic mixing unit area of the HBM.
Figure 4E:
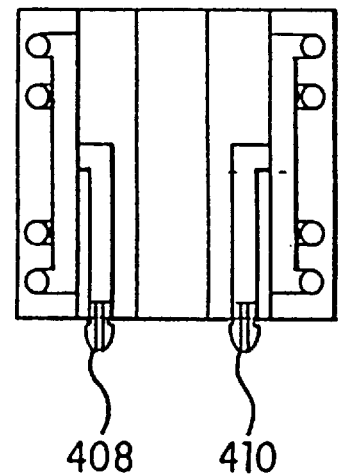
FIG. 4E shows a top view of the base of the HBM.

After leaving the bubble trap, the perfusate descends to a mixing area 405 (see FIG. 4D). The basic unit of the 3-unit mixing path is a narrow horizontal entry area HE emerging into a "wide" basal area BA which rises to an area of flow restriction FR and ends in a descent D to the next horizontal entry area. Fluid entering HE is forced through an opening too small to support much layering of low density fluid on top of high density fluid, especially considering the right angle turn required just before HE. Fluid flowing into BA may, if less dense, rise immediately upward toward FR. If more dense, it may be driven into the wall and rise upward along this wall. Upon encountering FR, however, the denser liquid will be accelerated toward the less dense liquid rising directly from HE, creating turbulence and mixing. If BA fills with dense perfusate, again the speed of the fluid flowing directly upwards at FR should cause the dense liquid to mix with any low density fluid layered above FR. Furthermore, the narrow descending path D should draw layered liquid down the angle along with denser liquid, again preventing stagnant layers from persisting. In practice, three such mixing units aligned in series as shown in FIG. 4B are sufficient to mix initially very poorly mixed perfusate, which is encountered frequently in the course of abruptly raising or lowering cryoprotectant concentration. One final function of the mixing units is to serve as a trap for any small bubbles which for any reason are not removed in the bubble trap area. (Bubbles in the mixing area are, however, easily purged by the operator prior to initiation of organ perfusion.)

After leaving the mixing region, the perfusate descends to an outlet port 406 leading directly to the organ. The path from the final mixing unit to port 406 is deliberately created at an angle to the horizontal in order to provide one last chance of stopping any bubbles from reaching the organ, since in order to reach the organ a bubble in this pathway would have to flow downhill, contrary to its tendency to flow uphill.

The mixing area and subsequent areas are purged of air by occluding the outlet tubing affixed to port 406 with the vent open until approximately ½ inch of fluid has accumulated in the bubble trap. The vent is then closed until the pressure has reached about 60–120 mmHg. Finally, fluid is once again allowed to flow freely through port 406. The jet of fluid through the mixing area and out port 406 sweeps all air out of the fluid path from the bubble trap to port 406. If some air persists, it can be removed by repeating the process. After air has been purged, the vent is opened to allow unnecessary fluid in the bubble trap to exit the trap under the influence of gravity, reaching a final depth of about ⅛ inch. A final depth of ⅛ inch cannot be set before purging the line of air because insufficient volume exists to avoid refilling the mixing area with air from the bubble trap during the purging process.

The HBM is designed to require removal for cleaning only infrequently. Disinfection and removal of disinfectant from the bubble trap area is effected automatically but presently requires some operator attention afterwards to ensure that all uppermost exposed surfaces are disinfected and later washed free of disinfectant without contaminating the outlet tubes. The option exists of arranging the outlet tubes at 413, 416, and 417 in such a way that, with specific solenoids attached to them, they could be individually purged with water, disinfectant, and air under automated control, thus relieving the operator of the need for diligence in cleaning the bubble trap.

After the perfusate exits the HBM unit through port 406, it enters the organ in the organ container 122 (FIG. 1). In the preferred embodiment, the organ container comprises a rectangular box with a hinged lid, lid stop, lid handle, sloped floor, specially sloped feet, arterial and venous thermocouple inlets, perfusate inlet, and effluent outlet in the foot opposite the inlet. The slope of the floor is downward in both the right to left and the back to front directions to ensure that all fluid runs to the foot outlet with very little fluid accumulation anywhere in the container. One needle probe is inserted directly through the wall of the arterial line. A second probe is placed directly in the stream of fluid emerging from the organ. In typical results, the arterial and venous temperatures differ by only tenths of a degree, but both are useful for quality control. The organ container may employ a soft mesh support for the organ similar to that used in the MOX-100 DCM™ organ cassette (Waters Instruments Inc., Rochester, Minn.) or the organ can be placed directly on the floor of the organ container or on a specially designed independent and removable support. The latter option is preferred and is presently in use.

The organ container 122 and the organ pump 108 are placed in maximum proximity to reduce dead times and dead volumes between the two, and the tubing leading from the organ pump to the organ container is chosen to be as small in inner diameter as possible for the same reason.

Most perfusate does not go through the organ loop L2 as described above but travels instead from the filters to the in-line analog refractometer 106. The presently preferred embodiment of the invention uses a modified commercially available refractometer from Anacon Inc. (Burlington, Mass.). In particular, small diameter tubing inlet and outlets are used rather than the very large standard Anacon pipe fittings.

The modification of the refractometer sensing head appropriate for the final invention could also contain the following additional changes from the ordinarily available Anacon unit.

1. The internal volume of the fluid path could be further minimized.

2. Presently, it is necessary to purge the air space of the unit with a slow flow of dry nitrogen gas to prevent condensation of moisture due to the low temperatures and high humidities prevailing in the cabinet. In a modified version, the electronics area of the sensing device could be hermetically sealed with some desiccant inside to eliminate the need for a nitrogen purge.

3. The present unit must be oriented with the fluid flow direction being vertical and upwards. However, the unit is not built to be used in this orientation, and body changes could be made to adapt the unit's shape to this orientation.

The invention allows the operator to access reservoirs in any sequence and to otherwise custom-design the process which may be of interest. The operator is even free to switch solenoid positions depending on what he may want to do. Nevertheless, the following nominal application illustrates the actuation patterns required to deliver fluid from and to each individual reservoir and filter. It also illustrates the "standard protocols" for organ cryoprotectant perfusion and for cleaning of the system which the system was designed primarily to carry out.

Solenoid S1 admits fluid from R1 when off, or from R2 when activated. Solenoid S2 is open to R3 when not energized, or to R4 when energized. The output of S1 and S2 is to S3, which accepts fluid from S1 (that is, from R1 or R2) when in the resting state and which accepts fluid from S2 (i.e., from R3 or R4) when activated. The common outlet for S3 (always open) leads to the circuit pump 102, which then withdraws fluid from the solenoid-selected reservoir.

If differential filters are to be included, then the output of the circuit pump 102 is to S4's common port (always open). When S4 is not energized, its output is directed to filter F1. The return from filter F1 returns to the normally open port of S5 and exits through the S5 common outlet to the refractometer loop L1 and the organ loop L2. If, on the other hand, S4 is energized, then its output is directed to the common inlet port of S6. When S6 is in the resting state, its output is directed to filter F2, and the return from filter F2 enters S7 through its normally open port. The output from S7 travels to the normally closed port of S5, which must be energized to accept this output. Once fluid has entered S5, it flows out the S5 common outlet to the refractometer loop and the organ loop. Finally, if S4 is energized and S6 is also energized, fluid will be directed through both of these valves and will reach filter F3. The return from filter F3 occurs via the energized S7 and the energized S5 solenoids and goes to the two loops L1 and L2 as above. As noted earlier, the use of filters F2 and F3 and therefore of solenoids S4, S5, S6, and S7 is optional and will be useful primarily when very abrupt changes from one solution to another are required, or when particularly heavy particulate contaminates must be removed.

Effluent from the organ eventually returns to S8. If S8 is activated, the fluid is discarded. If S8 is not activated, the fluid is directed from S8 to combine with fluid from the refractometer loop and is returned to a desired reservoir.

Fluid traveling through the refractometer loop travels successively to solenoids S9, S10, S11, and S12 and then to the waste line if none of these solenoids are energized. Energizing S9 diverts flow to the R1 recirculation line. S10's activation (in the absence of activation of S9) diverts flow to R2. Similarly, selective activation of S11 or S12 will, respectively, recirculate fluid to R3 or R4.

There are two basic processes of solenoid-actuated fluid control, one for actual perfusions and one for system cleaning and priming. The perfusion process typically proceeds from R1 through R4 whereas priming must occur in the reverse order to load the fluid uptake and fluid recirculation lines for reservoirs R2–R4, particularly if filters F2 and F3 and their associated lines are used, leaving the circuit primed with fluid from (typically) R1 (or C1) at the end of the priming (or cleaning) process. The typical sequence of solenoid activations required to prime the complete system (or to clean it) is listed in tabular form below.

SOLENOID CONTROL SEQUENCE FOR STANDARDIZED RINSING/PRIMING

The conditions of the solenoid control processes are set forth in Tables 1 and 2. The uses of these control processes are to: replace perfusate with filter-sterilized $H_2O$ at the end of the process; replace cleaning $H_2O$ with chemical sterilant between perfusions; remove disinfectant using filter-sterilized distilled $H_2O$; remove water using air; remove air using reservoir fluid, i.e. prime the system.

When only F1 (not F2 or F3) is present, priming (and cleaning) may proceed in any order of reservoirs, provided, in the case of priming, that the final reservoir corresponds to the first reservoir used for the subsequent perfusion. Applicants now use a procedure involving momentary aspiration from R2, then R3, then R4, then R1, taking just enough time to prime U2, U3, U4, and U1, respectively, followed by computer/user interactive activation of S12, S11, S10, and S9 to allow manual filling of RL8, RL7, RL6, and RL5 by syringe with retrograde exhaust via P1, because this procedure saves large quantities of perfusate and is fast.

The standard process of solenoid actuation for withdrawing fluid from R1–R4 and for creating gradients for a normal perfusion is as follows (assuming (1) use of optional filters F2 and F3, (2) straightforward or typical use of the gradient-controlling solenoids, and (3) the existence of a gradient former as R2). The staged completion of a closed circuit upon going from one reservoir to another is to avoid recirculating solution of undesired composition to the new reservoir before its contents have displaced the previous solution from the circuit. If there is no problem with recirculating the previous solution, the precaution of delayed recirculation can be dropped.

TABLE 1

| | | Solenoid # (+ = Energized) | | | | | | | | | | | | |
|---|---|---|---|---|---|---|---|---|---|---|---|---|---|---|
| Sub-Task Accomplished | 00*0* | 1 | 2 | 3 | 4 | 5 | 6 | 7 | 8 | 9 | 10 | 11 | 12 | 13 |
| 1. Deliver fluid from R4 through F1 | | − | + | + | − | − | − | − | − | − | − | − | − | ** |
| 2. Perfuse R4 recirculation tubing to W4 | | − | + | + | − | − | − | − | − | − | − | − | + | − |
| 3. Deliver from R3 through F3 | | − | − | + | + | + | + | + | − | − | − | − | − | ** |
| 4. Perfuse R3 recirculation tubing to W3 | | − | − | + | + | + | + | + | − | − | − | + | − | − |
| 5. R2, F2 | | + | − | − | + | + | − | − | − | − | − | − | − | ** |
| 6. R2 recirculation tubing to W2 | | + | − | − | + | + | − | − | − | − | + | − | − | − |
| 7. R1, F1 | | − | − | − | − | − | − | − | − | − | − | − | − | ** |

TABLE 1-continued

| | Solenoid # (+ = Energized) | | | | | | | | | | | | | |
|---|---|---|---|---|---|---|---|---|---|---|---|---|---|---|
| Sub-Task Accomplished | 00*0* | 1 | 2 | 3 | 4 | 5 | 6 | 7 | 8 | 9 | 10 | 11 | 12 | 13 |
| 8. R1 recirculation tubing to W1 | − | − | − | − | − | − | − | − | − | + | − | − | − | − |
| 9. Organ loop discard tubing*** | − | − | − | − | − | − | − | + | + | − | − | − | − | − |

*If the sequence above is to be done with reservoir fluid, S0 and SS00 will be off. S0 and S00 will also be off if the sequence above is to be done with water, and the cleaning ports C1–C4 will be connected to uptake lines U1–U4. If the sequence above is to be done with disinfectant, S0 will be off and S00 will be on. If the sequence is to be done with air, S0 will be on and S00 will be off.
S13 (and, optionally, S14 and S15), the filter vent solenoid(s), will be on for a portion of this step and off for the remainder of this step: it will be on just long enough to purge air from the line (usually 60 sec. on step 1 and 30 sec on each of the remaining steps for which the  notation is used). This can be programmed not to happen if the filters are not present in the system.
***this step is omitted when priming the system.
Note:
Water control solenoid S16 is on (waste tube open for disposal of fluid to waste) for steps 2, 4, 6, 8, and 9 but off for all other steps.

TABLE 2

Solenoid Control Sequence For Standard Perfusion

| | Solenoid # (+ = Energized) | | | | | | | | | | | | |
|---|---|---|---|---|---|---|---|---|---|---|---|---|---|
| Sub-Task Accomplished | 00*0* | 1 | 2 | 3 | 4 | 5 | 6 | 7 | 8 | 9 | 10 | 11 | 12 |
| 1. Initial recirculation to R1 | − | − | − | − | − | − | − | − | − | + | − | − | − |
| 2. R1 gradient | Same as 1, but activate SR1 | | | | | | | | | | | | |
| 3. From R2 just to F1, no recirculation** | + | − | − | − | − | − | − | − | + | − | − | − | − |
| 4. Deliver R2 first solution through F2, no recirculation | + | − | − | − | + | + | − | − | + | − | − | − | − |
| 5. Recirculate R2 solution except from organ | + | − | − | − | + | + | − | − | + | − | + | − | − |
| 6. Recirculate all R2 solution | + | − | − | − | + | + | − | − | − | − | + | − | − |
| 7. Run a gradient from reservoir R2‡ | Same as 6, but activate SR2 | | | | | | | | | | | | |
| 8. Perfuse from R3 just to S6/F2** | − | − | + | + | + | − | − | + | − | − | − | − | |
| 9. Perfuse from R3 to F3, circuit open | − | − | + | + | + | + | + | + | − | − | − | − | |
| 10. Recirculate to R3 through F3, circuit partially open | − | − | + | + | + | + | + | + | − | − | + | − | |
| 11. Recirculate all R3 fluid | − | − | + | + | + | + | + | − | − | − | + | − | |
| 12. Run first part of R3 gradient | Same as 11, but activate SR31 | | | | | | | | | | | | |
| 13. Run second part R3 gradient*** | Same as 11, plus SR31 and SR32 | | | | | | | | | | | | |
| 14. Open circuit, perfuse from R4 through F3 | − | + | + | + | + | + | + | + | − | − | − | − | |
| 15. Recirculate to R4 except from organ | − | + | + | + | + | + | + | + | − | − | − | + | |
| 16. Recirculate from both loops to R4 | − | + | + | + | + | + | + | − | − | − | − | + | |
| 17. Run R4 gradient | Same as 16, but activate SR4 | | | | | | | | | | | | |

*For normal perfusions, solenoids S0, S00, and S13–S16 will always be non-actuated.
**This step prevents fluid from the previous reservoir, which is initially present in the line between the new reservoir and the filter that had been previously equilibrated with fluid from the new reservoir, from contaminating the previously equilibrated (new) filter.
***As noted in the discussion, SR32 activation must follow a duty cycle initially, ending in permanent activation of SR32 until end of use of R3. The duty cycle involves switching back and forth between solenoid patterns 12 and 13 as dictated by the duty cycle requirements.
‡Step 7 is optional.

The number of reservoirs could be less than or greater than the number specified here, with corresponding changes in solenoid number. Furthermore, the number of layers of R1–R4 need not conform to the descriptions given above. The limits would be one reservoir at the least and perhaps eight reservoirs at the maximum, in which any reservoir could have from one to four compartments. The upper limits are based partly on volume and crowding constraints and partly on the improbability of any procedure complex enough to require more than 8 reservoirs for its control.

Another variation would be to employ different capacity reservoirs at different positions (e.g., instead of the herein preferred embodiment, one might have a 2-liter reservoir followed by a one-liter reservoir followed by a 3-liter reservoir followed by a one-liter reservoir, and so on).

In principle, the use of individual reservoirs could be abandoned in favor of one multi compartment reservoir consisting of perhaps four to twenty concentric cylinders each activated by solenoids or even by manual levers external to the temperature-controlled area, all stirred by a single central stir table. Abrupt or step changes in concentration could still be accommodated if the stepped change is not delivered via the stirred central area. The relative positions of the reservoirs could also change.

Finally, a fluid metering system could be employed rather than a gradient former. In this system, a pump would deliver concentrated cryoprotectant or diluent to a mixing reservoir rather than relying on gravity. This pump would be computer operated to adjust for departures from the programmed concentration. The gradient pump, however, would be retained in order to control overall circuit volume.

The arterial concentration sensor could be located proximal to, rather than distal to, the origin of the organ loop in the circuit, but should not be located proximal to the filters.

A pressure sensor to sense pressure developing on the circuit pump side of the filters could be incorporated as a warning device.

More generally, the device could be separated into two devices, the first for preparing organs for cryopreservation and the second for preparing previously cryopreserved organs for transplantation. The first device would omit R3 and R4 (and associated solenoids) while the second would omit R1 and R2 (and associated solenoids) while otherwise being substantially the same as the unified device. Given that cryopreservation and the recovery from cryopreservation may occur at different locations and under the direction of different individuals, this variation is likely to be of use under practical conditions. Essentially, these two devices would be identical except for the use of different software and the use of different reservoirs for adding and for removing cryoprotectant. Another usage could involve the unorthodox use of only two reservoirs to accomplish both loading and unloading; for example, loading could be done using R1 and R3 if only the inner compartment of R3 were used (R3 standing in for R2), and unloading could be done using R1 and R3 if R1 substituted for R4.

II. Description of the Methods

A. Preparing an Organ For Cryopreservation and Subsequent Transplantation Into an Animal The complete cryopreservation method using the above-described apparatus comprises several parts. One part consists of the pretreatment of the donor animal and/or the organ prior to its removal from the animal to prepare the organ for its cryopreservation. Another part consists of the choice of the cryoprotective agents. Another part is the actual protocol for perfusing the cryoprotectant into the organ prior to its cryopreservation. Another part is the cryopreservation, storage and warming of the organ using appropriate techniques none of which are part of this invention. Another part of this invention is the protocol for removing the cryoprotectant(s) from the organ after its warming in preparation for transplantation into a recipient. Another part is treatment of the organ and the recipient upon organ transplantation.

1. Pretreatment of the Donor and the Donated Organ in vivo

The donor, in addition to other standard treatments, received an infusion of iloprost (Berlex Laboratories, Inc., Cedar Knolls, N.J.) which is a relatively long-lived analog of prostacyclin ($PGI_2$), or a similar agent, starting 10 to 20 min. before organ procurement. Applicants have found that iloprost was effective in reducing the apparent toxicity of subsequently-administered cryoprotectant after either its intravenous infusion to the systemic circulation or its administration directly into the renal artery. The best mode dose of iloprost was about 25 $\mu$g/kg given by either route, although direct intra-arterial infusion is presently preferred to maximize organ exposure to the agent while minimizing iloprost-mediated systemic hypotensionl. Fifteen $\mu$g/kg was also effective, but was less effective than 25 $\mu$g/kg. Acceptable limits of iloprost concentration for this application are 5–75 $\mu$g/kg, depending on species, organ, infusion rate, duration of infusion, etc. Iloprost was typically infused over the course of 20 min; acceptable infusion duration limits are 1–60 min for cadaveric organ donors. When hypotension is a limiting factor, iloprost may be infused at relatively low concentration over a relatively long time (20–60 min). While not wishing to be bound by any particular theory, iloprost's protective action may not be a direct cytoprotective effect. The ineffectiveness of iloprost in protecting kidney slices from cryoprotectant-induced injury suggests that iloprost may simply act as a powerful vasodilator that facilitates uniform cryoprotectant distribution. Therefore, other vasodilators such as acetylcholine, nitroprusside, nitric oxide, hypertonic and/or hyperoncotic flush solutions etc., may be substituted for it at doses which produce sufficient vasodilation in the organ of interest.

An important option for optimizing results was organ pretreatment with transforming growth factor beta 1 (TGF$\beta$1), which prevented detachment of cultured endothelial cells from their substratum in vitro during superfusion with 52% w/v cryoprotectant, when added to the culture medium at a concentration of 10 ng/ml about 24 hours prior to superfusion. The best mode use is to administer a bolus injection of TGF$\beta$1 of 0.1 $\mu$g to 10 $\mu$g per kg, 2 to 4 hours before organ donation with or without additional injections at earlier times. The inventors found that giving 0.5 $\mu$g/kg of human TGF$\beta$1 at 3, 16, and 20 hours before organ donation protected rabbit kidneys from a 40–50 min exposure to 8M cryoprotectant, thus preventing the otherwise-expected hemorrhage that results from such exposure and allowing one animal (exposed for 50 min) to survive until sacrificed on day 15 postoperatively.

After pre-treatment in vivo, the organ of interest was flushed in situ with cold Euro Collins solution, modified UW solution or a comparably effective solution in such a manner as to avoid conflicts in multiple organ procurement. The compositions of these solutions are contained in Table 3. (Should normothermic preservation techniques supersede hypothermic preservation for hearts, the heart can be flushed with warm rather than cold solution.) The flushing solution(s) should initially contain iloprost (1 $\mu$g/ml in the best mode, acceptable iloprost concentration limits being 0–10 $\mu$g/ml), anticoagulants (e.g., heparin, 10,000 units/liter in the present embodiment, acceptable heparin concentration variations being 500–20,000 units/liter), vasodilators (e.g., papaverine, 40–90 mg/liter in the best mode, 0–90 mg/liter as acceptable limits) and other desired agents. A second flushing solution should be used to wash out all of these agents as cooling and blood washout is completed. The excised organ (except for organs such as the heart that may be best maintained by normothermic perfusion) should be transferred to an iced bath of flush solution and transported to a perfusion machine capable of introducing and removing cryoprotectants in the fashion to be described.

TABLE 3

Compositions of Perfusion Solutions

| | Euro-Collins* | |
|---|---|---|
| Compound | mM | g/l |
| Dextrose | 194 | 34.96 |
| $KH_2PO_4$ | 15 | 2.06 |
| $K_2HPO_4$ | 42 | 7.40 |
| KCl | 15 | 1.12 |
| $NaHCO_3$ | 10 | 0.84 |

*pH = 7.4
*milliosmolality = 350–365 milliosmolal

| | RPS-2 | |
|---|---|---|
| Compound | mM | g/l |
| Dextrose | 180 | 32.43 |
| $K_2HPO_4$ | 7.2 | 1.25 |
| KCl | 28.2 | 2.11 |
| $NaHCO_3$ | 10 | 0.84 |
| Glutathione | 5 | 1.53 |
| Adenine HCl | 1 | 0.17 |
| $CaCl_2$ | 1 | 0.111 |
| $MgCl_2$ | 2 | 0.407 |

TABLE 3-continued

Compositions of Perfusion Solutions (Note:
RPS-2⁻ solution is RPS-2 without $CaCl_2$, and also without $MgCl_2$)

| Modified UW Solution #1 | | | Modified UW Solution #2 | | |
|---|---|---|---|---|---|
| Compound | mM | g/l | Compound | mM | g/l |
| $NaH_2PO_4.H_2O$ | 25 | 3.45 | $NaH_2PO_4.H_2O$ | 25 | 3.45 |
| K gluconate | 100 | 23.42 | K gluconate | 100 | 23.42 |
| hemi Mg gluconate | 1 | 0.21 | hemi Mg gluconate | 1 | 0.21 |
| glucose | 5 | 0.90 | glucose | 15 | 2.70 |
| glutathione | 3 | 0.92 | glutathione | 3 | 0.92 |
| adenosine | 5 | 1.34 | adenosine | 5 | 1.34 |
| HEPES | 10 | 2.38 | HEPES | 10 | 2.38 |
| adenine (hydrochloride) | 1 | 0.17 | adenine (hydrochloride) | 1 | 0.17 |
| ribose | 1 | 0.15 | ribose | 1 | 0.15 |
| $CaCl_2$ | 0.05 | 0.0056 | $CaCl_2$ | 0.05 | 0.0056 |
| HES (g) | — | 50 | — | — | — |

(Note:
Modified UW Solution #2 does not contain HES but contains more glucose than modified UW Solution #1)

2. Cryoprotective Agents: Formulae of the Vitrification Solutions V49, V52, V55, V49B and V55B All perfusion experiments were carried out using solutions designated here by V49, V52 and V55 (V49 has sometimes been referred to as VS4. V55 has been referred to as VS41A.). At low cooling rates (5°–10° C./min) V49 was found to vitrify at 1,000 atm of applied hydrostatic pressure but not at ordinary ambient pressures. V52 was inferred to vitrify at 500 atmospheres (atm) of applied pressure. V55 was found to vitrify at 1 atm.

V49 was composed of dimethyl sulfoxide (D), formamide (F), and 1,2-propanediol (P) such that the mole ratio of D to F was 1:1, the total mass of D+F+P per liter was 490 grams, and the total mass of P per liter was 150 grams. Thus, per liter, D+F=340 grams, F=124.33 grams, and D=215.67 grams. This mixture of cryoprotectants was preferred based on the results described below. Acceptable variations for the proportions of D, F, and P are: D:F weight ratio can be as low as 1.4 and as high as 3.5; for the former, the proportion of P:(D+F) should be elevated to 18:34 and/or the total concentration raised to 50–51% w/v (grains/deciliter) by the addition of extra P.

The formula for V52 was obtained by multiplying the cryoprotectant content of V49 by 52/49, keeping the vehicle solution the same as for V49. The formula for V55 was obtained by multiplying the cryoprotectant content of V49 by 55/49, keeping the vehicle solution the same as for V49. Thus, the total concentration of solutes in V55 was 550 grams/liter vs. the 490 grams/liter of V49. V49B was a variation of V49 in which the 1,2-propanediol content was replaced gram for gram by 2,3-butanediol (levorotatory form or racemic mixture with less than 5% w/w meso form present), and V55B was, similarly, a variation of V55 in which 2,3-butanediol replaced the 1,2-propanediol gram for gram. The total cryoprotectant molarities of V49, V52 and V55 were 7.49, 7.95 and 8.41M, respectively. The molarities of V49B and V55B were slightly lower than those of V49 and V55 due to the greater molecular weight of butanediol vs. propanediol.

While not wishing to be bound by any theory, V49 and V55 appear to be particularly beneficial due to the exceptional ability of formamide to penetrate kidney tissue, the ability of dimethyl sulfoxide to block the toxicity of formamide, the beneficial balance between the three ingredients (maximizing vitrification tendency while minimizing both toxicity and total solute concentration), the lack of a colloid (typical colloid concentrations of about 4–7% w/v elevate viscosity), the extraordinarily slow rate of devitrification of these solutions at appropriate pressures (1,000 atm and 1 atm, respectively), and the good stability of V55 at −135° C. during at least 6 months of storage.

The cryoprotectants used for organ perfusion were adjusted between the limits represented by V49 and V55, depending upon the pressure to which the organ was to be subjected. Balancing an organ's tolerance to high pressures and its tolerance to high cryoprotectant concentrations allowed optimization of the tradeoff between pressure and concentration required to maintain vitrifiability. For example, an organ that cannot tolerate 1,000 atm but that can tolerate 500 atm may be perfused with V52. Concentrations in excess of 550 grams/liter, to a maximum of about 600 grams/liter, may be used when heterogeneous nucleation on cooling is a significant problem, since the nucleation process and the growth of any nucleated ice crystals will be suppressed at these higher concentrations. One example of a situation in which this problem will arise is the vitrification of very large organs such as the human liver that will cool particularly slowly. At elevated pressures, similar proportional increases in solute concentration will be required as the cooling rate is lowered.

Experiments (see results below) with kidney slices indicated that V49B provided viability identical to the viability obtained with V49. V49B may have greater stability than V49. Variations between V49B and V55B are to be used as per the descriptions above for V49 and V55.

All cryoprotectant solutions must contain, in addition to the cryoprotectants themselves, slowly-penetrating solutescomprising the "carrier" or "vehicle" solution for the cryoprotectants. Typical examples would be modified UW solutions, Euro Collins solution, or Renal Preservation Solution 2 (RPS-2) (see Table 3). The best mode method used Euro Collins as the vehicle solution of choice for kidneys, modified UW solution (as per Table 3) as the vehicle solution of choice for the liver, and commercial UW solution (Viaspan®) (E.I. DuPont and Nemours) as the vehicle solution of choice for hearts.

3. Protocol for Perfusing the Organ with Cryoprotectant

Figure 5:
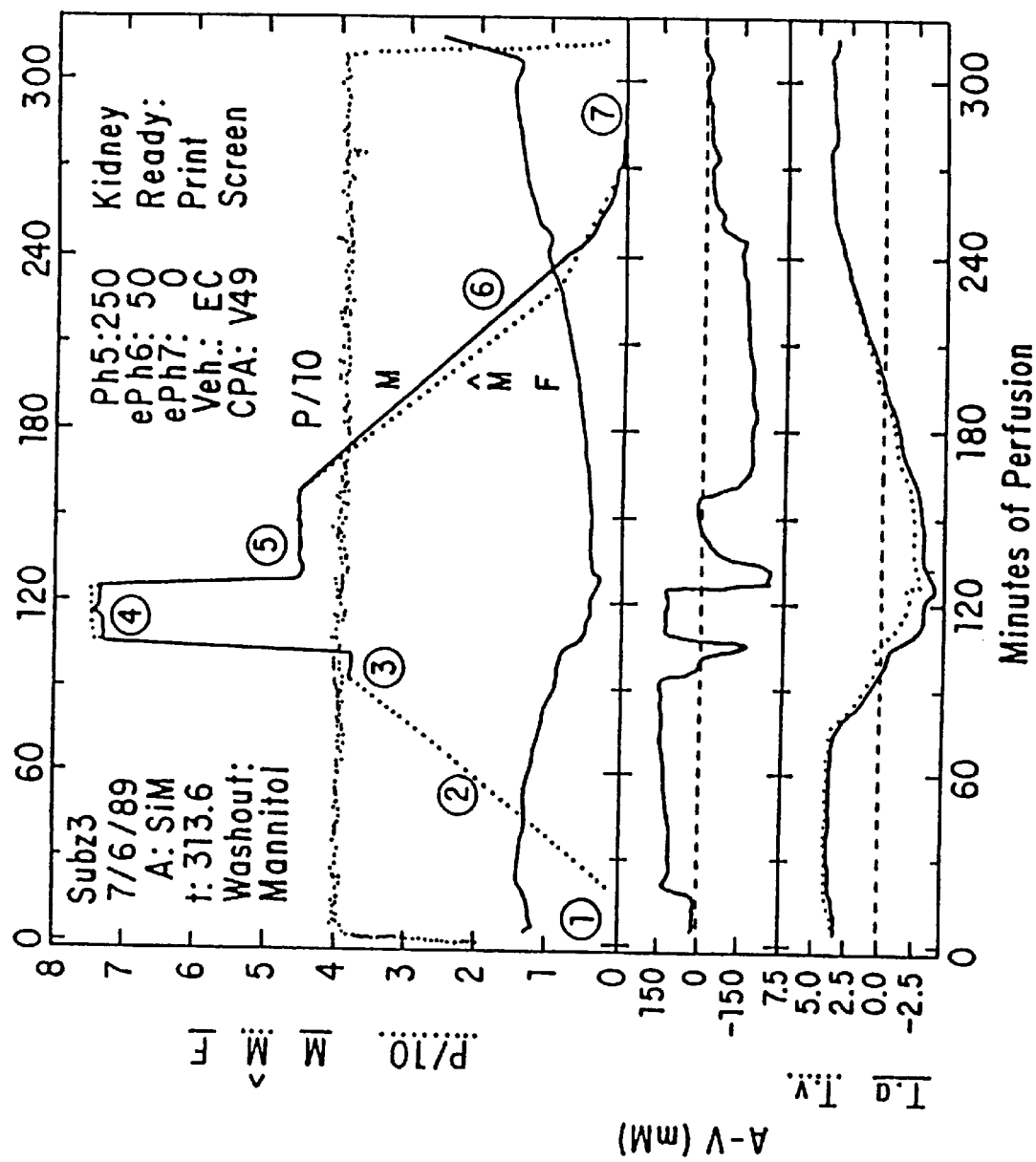
FIG. 5 shows a typical protocol for introducing and removing a relatively dilute vitrification solution. As used in FIG. 5 and in some later figures the following abbreviations have the following meanings.

Typical protocols for cryoprotectant introduction and removal that were shown to yield reliable, high-quality survival of rabbit kidneys after cryoprotectant washout, transplantation, and long-term functional and histological follow-up, are shown in FIGS. 5 and 6 and are additionally described in the flow charts of FIGS. 7A–E. As designated in FIG. 5, the protocols were divided into at least 7 discrete phases. Phase 1 was an equilibration period during which the organ established stable baseline characteristics prior to the introduction of cryoprotectant. Phase 2 was a gradual increase in cryoprotectant concentration that ended in a concentration plateau known as phase 3. After spending a certain amount of time in phase 3, during which time the A-V cryoprotectant concentration gradient usually became approximately zero, the concentration was stepped to a new plateau, this new plateau phase being phase 4. As described in more detail below, phase 4 need not be the highest concentration attained. In FIG. 6, for example, the phase 4 concentration is 6.7M, but the final concentration in the experiment of FIG. 6 was actually 8.4M. Whatever the final concentration, the first washout step is indicated in FIG. 5 as phase 5, another concentration plateau. Phase 6 is the cryoprotectant washout phase and phase 7 is a post-cryoprotectant equilibration phase.

a) Perfusion pressure: The organ was perfused at pressures sufficient to overcome the organ's critical closing pressure but otherwise low enough to avoid needless damage to the vascular tree. For example, the best mode perfusion pressure for the rabbit kidney was 40 mm Hg without significant pulsation. A desirable range of acceptable pressures has been found to be 20–70 mm Hg for different organs and species, including man, except for the liver. The liver normally receives most of its flow through a vein at a pressure typically below 10 mm Hg. Rat livers perfused at 5 mm Hg were able to achieve approximate osmotic equilibration after perfusion with V49 for 20 min when no colloid was present, and half of these livers supported life after transplantation. Consequently, the pressure limits for livers are 5–40 mm Hg through the portal vein, and 5–70 mm Hg through the hepatic artery.

b) Initial perfusion (phase 1): In the best mode protocol, perfusion was first carried out for 15 min to establish baseline values for vascular resistance and calibrations (for pressure and refractive index); to ensure complete blood washout; and to thermally equilibrate the organ, here the rabbit kidney or the rat liver. Clinically, the initial perfusion time is arbitrary, and can be adjusted (from zero minutes to 1–2 days or more) to meet the requirements of the organ procurement and transportation process. In Applicants' laboratory, the perfusate in this period was Euro Collins solution or RPS-2 for kidneys and a modified UW solution for livers. However, this initial perfusate could also be another stabilizing solution in a clinical setting depending upon the needs of the hospital or procurement team.

c) Initial temperature: The initial perfusion temperature required for the procurement and transportation of an organ, such as, for example, the kidney, need not be identical to the perfusion temperature established during phase 1. For example, while most organs may be shipped while surrounded by crushed ice at 0°C., other organs may be shipped while being perfused at normothermia (37° C.). When organs are ready for cryoprotectant administration, however, a preselected, standardized perfusion temperature is established. In the best mode, the initial perfusion temperature was 3.5°–4° C., and the acceptable limits were 0°–15° C. The inventors consider that organs requiring normothermic perfusion for best long-term maintenance can nevertheless be cooled to within this same temperature range and can be treated in a manner similar to that of hypothermically-preserved organs without damage within the relatively short times required for this method.

d) Phase 2: Following the initial baseline perfusion, cryoprotectant concentration was elevated at a constant rate until a first plateau of concentration was established. When using a V49-type mixture of cryoprotectants, the proportions of different cryoprotectants in the mixture were held constant while the total concentration was allowed to change. The rate of increase in total concentration for V49-type solutions was set to about 51 mM/min (nominally 3M/hr) in the best mode for the kidney, acceptable variations being 31–150 mM/min. These rates were considerably in excess of the 30 mM/min rates used by known techniques for glycerol and propylene glycol which were considered to be unnecessarily and undesirably slow for most applications of the method. Linear elevation of concentration promoted equilibration without creating unnecessarily large osmotic stresses.

e) Temperature reduction during phase 2: The temperature was lowered during phase 2 to protect the kidney from the chemical toxicity of the cryoprotectant. In the best mode, the temperature reduction began as the arterial cryoprotectant concentration reached 1.3M; acceptable limits are 0.5M to 3.5M. Temperature descent was terminated as phase 3 was reached. The concentration change during cooling was about 2.5M in the best mode but may vary from about 1M to 4.4M.

As noted above, the initial perfusion temperature should be between 0° C. and 15° C. The temperature after cooling should fall within the range of –13° C. to +5° C. and the total temperature drop during cooling should be between 2° C. and 25° C. Cooling should not continue to below the freezing point of the organ. In the best mode, the final arterial temperature was –3° C., representing a fall of 6.5° C. from the initial temperature and a cooling rate of about 0.33° C./min. The overall cooling rate should not exceed 3° C./min in order to provide adequate opportunity for cryoprotectant diffusion and in order to avoid possible thermal shock to the organ.

f) Phase 3: The phase 3 plateau was set in the best mode for the kidney at 25% w/v total cryoprotectant (250 grams/liter, or about 3.8M) when 40–49% w/v cryoprotectant was to follow, or 30% w/v, (4.6M) when higher concentrations (e.g., V55) were to follow, acceptable variations being 20–40% w/v or w/w. The phase 3 plateau was set to a level that was close to half of the phase 4 concentration. Lower phase 3 levels will increase osmotic stress upon moving to phase 4, whereas substantially higher phase 3 levels will produce increased toxicity due to longer exposure times to concentrated cryoprotectant. The duration of phase 3 was set to about 10 min in the best mode procedure, acceptable variations being 5–30 min, depending on perfusion pressure (and thus organ flow rate), vascular resistance, organ permeability to cryoprotectant, and the rapidity of toxic responses. The duration was long enough to allow the organ to at least approximately osmotically equilibrate with the arterial perfusate, as indicated by an arteriovenous concentration difference no greater than 50–200M, so as to minimize unnecessary osmotic stress during the subsequent jump to higher concentrations.

g) Perfusion with vitrification solution by a one-step, two-step or three-step method: A step change in concentration from phase 3 to phase 4 was necessary to control the exposure time to highly concentrated cryoprotectant. The phase 4 concentration may be sufficient for vitrification (a one-step introduction method) or it may be insufficient for vitrification (requiring one or two additional steps to achieve vitrifiability).

The concept behind the two- (and the three-) step approach is illustrated schematically in FIG. 8. In the "one-step" approach, all of the cryoprotectant was added in one continuous process (C1), and cooling to cryogenic temperatures then occurred in one step (T1) as well. In the "twostep" approach, part of the cryoprotectant was added in the first step (C1), and the rest of the cryoprotectant was added in a second step (C2) carried out at temperatures near the freezing point of the solution used in the first step. In this approach, cooling also took place in two steps, the first step (T1) having been used to prepare for the second concentration increment (C2), and the second step (T2) being used to cool the organ to cryogenic temperatures. In practice, the first cooling step was preferably to temperatures somewhat above the nominal freezing points to guarantee the avoidance of crystallization prior to introducing higher concentrations of cryoprotectant.

In the best mode, the phase 4 concentration was set to 40% (6.1M) to 44% (6.7M) w/v V49 solutes, a concentration that was not sufficient for vitrification (FIG. 6). Acceptable variations for sub-vitrifiable concentrations are 30% w/v to 48% w/v V49 solutes or their equivalent. For the one-step introduction, the phase 4 concentration may range from 480–600 grams/liter (about 7.4–9.2M) for V49- or V49B- type solutions (for example, see FIG. 5). For non-V49/V49B type solutions, the method limits for phase 4 are 35%–60% w/v cryoprotectant.

Phase 4 concentration was held steady for 20 min in the best mode, acceptable variations being 10–60 min. The concentration should be held steady long enough for the organ to closely approach osmotic equilibrium with the perfusate according to the above-described criterion.

For the two step approach, the organ was removed from the perfusion machine after the completion of phase 4, and was cooled by being placed into precooled vitrification solution for 5–30 min (5 min in the preferred mode for rabbit kidneys, longer for more massive organs) prior to being perfused with the vitrification solution. In the best mode, the organs were cooled toward and subsequently perfused at a temperature of $-22\pm2°$ C. (if previously perfused with 6.1M cryoprotectant) or $-25°\pm2°$ C. (if previously perfused with 6.7M cryoprotectant). The temperature chosen at this step will be referred to as the "low temperature perfusion temperature." More generally, the low temperature perfusion temperature may range from $-5°$ C. to $-35°$ C.

One embodiment of the apparatus used for perfusing organs at the low temperature perfusion temperature (to accomplish step C2 in FIG. 8) is illustrated in FIG. 9. In another embodiment, the cooling and low-temperature perfusion are carried out inside the primary perfusion machine without substantial operator intervention.

The inventors have perfused rabbit kidneys with V52 at $-22°$ C. or with V55 at $-25°$ C. at a perfusion pressure fluctuating between 20 and 40 mm Hg but usually not exceeding 30 mm Hg, having obtained excellent results after subsequent transplantation. Acceptable method limits for perfusion pressure range from 50% to 150% of the previous pressure in the perfusion apparatus for organs other than the liver, or from 50% to 400% of the previous perfusion pressure in the case of the liver.

The time required for equilibration with vitrifiable concentrations at the low-temperature perfusion temperature was determined in the case of the kidney by collecting "urine" produced during the low-temperature perfusion and determining its osmolality after suitable dilution. The kidney was deemed to have been equilibrated when the osmolality of the urine approached the osmolality of the arterial perfusate. For other organs, the extent of equilibration is determined as usual by the arteriovenous concentration difference. Acceptable equilibration times were determined to range from about 20 to about 60 minutes.

Another embodiment that will apply to organs which cannot tolerate exposure to fully vitrifiable solutions at the low-temperature perfusion temperature is the three-step introduction method. These organs may be successfully cryopreserved by perfusing a less-than-fully-vitrifiable concentration at the low-temperature perfusion temperature (step two), which concentration, being higher than the concentration used prior to cooling to the low-temperature perfusion temperature, will depress the freezing point of the organ to substantially (i.e., 3° to 20° C.) below the low-temperature perfusion temperature. The organ can then be perfused with fully vitrifiable concentrations near the new organ freezing point temperature (step three), at which temperature the fully vitrifiable concentrations will be sufficiently non-toxic as to be tolerated. This embodiment will apply also to organs that require it for avoiding cooling injury.

h) Rationale for the two-step best mode method: While not wishing to be bound by any theory, the main rationale for the best mode two-step method was the avoidance of cooling injury. Introducing cryoprotectant at the low-temperature perfusion temperature was hypothesized to reduce cryoprotectant toxicity as well.

The inventors discovered that kidneys perfused at $-3°$ C. with V49 survived 100% of the time (14 survivors out of 14 perfusions) but when they were cooled to $-30°$ C., warmed and washed out using the best techniques known at the time, the survival rate fell substantially (see FIG. 13). Kidneys perfused with V52 at $-3°$ C. using the optimal techniques of the time survived 75% of the time, but when these kidneys were cooled to $-30°$ C., the survival rate upon warming and washout was 0%. Thus, cooling caused injury at 49% w/v cryoprotectant and caused complete loss of viability at 52% w/v cryoprotectant. Since, ideally, organs should be preserved in V55 (to avoid the need for high pressures), this trend was unfavorable. However, a positive implication was that cooling injury might become negligible at concentrations lower than 49%, so that cooling to temperatures near $-30°$ C. might then be innocuous. This suggested the possibility of cooling at a relatively low concentration so as to avoid cooling injury and then raising the concentration to a vitrifiable level at the lower temperature. This approach would have the additional advantage of exposing the organ to vitrification solution at a temperature at which its toxicity should be reduced. Thus, by avoiding cooling injury, toxicity might also be avoided.

A secondary point was that a variety of experiments on the phenomenon of thermal shock in both erythrocytes and kidney slices suggested that cooling injury below $-30°$ C. might be minimal even in the presence of V55 if cooling injury above $-30°$ C. were first prevented. Therefore, by first cooling to near $-30°$ C. in the presence of a concentration that does not cause cooling injury, it was inferred that even V55 might not cause fatal cooling injury when the organ was loaded with V55 at the low-temperature perfusion temperature and was subsequently cooled to below $-30°$ C.

As noted in the preceding section, the first hypothesis was verified in that the two-step approach successfully avoided cooling injury and the toxicity of V55 at $-25°$ C. As noted in the results section, the second hypothesis was also verified in that fatal injury did not occur upon further cooling to below $-46°$ C. was also avoided.

4. Cryopreservation of the Organ

The next step of any practical cryopreservation procedure, such as vitrification, is to cool the organ to cryogenic temperatures using appropriate protocols, with or without prior pressurization. The cryopreservation step also includes the storage of the organ. The present invention is not concerned with the actual cryopreservation and storage of the organ, but only with the preparation of the organ for cryopreservation and the preparation of the previously-cryopreserved organ for transplantation.

5. Perfusion of the Organ in Preparation for its Transplantation

In preparation for transplanting it, the organ is first warmed up from the storage temperature to an appropriate temperature for reperfusion of the organ. The warming of the organ after its cryopreservation is presently not performed in the apparatus of this invention. The organ may then be placed back into the perfusion apparatus of this invention to resume the type of perfusion protocol shown in FIGS. 5 and 6 at the beginning of phase 5 (the first cryoprotectant washout plateau).

a) Temperature during phase 5: In the best mode method, the organ was warmed to approximately $-3.0°$ C. and placed into the perfusion apparatus to begin cryoprotectant washout at this temperature. The inventors unexpectedly found that this approach was superior when the two-step best mode method for introducing cryoprotectant was used and was successful even when the final vitrification solution used was V55. Given that the introduction of vitrifiable concentrations was possible at temperatures near −25° C., the inventors had expected that it would be advantageous as well to remove part of the cryoprotectant at this temperature in order to avoid the expected high toxicity of fully vitrifiable concentrations at temperatures near −3° C. Instead, the dilution of vitrification solution at the low temperature perfusion temperature was found to be detrimental. Within the method limits, the temperature during phase 5 can range from −20° C. to +5° C.

b) Cryoprotectant concentration and duration of phase 5: The concentration of cryoprotectant during phase 5 in the best mode protocol for the kidney and liver was 30% w/v (300 grams/liter; 4.6M) to 33% w/v V49 solutes (D, F, and P in the usual proportions), acceptable variations being 20–40% (w/v or w/w) cryoprotectant (roughly 3 to 6.0M). The concentration at this stage should not be less than 40% (⅔) of the concentration of the vitrification solution in order to avoid osmotic damage; in the best mode, the concentration at phase 5 was ⅗ of the highest concentration perfused.

The criterion for terminating phase 5 and moving on to phase 6 was somewhat different from that previously employed. It was found that prolonged periods at phase 5 sometimes led to changes suggestive of cellular uptake of the LMW OBA that was generally present during this plateau and that should remain extracellular for maintaining the viability of the organ. It was consequently determined that the duration of phase 5 should be limited to what is required to allow the A-V concentration difference to begin to return to zero (in the inventors' experience, to return from an off-scale value to a value near −50 mM), rather than prolonged to the point that the A-V concentration difference is no longer rapidly changing. Note the shorter phase 5 time in FIG. 6 as compared to that in FIG. 5, reflecting the optimization required for success at the higher concentrations used in the protocol reflected in FIG. 6. Note also the abrupt end to the recovery of the A-V concentration gradient in FIG. 6 as contrasted with the prolonged equilibration of A-V concentration during phase 5 in FIG. 5. For the rabbit kidney, the optimal time was determined to be 9 min. Within the method limits, durations of 0–30 min are acceptable.

c) OBAs and their use during phase 5: One or more OBAs (defined as above) were generally present during phase 5.

As previously defined, one way to categorize OBAs, for ease of discussion, is as LMW ($M_r$ between 100 and 1000 daltons) OBAs and HMW ($M_r$ between 1000 and 500,000 daltons) OBAs. However, there is in fact no sharp dividing line between LMW and HMW OBAs, and different $M_r$-ranges have uniquely different properties, and hence different practical applications. Some of these key properties, which give rise to the broader principles behind the usages described below, can be summarized as follows:

| $M_r$ Range | Membrane Permeability | Osmotic Effect | Oncotic Effect | Viscosity | Cost |
|---|---|---|---|---|---|
| 180–342 | Highest | Highest | Nil | Lowest | Lowest |
| 343–1,000 | Low to Mod. | High–Mod. | Nil | Mod. | Mod.–High |
| 1,000–50,000 | Low to Nil | Low | Nil–Low | Mod.–High | Mod. |
| >50,0000 | Nil | Lowest | Low–High | Highest | Mod. |

The inventors have unexpectedly discovered several new modes of OBA usage. For application at phases 5 and 6, these new modes consist of i) combined LMW and HMW OBAs (for use with the highest-concentration protocols), ii) single midrange OBAs (for high and moderate-concentration protocols), iii) very LMW OBAs (for lower-concentration protocols), and iv) specific OBA protocols for the liver. In this section, these usages and the principles on which they depend are discussed generally without reference to phase 6.

i) Combined LMW and HMW OBAs. For the kidney and most other organs, the best mode OBA usage was considered to be sucrose, for example about 300–350 mM, or other LMW OBA in combination with hydroxyethyl starch (HES: relative molecular mass ($M_r$) of 20–500 kd (20,000–500,000 daltons)), for example 3–8% w/v, or other equivalent HMW OBA. Two specific experimental examples illustrated below which yielded good results after perfusion with the normobaric vitrification solution V55 involved the use of 350 mM sucrose in combination with 3% w/v HES of $M_r$ 450 kd. Other preferred LMW OBAs include maltose, raffinose, potassium and sodium fructose 1,6-diphosphate, potassium and sodium lactobionate, potassium and sodium glycerophosphate, potassium and sodium gluconate, maltotriose, maltopentose, stachyose and mannitol. The preferred HMW OBA, HES, is sold by McGaw Corp. of Irvine, Calif. as a 200 or 450 kd chain, but is easily hydrolyzed to lower molecular weight forms. Particularly preferred are HES molecular weights in the 1 to 100 kd range. Other preferred HMW OBAs include polyvinylpyrrolidone (PVP), potassium raffinose undecaacetate (available from Sigma Chemical Co., St. Louis, Ill.) and Ficoll (1 to 100 kd).

The presence of a LMW OBA is required to counteract the otherwise fatal osmotic effects of a large stepwise drop in penetrating cryoprotectant concentration. In protocol variations employing larger drops in cryoprotectant concentration (e.g., lesser phase 5 concentrations near 20% w/v cryoprotectant), more LMW OBA is required (to an upper limit of 750 mM). In variations employing higher phase 5 concentrations (e.g., 40% w/v cryoprotectant), less LMW OBA is required (to a lower limit of about 150 mM).

This best mode use of OBAs during the first cryoprotectant washout plateau (phase 5) applies particularly to protocols employing more than 7.5M V49 solutes, i.e., to protocols employing less than 500–1,000 atmospheres (atm) of hydrostatic pressure for vitrification. Exclusive use of the LMW OBAs mannitol and sucrose were found by the inventors to be compatible with at best only a 30% kidney survival rate (2 survivors of 7 so treated) when V52 was used in place of V49, vs. a 100% survival rate (14/14) when V49 was used. However, adding 3% w/v 450 kd HES during washout of the cryoprotectant raised survival to 75% when either mannitol or sucrose was used as the LMW OBA (6 survivors out of 8 kidneys treated) when the onestep vitrification solution addition method was used.

The concept of using HMW agents as OBs had not previously been contemplated, at least in part, because such agents have little osmotic effect in comparison to lower molecular weight compounds. While not wishing to be bound by any specific theory, the following considerations led the inventors to use HES as a prototypical HMW OBA.

(a) In the presence of high concentrations of cryoprotectant, the concentration of HMW material was higher with respect to water than in the case of traditional, dilute aqueous solutions. Therefore, the osmotic effect of the agent was enhanced.

(b) The oncotic function of a HMW agent could be crucial in protecting the vascular system from abrupt collapse upon sudden dilution of the cryoprotectant or could otherwise benefit the vascular system.

(c) The HMW agent may reduce abnormal cellular uptake of LMW OBAs by lowering interstitial volume (thus lowering the pool size of LMW OBA available to penetrate cells) or by acting as a physical barrier to diffusion of LMW OBA to and/or through the cell membrane.

(d) The HMW OBA, by its oncotic action to dilate or prevent the collapse of the vascular compartment, should facilitate cryoprotectant washout and thus reduce osmotic stress caused by lags in cryoprotectant washout.

(e) Any abnormal increase in membrane permeability that may cause LMW OBAs to partly penetrate organ cells will not cause HMW OBAs to penetrate, thus the use of HMW OBAs will reduce the net amount of abnormal penetration per miliosmole of OBA that is used.

The best mode use of HMW OBAs was to use agents that have at least the osmotic or oncotic pressure of 3–6% 450 kd HES. However, lower $M_r$ agents than this may be better since a relative molecular mass of 50 to 200 kd should create equal or greater oncotic pressure and still guarantee failure of the agent to penetrate a viable cell.

The combination of HMW and LMW OBAs was preferred because the former offset the uptake of the latter and added to the latter's osmotic effectiveness, while LMW agents provided sufficient osmotic pressure to accomplish the primary job of preventing cellular water uptake during cryoprotectant dilution. In addition, the high viscosity of HMW OBAs in cryoprotectant solutions supported the use of the less viscous LMW agents as the primary osinolytes to which HMW agents were added as adjuncts.

ii) Midrange OBAs. For the kidney and most other organs, another preferred OBA usage method is the exclusive use of single OBAs in the molecular weight range of 360–10,000 daltons, used at total concentrations of 2%–15% w/v. Examples of suitable OBAs in this application include maltose, raffinose, potassium and sodium fructose 1,6-diphosphate, potassium and sodium lactobionate, maltotriose, maltopentose, stachyose, potassium raffinose undecaacetate, Ficoll and HES within the specified molecular weight range.

While not wishing to be bound by any theory, single agents in this weight range often adequately combine the properties of LMW and HMW OBAs into a single agent. Osmolyte impermeability is the most important feature of an OBA and this impermeability may approach a practically-relevant maximum at molecular weights between 360–10,000 daltons or, more narrowly, of around 360–2,000 daltons. Solutes in this weight range are relatively osmotically effective while being also relatively low in viscosity and relatively high in solubility. This middle molecular weight range is therefore presumptively the ideal one when neither oncotic effectiveness nor cost is critical. Some agents in this weight range will also be impermeable to both kidneys and livers, thus eliminating at least part of the distinction between these organs.

(iii) Very LMW OBAs as the sole OBAs for "low" concentration methods. When the vitrification method was to involve the use of relatively low concentrations of cryoprotectant, e.g., V49, the use of mannitol ($M_r$=180 daltons) as the sole OBA has yielded satisfactory results (see results section for pertinent data), and the low viscosities of mannitol solutions maintained better organ flow than more viscous (higher $M_r$) solutions. Consequently, another embodiment of the best mode was the use of very LMW OBAs (OBAs with $M_r \leq 400$ daltons) as the sole OBAs when vitrification methods are used that employ elevated pressures and/or concentrations less than that of V52.

While not wishing to be bound by any theory, lower cryoprotectant concentrations were less stressful and maintained membrane permeability more effectively, and for this reason allowed lower $M_r$ agents to be effective. Because mannitol was extremely inexpensive and universally non-toxic and because the cost of OBAs tends to rise sharply with $M_r$ in the range from 180–2,000 or more daltons, mannitol and/or similar LMW OBAs (e.g., sucrose, maltose) will be the agents of choice in these "low" concentration embodiments of the method.

(iv) OBA usage for the liver. For the liver, the best mode OBA usage was the complete omission of OBAs. Two other preferred uses of OBAs are the use of HMW OBA alone (for example, 3–5% HES, $M_r$ 10,000–450,000 daltons, or its equivalents as noted above) and the use of midrange OBAs ($M_r$ about 350 to 10,000), particularly when the cryoprotectant washout rate is high.

(a) Complete Omission of OBAs. Experiments with 4 control livers perfused with neither cryoprotectant nor the normal HES of modified UW solution indicated that life support function could be obtained in three cases. When the experiment was repeated with the inclusion of V49 perfusion, and no LMW osmolyte was used, not only did about 50% of the livers support life after transplantation, but they did so after almost complete equilibration with V49, in contrast to livers perfused with V49 in the presence of HES, which equilibrated poorly and had a survival rate no better than the livers perfused without HES. Therefore, neither LMW nor HMW osmolytes were mandatory for livers.

While not wishing to be bound by any theory, the acceptability and the desirability of omission of all OBAs for the liver were thought to be based on the liver's high permeability to both cryoprotectants and nominal LMW OBAs. The liver is unique in that its parenchymal cells are exceptionally permeable to LMW solutes, including cryoprotectants. This allows faster rates of cryoprotectant addition and washout with less osmotic stress than occurs in other organs. For example, liver slices were found to withstand abrupt multimolar changes in cryoprotectant concentration that would have been lethal to most other types of tissue, including the kidney, and using smaller changes in concentration did not produce improved survival in liver cells after cryoprotectant exposure and washout. With respect to the intact liver, note in FIG. 10 the reasonably steady flow rates (suggesting no excessive osmotic cell swelling) during washout of V49 from the liver despite the absence of both LMW OBAs and HMW OBAs. Finally, since liver cells are somewhat permeable to sucrose, sucrose will be relatively ineffective as an OB during cryoprotectant washout, but its leakage into the cells might actually cause cell swelling upon transplantation.

(v) Exclusive Use of HMW OBA. The above-described experiments revealed one difficulty with the omission of HES, and that is the fact that only 3 out of 4 control livers (no cryoprotectant) survived perfusion in the absence of HES, vs. higher survival when HES was used. HES or its equivalent may therefore have to be present to adequately support hepatic viability regardless of the presence or absence of cryoprotectant. Because HES cannot be present (except at minimal concentrations) during the loading of vitrifiable cryoprotectant concentrations due in part to its unfavorable effect on viscosity, one way to maximize HES for maintaining viability would be to add HES only when the cryoprotectant is being washed out, simply because perfusion with HES will be more feasible from a physical standpoint (lower viscosity) when the cryoprotectant concentrations are low compared to the vitrifiable concentrations, and when these concentrations are falling rather than rising. In this context, HES would not necessarily be acting as a true OBA but only as an ordinary osmotic support agent. Nevertheless, the HES would be used in essentially the same manner procedurally as it would be used if it were being used as an OBA, so from a practical point of view this would be the equivalent of using a HMW OBA as the sole OBA. Furthermore, it must be remembered that the liver consists of more than merely hepatocytes, and an osmolyte such as HES could act as a true OBA for these non-hepatocytes. The decision to use HES or other equivalent HMW OBA during elution of cryoprotectant from the liver can be made depending on the ability of the type of liver in question to withstand the absence of HES during control perfusions and to withstand the absence of HES during cryoprotectant elution.

Although the liver did not equilibrate well with cryoprotectant when perfused with a combination of cryoprotectant and HES in the above-described experiment, this problem can be overcome by using an osmolyte with a sufficiently low $M_r$ to control viscosity adequately, e.g., HMW OBAs equivalent to HES of $M_r$=2–50 kd.

(c) Midrange OBAs for rapid cryoprotectant efflux from the liver. OBAs ranging in $M_r$ from 350 to 10,000 daltons, being less permeable than sucrose, yet considerably less viscous than most HMW OBAs (hence, perfusable at a sufficiently rapid rate), may protect liver cells other than hepatocytes from osmotic injury, especially during very rapid rates of change of cryoprotectant concentration. Therefore, either one such agent or a combination of two or more such agents falls within the method limits for the liver.

d) Phase 6: Gradual reduction of cryoprotectant concentration to zero with simultaneous elevation of perfusion temperature: In the best mode method for the kidney, the gradual reduction of cryoprotectant concentration to zero or virtually zero was carried out at a constant rate of about −42 mM/min (acceptable variations being −31 to −75 mM/min for the kidney and most other organs, or −31 to −150 mM/min for the liver). Non-constant declining concentration schedules (rapid fall at high concentrations, slower fall at lower concentrations) are also an acceptable variation, e.g., a linear fall at 1.5 times the average linear rate for the first third of the washout followed by a linear fall at 0.86 times the average linear rate for the second two-thirds of the washout.

During cryoprotectant washout, the temperature was elevated to facilitate washout, reduce osmotic forces, and restore a perfusion temperature appropriate for an organ containing no cryoprotectant. In the best mode method for the kidney, temperature elevation began as the concentration fell to 4.7M and continued linearly with concentration drop until the initial perfusion temperature was reached and arterial concentration reached 1.3 to 0.8M (1° C. rise per 0.68 to 0.78M decrease in concentration; total of 3.4–3.9 M concentration change during warming) as illustrated in FIGS. 5 and 6. Acceptable variations for the concentration at which the temperature initially rises are 2.5–5.5M and for the concentration at which temperature rise is completed are 0.5M–4.5M.

e) OB washout during phase 6: The general method for OB washout during phase 6 was to incompletely wash out the LMW OBA while maintaining HMW OBA concentration (when HMW OBA was present) constant or reducing HMW OBA concentration by only 1–2% w/v. More particularly, as penetrating cryoprotective agent concentrations fell, the concentration of LMW OBA also fell in proportion reaching a final nonzero concentration of OB when penetrating cryoprotectant concentration reached zero. This final nonzero concentration of LMW ORA was 50 mM in the best mode method and may acceptably vary from 25 mM to 500 mM. In an embodiment of the invention, the final non-zero concentration of LMW OBA was from 150 to 1000 mM. As an example, in the best mode (FIG. 6), in which 350 mM sucrose was brought to 50 mM sucrose while 5.0M cryoprotectant was reduced to 0.0M cryoprotectant at a rate of 42 mM/min, sucrose concentration dropped at the rate of 2.5 mM/min.

While not wishing to be bound by any theory, during reduction of cryoprotectant concentration, absolute trans membrane osmotic forces attributable to the cryoprotectant trans membrane concentration gradient became reduced, thus reducing the requirement for osmotic buffering. Reducing OB concentration during cryoprotectant washout was therefore designed to minimize osmotic damage from the OB both during cryoprotectant washout and thereafter and was further designed to reduce potential cellular uptake of nominally non-penetrating OBA. No previous perfusion technique of cryoprotectant washout has ever made use of this "declining OB principle." When LMW and HMW OBAs were used together, a differential decrease in OB was performed wherein the concentration of the LMW agents declined while that of the HMW OBAs remained the same or nearly the same.

f) OB washout phase 7:

i) Standard mode. The final step in the method after removing all cryoprotectant is to continue to perfuse the organ to allow it to fully equilibrate with the cryoprotectant-free medium and, if desired, to continue or complete the washout of the OB. In the current best mode for the kidney, 50 mM sucrose and 3% w/v HES $M_r$ 450 kd was attained at the end of cryoprotectant washout, and no additional washout of these OBAs was undertaken prior to transplantation. Although it is acceptable to leave such low concentrations of OB in the organ during short holding times before transplantation, interstitial OB is expected to cause osmotic expansion of the interstitial space during blood reflow with a consequent temporary reduction in organ perfusion in vivo. This effect will become unacceptable at higher OB concentrations ($\geq$100–500 mM, or $\geq$3–7% w/v) and will necessitate at least partial OB washout before transplantation. A further problem with leaving OB in the organ for extended times before transplantation is the potential leakage of OB into organ cells with consequent cellular swelling and reduced perfusion upon transplantation. In experiments with V49, the inventors typically washed out 50 mM mannitol over the course of 30 min with complete success upon transplantation. However, it was generally observed that leaving 50 mM LMW OB in the kidney for short times before transplantation was beneficial at higher cryoprotectant concentrations, in some cases representing the difference between organ survival or death. It has never been observed that leaving 50 mM mannitol or sucrose in the kidney prior to transplantation was more detrimental than entirely removing this final concentration, so the washout of OBA during phase 7 is primarily concerned with reducing LMW OBA concentrations down to less than about 100–500 mM and with reducing HMW OBA concentrations down to less than about 5–8% w/v.

While not wishing to be bound by any theory, the retention of 50 mM LMW OBA is believed to be beneficial because interstitial osmolyte will reduce cell and organelle swelling until the moment metabolism is restored in vivo, and that metabolizing cells are capable of osmoregulation to cope with intracellular leaked mannitol or sucrose provided the extracellular osmolyte can slow down passive cellular swelling long enough for osmoregulation to be restored. In addition, the use of higher $M_r$ OBAs will preclude cellular uptake of OBAs, further increasing the acceptability of leaving in the OBA.

Higher concentrations of OB (up to 500 mM) may be washed out over more extended times (30–90 min) that depend oil the perfusion resistance response to OB dilution. For clinical purposes, the duration of the post-washout perfusion period, comprising the OB washout, and the degree of OBA washout must be adjusted to be compatible with the exposure times imposed by the logistic requirements of organ transportation and transplantation.

ii) The three-osmolyte washout technique. In the inventors' early experience involving perfusion of 8.4M cryoprotectant at about −3° C. (one-step addition technique), consistent control of vascular resistance during cryoprotectant washout and excellent appearance of the kidneys 40 minutes after transplantation were obtained when the following procedure was used, and only when it was used.

After perfusion with 8.4M cryoprotectant, the concentration of the cryoprotectant was dropped to about 5.0M with the simultaneous introduction of 250 mM sucrose and 4% w/v HES. After a 9 minute phase 5 plateau, the standard linear sucrose washout technique was followed while holding HES concentration constant at 4% w/v. However, once all cryoprotectant was removed, the HES concentration was gradually reduced to 3% w/v while the sucrose concentration was gradually reduced to zero and mannitol was concomitantly introduced to a final concentration of 50 mM.

Thus, the innovations involved in the three-osmolyte washout technique were: 1) to combine a HMW with two LMW OBs resulting in a 3-OBA method, and (2) to replace one OB (sucrose) with another OB (mannitol) just prior to transplantation.

While not wishing to be bound by any theory, this approach was developed for the following reasons. Sucrose is more effective osmotically than mannitol, i.e., it is less likely to leak into renal cells due to its higher molecular weight. However, unlike mannitol, it does not have any ability to quench free radical reactions during reperfusion of the organ with blood upon transplantation. By using sucrose to carry out the primary osmotic buffering function and mannitol to maintain osmotic buffering at the end of the perfusion, the advantages of both agents were obtained and the disadvantages of both agents were avoided. Second, 4% HES appeared optimal for balancing the tradeoff between minimizing viscosity while maximizing osmotic and oncotic effectiveness during phases 5 and 6. Finally, 4% HES was reduced to 3% just before transplantation to minimize perfusate viscosity and the quantity of interstitial HMW species.

It is not to be construed that this method depends specifically on sucrose, HES or mannitol. The governing principle involved is a general one.

6. Treatment of the Organ and the Recipient at the Time of Transplantation and Thereafter It is important that the recipient receive aspirin (acetylsalicylate, 1–3 mg/kg) and heparin (100–250 units/kg) shortly before release of the vascular clamps and reperfusion of the transplanted organ, both higher and lower concentrations of both drugs resulting in vascular obstruction and failure. The best mode concentrations were 2 mg/kg and 200 units/kg, respectively. It may also be helpful to gradually infuse agents that reverse sulfllydryl oxidation (e.g., aurothioglucose or N-acetylcysteine at serum levels of 0.1–10 mM), inhibit extracellular (e.g., α-2 macroglobulin, amiloride, tissue inhibitor of metalloproteinases (TIMP)) and intracellular (leupeptin, glycine) proteases or facilitate endothelial cell adhesion (TGFβ1, 0.1–10 μg i.v. per every 5 min for 40–300 min). The inventors have found that dimethyl sulfoxide reduces the ability of renal tissue to restore depleted tissue SH content and have found massive elevation of urinary urokinase after the transplantation of rabbit kidneys.

III. Method for the Perfusion of an Organ With Non-Cryoprotectant Perfusates

In addition to the organ cryoprotection perfusion protocols, the apparatus and methods described herein are capable of use in a wide variety of protocols for conventional organ hypothermic and normothermic preservation. In addition, a wide variety of normothermic pharmacological, physiological, and pathophiysiological protocols are possible using the apparatus and methods of this invention. The inventors indicated many of these possibilities earlier and in describing the steps required to carry out many of these protocols in FIGS. 11A and 11B, which are self-explanatory.

IV. Results

A. Endothelial cell protection with TGFβ1

TGFβ1 allowed endothelial cells to remain properly attached to fibronectin medium or substrate in a culture flask when washed with cryoprotectant solution Table 4. TGFβ1 is expected to have a similar effect on endothelial cells in vivo.

TABLE 4

Protection Against Endothelial Cell Detachment by TGFβ1*

| Treatment | # of Non-Detached Cells | p Value vs. Controls |
|---|---|---|
| 37° C. Controls | 5.05 ± 0.31 × 10$^6$ | — |
| 2° C. Controls | 4.33 ± 0.38 × 10$^6$ | n.s. |
| V52 (superfused according to whole kidney protocol: V52 itself = 20 min exposure) | 1.38 ± 0.10 × 10$^6$ | <.00002 |
| V52 + TGFβ1 (same as V52 above but culture pretreated with TGFβ1 at 10 ng/ml for 22 hours) | 4.95 ± 0.21 × 10$^6$ | n.s |

*Detachment was determined by trypsinizing the flasks after each experiment, washing out the cultured endothelial cells and counting them. Detached cells removed during the superfusion are not seen in this assay, causing the cell count to go down.

B. Rabbit Kidneys.

1. Suitability of V49B-type Solutions.

Viability data from rabbit kidney slices after treatment with V49 or V49B are shown in Table 5.

TABLE 5

Viability or Rabbit Kidney Slices Treated With V49 or V49B

| Treatment | K/Na ratio of tissue* (mean +/− SEM) |
|---|---|
| V49 | 3.43 +/− 0.07† |
| V49B | 3.27 +/− 0.12† |

†p > 0.05
*The K/Na ratio was measured after washing out the cryoprotectants and incubating the cortical slices at 25° C. for 90 minutes to permit active transport of K$^+$ and Na$^+$.

2. Suitability of V49 and V52 for the Intact Kidney.

FIG. 12 shows post-operative serum creatinine levels of rabbits which had received transplanted kidneys that had been previously perfused with V49 in Euro-Collins solution. Prior to procurement, the kidneys were treated in vivo with zero, 15, or 25μg/kg of iloprost administered by systemic intravenous infusion over a 20 minute period. Kidneys in these three groups were exposed to V49 (7.5M) at +2°, 0–2° and −1° to −6° C., respectively. Initial and final perfusion temperatures were 2° C. in all cases. Rabbit survivals in these three groups were 5/16 (31%), 6/10 (60%), and 10/10 (100%), respectively. Only data for rabbits surviving the first night after surgery are included. Rabbit survivals depended entirely on the function of the transplanted kidney because a contralateral nephrectomy was performed at the time of transplantation, and no support by dialysis was attempted. Histology in these rabbits was poor at long-term follow-up without iloprost treatment, marginal with the lower dose of iloprost, and normal with the higher dose of iloprost and the lowest perfusion temperatures. The results of control (no cryoprotectant) perfusions with Euro Collins are included in FIG. 8 as well (bottom curve). Although damage in the best V49 group is greater than in the controls, all damage appeared to be fully reversible within a short time postoperatively.

Table 6 shows that when an attempt was made to extend the success at 7.5M cryoprotectant to 8M cryoprotectant, the result was nearly uniform failure unless 3% HES was incorporated into the solutions used to wash out the 8M concentration. The use of HES allowed the survival of 75% of rabbit kidneys after transplantation. Leaving the LMW OBA in the rabbit kidney was also beneficial to the kidneys after their transplantation (Table 6).

TABLE 6

Recovery of Whole Rabbit Kidneys Perfused with 8 M Cryoprotectant

| Treatment | % Life Support Function |
|---|---|
| A. Standard Protocol with Either Mannitol or Sucrose Washout | 0 |
| B. Modified Protocol with 1st Plateau Raised to 30% and 3rd Plateau Raised to 33% w/v to Reduce Osmotic Stress | 8 |
| C. Same as B, but Lowered Perfusion Temperature from −1.5° C. to −3° C. | 29 |
| D. Same as C, but Used 3% HES During Washout of Cryoprotectant and left 50 mM Mannitol in the Kidney Until Transplantation | 75 |
| E. Same as D, but Used Sucrose vs. Mannitol | 75 |
| F. Same as D, but Removed All Mannitol Before Transplantation | 0 |
| G. Same as E, but Removed All Sucrose Before Transplantation | 33 |

C. Overcoming Cooling Injury at −46° C. and Toxicity at 8.4M Cryoprotectant

When kidneys were treated with either 7.5M or 8M cryoprotectant using 3% HES during washout as in Table 6, they were still unable to withstand cooling to −30° C. (FIG. 13). The 100% survival rate at 49% cryoprotectant fell to just over 50% as a result of cooling, and the 75% survival rate of the 8M group fell to 0%.

Although some of this injury was due to the greater time required to allow cooling and warming to take place, tissue slice evidence indicated that cooling per se was actively detrimental. As seen in FIG. 14, exposure of slices to 8M cryoprotective agent at 0° C. was considerably more damaging than exposing them to 6.1M cryoprotectant at the same temperature (cf. bars 2 and 4), and cooling these 8M slices to −23° C. caused additional injury (cf. bars 2 and 3). Interestingly, however, cooling 6.1M slices to −23° C. did not cause additional injury (cf. bars 4 and 5). Even more interestingly, when slices loaded with 6.1M cryoprotectant were transferred to a 31 23° C. solution of 8M, or even 8.4M cryoprotectant, there was still no damage associated with cooling, nor was there damage associated with cooling, nor was there damage associated with exposure to these higher concentrations (cf. bars 4 and 5 to bars 6 and 7). In fact, slices exposed to 8.4M at −23° C. according to the two-step approach (first cool, then expose to higher concentrations, bar 7) had more viability than slices simply exposed to the lowest concentration of 8M at 0° C. without cooling (bar 2, p=0.033). These results showed that, at least in slices, both cooling injury and cryoprotectant toxicity were preventable by cooling first in a low concentration and introducing higher concentrations only in a second step at the lower temperature, in this case −23° C.

Re-examination of FIG. 13 suggested that the same phenomenon applied to the intact kidney. Recovery was higher at the lower concentration of cryoprotectant, and if one drew a line connecting the 8M cooled point and the 7.5M cooled point, it extrapolated to 100% survival at some concentration below 7.5M. Because the linearity of such an extrapolation was not known, the inventors elected to try an experiment with a concentration comfortably below 7.5M, i.e., with 6.1M as in the slice experiment.

The results of this experiment are indicated in FIG. 15. 100% of the kidneys loaded with 6.1M cryoprotectant, cooled to around −22° C., and warmed up (protocol indicated in the insert) supported life, giving excellent mean serum creatinine levels after 14 days ($Cr_{14}$) and acceptable peak creatinine values (pCr). FIG. 16 shows the results of loading 6.1M cryoprotectant at −3° C., cooling to −23° C., and then perfusing the kidney with 8M cryoprotectant until equilibrium was achieved. As in the previous experiments, the 8M cryoprotectant was washed out using 3% HES. In stark contrast to the results of the one-step cryoprotectant addition method followed by cooling to −30° C. (FIG. 13), the 8M kidneys of FIG. 16 had an excellent survival rate of 7/8, and the kidneys that did survive were not different from the 6.1M kidneys in terms of their $Cr_{14}$ and pCr values, in full agreement with the slice results of FIG. 14. Furthermore, as shown in FIG. 17, when kidneys were perfused with 8M cryoprotectant at −22° C., they could then be cooled another 10° C. to −32° C. (colder than in FIG. 13), with 100% survival upon warming and with $Cr_{14}$ values identical to those of slices exposed only to 6.1M cryoprotectant, again in complete agreement with the predictions of FIG. 14.

FIG. 18B shows that the injury associated with cooling increases between −30 and −60° C. but does not increase with further cooling to near the glass transition temperature. FIG. 18A shows an attempt to more precisely determine where between −30° and −60° C., cooling injury stops increasing. Although the magnitude of the drop was somewhat small in this experiment, it appeared that slices cooled to −45° to −50° C. experienced a maximum amount of cooling injury.

Using the information of FIG. 18 as a guideline two additional experiments were done with intact kidneys. After spending approximately 9 months optimizing the procedure for introducing and removing V55, the following optimum method was identified. The first step of the two-step approach was to perfuse 44% w/v cryoprotectant (6.73M) at −3° C. and then cool to −25° C. for perfusion with V55 (55% cryoprotectant, 8.4M). The kidneys were then warmed back to −3° C. and were washed out with 3% w/v HES and 350 mM sucrose as described above. This protocol resulted in a survival thus far of 2 out of 3 kidneys so treated. These kidneys looked excellent after 40 min of blood reflow in vivo and, as shown in FIG. 19, they were able to return serum creatinine levels to near or below 2 mg/dl, an excellent result. Furthermore, one kidney perfused with V55 at −25° C. by this procedure was cooled to −46° C. prior to warming and washed by the same procedure used in the non-cooled V55 kidneys. The result for this kidney, also shown in FIG. 19 (dashed line), was similar: the kidney looked excellent upon transplantation and, at the time of submission of the patent application, was restoring serum creatinine to a value near 2 mg/dl. The kidney showed a peculiarly delayed recovery, maintaining creatinine at values near 15 for an unprecedented amount of time, but the peak creatinine and the rate of return of serum creatinine back to baseline after this long delay were not different than what was observed for the other two V55 kidneys.

Taken together, the slice results of FIG. 18 and the intact kidney data of FIG. 19 indicated that rabbit kidneys can now be cooled to the glass transition temperature without losing viability. Furthermore, since FIG. 19 employed a concentration of cryoprotectant that vitrifies without applied pressure, the implication is that high pressures are no longer mandatory for organ vitrification.

D. Pertinence of Animal Data to Human Kidney Cryopreservation

1. First Human Kidney

A 232 gram human kidney was perfused according to the method of this invention and was then vitrified. Digital data from the method was captured using a BASIC program and was edited and plotted using a sigmaPlot 5.0 graphics package (Jandel Scientific, San Rafael, Calif.) to generate the data in FIGS. 20A, 20B and 21.

The data in FIG. 20A show that the method of the invention produced the expected results in this human kidney. Although the measured molarity was slightly greater than the target molarity and the first step change in concentration slightly overshot the target, the data follow the protocol reasonably well.

The data in FIG. 20B from the same human kidney show that resistance (expressed as mm Hg divided by flow) and flow (ml/min/gm of kidney) behaved in a way that was qualitatively similar to their behavior in rabbit kidneys.

The data from the subsequent vitrification of this human kidney demonstrated that this method performed adequately. The data in FIG. 21 provide no indication of freezing of the kidney which would have been represented by a temperature plateau followed by a relatively rapid fall in temperature. After an initial thermal lag above 0° C. which represented the time for the external temperature front to penetrate through the mass of the kidney to the temperature probe in the middle, the temperature dropped rather smoothly, revealing virtually no evidence for ice formation.

2. Second Human Kidney

This human kidney was a pediatric kidney from a four month old donor. This kidney was stored for about 79 hours after it was collected but before it was perfused with V55 cryoprotectant according to the method of this invention. The data in FIG. 22 show the perfusion of this kidney with V55 (ascending portion of the curve), and the removal of V55 cryoprotectant from the kidney (descending portion of the curve). The dotted and solid lines in FIG. 22 show the achieved and target V55 concentrations, respectively. The perfusion pressure was set at 35 mmnhg in this experiment.

The discrepancy between the measured and target concentrations was merely a matter of calibration rather than a true limitation of the method. The pressure spikes which occurred when a concentration of 8.4M was quickly approached or retreated from reflected software that was not specifically designed to prevent these spikes and has since been corrected. This was not a limitation of the method. Since this kidney was unloaded, a cooling curve was not generated. Resistance, flow and temperature are not shown in FIG. 22.

E. Kidney Slice Viability Data

Viability data from rabbit (FIG. 23A) and human (FIG. 23B) kidney slices and normalized data for rabbit (R) and human (H) kidney slices (FIG. 23C) show nearly identical responses of the human and rabbit kidney slices to V49. Although the data showed a slightly lower recovery of human kidney tissue compared to rabbit tissue after cooling to −30° C., this recovery was within the variability seen with rabbit kidney slices. The human kidney was several days old before the experiment was carried out, whereas the rabbit kidneys were "fresh". The absolute human K/Na ratio was depressed about as much as would be expected for rabbit slices stored for a similar time.

These data in combination with the perfusion data in this section showed that human kidneys can be loaded with cryoprotectant according to the method of this invention and can be essentially vitrified on cooling—e.g., be cooled below the glass transition temperature with minimal or no ice formation in the organ. These data also showed that the cryoprotectant can be removed from the human kidneys using the method of this invention. Lastly, the similarity of the viability data of the rabbit and human kidney slices combined with the fact that rabbit kidneys actually survived and maintained the lives of rabbits into which they had been transplanted, suggest similar results will be obtained when human kidneys are treated using the methods of this invention.

F. Applicability to Other Organs: The Rat Liver Model

Rat livers were perfused using the protocol as shown in FIG. 10. The perfusion fluid did not contain either HES or LMW OBs. The data in Table 7 show total bile production at 5, 10 and 15 minutes after transplantation and survival at 7 days after liver transplantation into host rats. These data demonstrated that rat livers perfused with the solutions supported the lives of host rats into which they had been transplanted after their perfusion.

TABLE 7

Functional Recovery and Life Support Function of Rat Livers Perfused with Vehicle or V49

| Experiment | Liver Weight (% change) | Total Bile Production at 5, 10 and 15 min (μl/g ± SD) after Transplantation | | | Rat Survival 7 days after Transplantation |
|---|---|---|---|---|---|
| Control Pfn* w/UW1† (HES) | −9.9 ±2.1 | 1.68 ±.94 | 5.19 ±2.33 | 9.32 ±3.65 | 6/6 (100%) |
| Control Pfn* w/UW2‡ (no HES) | −8.7 ±0.5 | 2.03 ±.75 | 4.62 ±1.50 | 7.67 ±2.48 | 5/6 (83%) |
| V49 Perfusion w/UW1† HES) | −8.7 ±0.7 | 0.66 ±.50 | 1.62 ±0.82 | 3.14 ±1.38 | 2/4 (50%) |
| V49 Perfusion w/UW2‡ (no HES) | −6.3 ±3.0 | 1.20 ±.98 | 2.56 ±1.92 | 4.43 ±.18 | 2/4 (50%) |

*Pfn = Perfusion
†UW1 = modified UW Solution 1 (see Table 3)
‡UW2 = modified UW Solution 2 (see Table 3)

Taken together, the data from kidneys and livers implied that the herein-disclosed methods for preparing organs for cryopreservation and of preparing organs for transplantation after cryopreservation are broadly applicable.

While various embodiments of the present invention have been described above, it should be understood that they have been presented by way of example, and not limitation. Thus the breadth and scope of the present invention should not be limited by any of the above described exemplary embodiments, but should be defined only in accordance with the following claims and their equivalents. Since it will be understood by those of skill in the art that various changes in form and detail may be made therein without departing from the spirit and scope of the invention, this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for preparing an organ for transplantation after its cryopreservation with a cryoprotectant, comprising:
    (a) warming said organ to a temperature which permits reperfusion of said organ, wherein damage to said organ is minimized;
    (b) perfusing said organ with a composition comprising a cryoprotectant and at least two osmotic buffering agents, wherein said composition has a non-vitrifiable concentration of cryoprotectant that is less than the concentration of cryoprotectant used for said cryopreservation, and wherein said at least two osmotic buffering agents includes at least one low molecular weight osmotic buffering agent having a molecular weight of less than 1000 daltons and at least one high molecular weight osmotic buffering agent having a molecular weight of at least 1000 daltons; and
    (c) perfusing substantially all of said cryoprotectant out of said organ while concurrently increasing the temperature of said organ to render said organ suitable for transplantation.

2. The method of claim 1, wherein said cryopreservation is by vitrification.

3. The method of claim 1, wherein said cryopreservation is by freezing.

4. The method of claim 1, wherein said low molecular weight osmotic buffering agent is selected from the group consisting of maltose, potassium and sodium fructose 1,6-diphosphate, potassium and sodium lactobionate, potassium and sodium glycerophosphate, raffinose, maltopentose, stachyose, sucrose and mannitol.

5. The method of claim 1, wherein said low molecular weight osmotic buffering agent is sucrose.

6. The method of claim 1, wherein said low molecular weight osmotic buffering agent is mannitol.

7. The method of claim 1, wherein said high molecular weight osmotic buffering agent is selected from the group consisting of hydroxyethyl starch having a molecular weight of $\leq 450,000$ daltons, polyvinylpyrrolidine, potassium raffinose undecaacetate and Ficoll having a molecular weight of 1,000 to 100,000 daltons.

8. The method of claim 1, wherein said high molecular weight osmotic buffering agent is hydroxyethyl starch.

9. The method of claim 8, wherein the molecular weight of said hydroxyethyl starch is approximately 450,000 daltons.

10. The method of claim 1, wherein said at least two osmotic buffering agents comprises one low molecular weight osmotic buffering agent having a molecular weight of less than 1000 daltons and one high molecular weight osmotic buffering agent having a molecular weight of at least 1000 daltons to 500,000 daltons.

11. The method of claim 10, wherein, in step (c), the concentration of the low molecular weight osmotic buffering agent is reduced to approximately 50 mM and the concentration of the high molecular weight osmotic buffering agent is held steady at approximately 3–8% w/v while the concentration of the cryoprotectant is reduced to less than 200 mM.

12. The method of claim 11, wherein, after step (c), the concentration of the low molecular weight and high molecular weight osmotic buffering agents are not further changed prior to transplantation of the organ.

13. The method of claim 1, wherein the concentration of the low molecular weight osmotic buffering agent is reduced to a nonzero value while the concentration of said cryoprotectant is reduced to less than 200 millimolar.

14. The method of claim 13, wherein the concentration of said low molecular weight osmotic buffering agent is reduced to between 25 mM and 500 mM.

15. The method of either claim 13 or 14, wherein the concentration of said cryoprotectant is reduced to zero.

16. The method of claim 1, wherein said low molecular weight osmotic buffering agent is selected from the group consisting of mannitol and sucrose, and said high molecular weight osmotic buffering agent is hydroxyethyl starch.

17. The method of claim 16, wherein once all of said cryoprotectant is removed from said organ, the hydroxyethyl starch concentration is reduced to a non-zero level while the sucrose concentration is reduced to zero and mannitol is concomitantly perfused into said organ.

18. The method of either of claims 1 or 10 wherein said organ is a liver.

19. The method of either of claims 7 or 10 wherein said organ is a kidney.

20. The method of claim 1, wherein, in step (b), said organ is perfused with said composition for a time sufficient to permit the approximate osmotic equilibration of said organ.

21. A method for preparing a liver for transplantation after its cryopreservation by vitrification with a vitrifiable concentration of cryoprotectant, comprising:
    (a) warming said liver to a temperature that permits reperfusion of said liver, wherein damage to said liver is minimized;
    (b) perfusing said organ with a composition comprising a non-vitrifiable concentration of cryoprotectant and no osmotic buffering agents; and
    (c) perfusing substantially all of said cryoprotectant out of said liver while concurrently increasing the temperature of said liver to render said liver suitable for transplantation.

22. The method of claim 21, wherein, in step (b), said liver is perfused with said composition for a time sufficient to permit the approximate osmotic equilibration of said liver.

23. A method for preparing an organ for transplantation after its cryopreservation with a cryoprotectant, comprising:
    (a) warming said organ to a temperature which permits reperfusion of said organ, wherein damage to said organ is minimized;
    (b) perfusing said organ with a composition comprising a cryoprotectant and a high molecular weight osmotic buffering agent having a molecular weight of at least 1000 daltons, wherein said composition has a non-vitrifiable concentration of cryoprotectant that is less than the concentration of cryoprotectant used for said cryopreservation; and
    (c) perfusing substantially all of said cryoprotectant out of said organ while concurrently increasing the temperature of said organ to render said organ suitable for transplantation.

24. The method of claim 23, wherein said cryopreservation is by vitrification.

25. The method of claim 23, wherein said cryopreservation is by freezing.

26. The method of claim 23, wherein said osmotic buffering agent in step (b) comprises at least two osmotic buffering agents.

27. The method of claim 23, wherein said high molecular weight osmotic buffering agent is selected from the group consisting of hydroxyethyl starch having a molecular weight of $\leq 450,000$ daltons, polyvinylpyrrolidine, potassium raffinose undecaacetate and Ficoll having a molecular weight of 1,000 to 100,000 daltons.

28. The method of claim 23, wherein said high molecular weight osmotic buffering agent is hydroxyethyl starch.

29. The method of claim 28, wherein the molecular weight of said hydroxyethyl starch is approximately 450,000.

30. The method of claim 23, wherein said organ is a liver.

31. The method of claim 23, wherein, in step (b), said organ is perfused with said composition for a time sufficient to permit the approximate osmotic equilibration of said organ.

32. The method of claim 5, further comprising perfusing said organ with a composition comprising mannitol after substantially all of said cryoprotectant is perfused out of said organ.

* * * * *